US010864180B2

(12) United States Patent
Mathios et al.

(10) Patent No.: US 10,864,180 B2
(45) Date of Patent: Dec. 15, 2020

(54) COMBINATION OF IMMUNOTHERAPY WITH LOCAL CHEMOTHERAPY FOR THE TREATMENT OF MALIGNANCIES

(71) Applicant: THE JOHNS HOPKINS UNIVERSITY, Baltimore, MD (US)

(72) Inventors: Dimitrios Mathios, Baltimore, MD (US); Betty Tyler, Baltimore, MD (US); Drew Pardoll, Baltimore, MD (US); Henry Brem, Baltimore, MD (US); Michael Lim, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/136,149

(22) Filed: Apr. 22, 2016

(65) Prior Publication Data
US 2016/0310453 A1 Oct. 27, 2016

Related U.S. Application Data

(60) Provisional application No. 62/151,619, filed on Apr. 23, 2015.

(51) Int. Cl.
*A61K 31/175* (2006.01)
*C07K 16/28* (2006.01)
*A61K 39/00* (2006.01)

(52) U.S. Cl.
CPC ........ *A61K 31/175* (2013.01); *C07K 16/2818* (2013.01); *A61K 2039/505* (2013.01)

(58) Field of Classification Search
CPC ......... C07K 16/00–468; A61K 39/395–39558; A61K 2039/505; A61K 31/175
See application file for complete search history.

(56) References Cited

U.S. PATENT DOCUMENTS

| 9,132,281 | B2 * | 9/2015 | Zeng ...................... A61K 45/06 |
| 2014/0056844 | A1 | 2/2014 | Tsang et al. |
| 2015/0210769 | A1 * | 7/2015 | Freeman ............ A61K 39/3955 424/136.1 |

FOREIGN PATENT DOCUMENTS

WO WO-2012177624 A2 * 12/2012 ......... C07K 16/2818

OTHER PUBLICATIONS

Frazier et al., Neurosurg Clin N Am, 2010: 21:187-194.*
Nicholas et al., Brain Tumor Res Treat, 2013; 1:2-8.*
Kim & Eder, Cancer Network, Nov. 2014; available at www.cancernetwork.com/oncology-journal/prospects-targeting-pd-1-and-pd-I1-various-tumor-types; last visited Jul. 14, 2017.*
Zhou et al., Cancer J, 2012; 18(1): doi: 10.1097/PPO.0b013e318244d8ae, pp. 1-22.*
L. Kleinberg. Core Evidence 2012:7, doi: 10.2147/CE.S2324 (Year: 2012).*
FDA Center for Drug Research and Evaluation Summary Review for application No. 125554Orig1s000 (Year: 2014).*
Champiat et al., J Thoracic Oncol 9:144-153 (Year: 2014).*
Blackburn, S.D., et al., Coregulation of CD8+ T cell exhaustion by multiple inhibitory receptors during chronic viral infection. Nature Immunology. 2009; 10(1): 29-37.
Bloch, O., et al., Gliomas promote immunosuppression through induction of B7-H1 expression in tumor-associated macrophages. Clinical Cancer Research : an Official Journal of the American Association for Cancer Research. 2013;19(12):3165-75.
Brahmer, J.R., et al., Safety and activity of anti-PD-L1 antibody in patients with advanced cancer. The New England Journal of Medicine. 2012;366(26):2455-65.
Brem, H., Polymers to treat brain tumours. Biomaterials. 1990;11(9):699-701.
Brem, H., et al., Placebo-controlled trial of safety and efficacy of intraoperative controlled delivery by biodegradable polymers of chemotherapy for recurrent gliomas. The Polymer-Brain Tumor Treatment Group. Lancet. 1995;345(8956):1008-12.
Brooks, W.H., et al., Depressed cell-mediated immunity in patients with primary intracranial tumors. Characterization of a humoral immunosuppressive factor. The Journal of Experimental Medicine. 1972;136(6):1631-47.
Fleming, A.B. and Saltzman, W.M. Pharmacokinetics of the carmustine implant. Clinical Pharmacokinetics. 2002;41(6):403-19.
Gabrusiewicz, K., et al., Characteristics of the alternative phenotype of microglia/macrophages and its modulation in experimental gliomas. PloS One. 2011;6(8):e23902.
Gilbert, M.R., et al., Dose-dense temozolomide for newly diagnosed glioblastoma: a randomized phase III clinical trial. J. Clin. Oncology: Official Journal of the American Society of Clinical Oncology. 2013;31(32):4085-91.
Grossman, S.A., et al., Immunosuppression in patients with high-grade gliomas treated with radiation and temozolomide. Clinical Cancer Research : an Official Journal of the American Association for Cancer Research. 2011;17(16):5473-80.
Hailemichael, Y. and Overwijk, W.W., Cancer vaccines: Trafficking of tumorspecific T cells to tumor after therapeutic vaccination. The International Journal of Biochemistry & Cell Biology. 2014;53:46-50.
Hamid, O., et al., Safety and tumor responses with lambrolizumab (anti-PD1) in melanoma. The New England Journal of Medicine. 2013;369(2):134-44.

(Continued)

*Primary Examiner* — Jessica H Roark
(74) *Attorney, Agent, or Firm* — Michael Best & Friedrich LLP

(57) ABSTRACT

The presently disclosed subject matter provides methods, compositions, and kits for the treatment of cancer using a combination treatment comprising a locally administered chemotherapy and an immunotherapeutic agent. The presently disclosed subject matter also provides methods of promoting the combination treatment and instructing a patient to receive the combination treatment are also provided, as well immunotherapeutic, non-immunosuppressive compositions comprising the combination treatment, and methods of using the immunotherapeutic, non-immunosuppressive compositions for treating cancer.

9 Claims, 54 Drawing Sheets

(56) References Cited

OTHER PUBLICATIONS

Hirano et al., Blockade of B7-H1 and PD-1 by monoclonal antibodies potentiates cancer therapeutic immunity. Cancer Res. Feb. 1, 2005; 65(3): 1089-96.
Hussain, S.F., et al., The role of human glioma-infiltrating microglia/macrophages in mediating antitumor immune responses. Neuro-Oncology. 2006;8(3):261-79.
Jackson, C., et al., Vaccine strategies for glioblastoma: progress and future directions. Immunotherapy. 2013;5(2):155-67.
Kim, G.Y., et al., Resorbable polymer microchips releasing BCNU inhibit tumor growth in the rat 9L flank model. Journal of Controlled Release : Official Journal of the Controlled Release Society. 2007;123(2):172-8.
Le, D.T and Jaffee, E.M., Regulatory T-cell modulation using cyclophosphamide in vaccine approaches: a current perspective. Cancer Research. 2012;72(14):3439-44.
Litterman, A.J., et al., Alkylating chemotherapy may exert a uniquely deleterious effect upon neo-antigen-targeting anticancer vaccination. Oncoimmunology. 2013;2(10):e26294.
Malmstrom, A., et al., Temozolomide versus standard 6-week radiotherapy versus hypofractionated radiotherapy in patients older than 60 years with glioblastoma: the Nordic randomised, phase 3 trial. The Lancet Oncology. 2012;13(9):916-26.
Menard, C., et al., Cancer chemotherapy: not only a direct cytotoxic effect, but also an adjuvant for antitumor immunity. Cancer Immunology, Immunotherapy : CII. 2008;57(11):1579-87.
Nowak, A.K., et al., Gemcitabine exerts a selective effect on the humoral immune response: implications for combination chemoimmunotherapy. Cancer Research. 2002;62(8):2353-8.
Ohlfest, J.R., et al., Vaccine injection site matters: qualitative and quantitative defects in CD8 T cells primed as a function of proximity to the tumor in a murine glioma model. Journal of Immunology. 2013;190(2):613-20.
Pardoll, D.M., The blockade of immune checkpoints in cancer immunotherapy. Nature Reviews Cancer. 2012;12(4):252-64.
Parsa, A.T., et al., Loss of tumor suppressor PTEN function increases B7-H1 expression and immunoresistance in glioma. Nature Medicine. 2007;13(1):84-8.
Preynat-Seauve, O., et al., Tumor-infiltrating dendritic cells are potent antigen-presenting cells able to activate T cells and mediate tumor rejection. Journal of Immunology. 2006;176(1):61-7.
Sampson, J.H., et al., Immunologic escape after prolonged progression-free survival with epidermal growth factor receptor variant III peptide vaccination in patients with newly diagnosed glioblastoma. Journal of Clinical Oncology : an Official Journal of the American Society of Clinical Oncology. 2010;28(31):4722-9.
Smpson, J.H., et al., Greater chemotherapy-induced lymphopenia enhances tumor-specific immune responses that eliminate EGFRvIII-expressing tumor cells in patients with glioblastoma. Neuro-Oncology. 2011;13(3):324-33.
Sarkaria, J.N., et al., Combination of temsirolimus (CCI-779) with chemoradiation in newly diagnosed glioblastoma multiforme (GBM) (NCCTG trial N027D) is associated with increased infectious risks. Clinical Cancer Research : an Official Journal of the American Association for Cancer Research. 2010;16(22):5573-80.
Stupp, R., et al., Effects of radiotherapy with concomitant and adjuvant temozolomide versus radiotherapy alone on survival in glioblastoma in a randomised 25 phase III study: 5-year analysis of the EORTC-NCIC trial. The Lancet Oncology. 2009;10(5):459-66.
Topalian, S.L., et al., Safety, activity, and immune correlates of anti-PD1 antibody in cancer. The New England Journal of Medicine. 2012;366(26):2443-54.
Van der Most, R.G., et al., Combining immunotherapy with chemotherapy to treat cancer. Discovery Medicine. 2005;5(27):265-70.
Walter, S., et al., Single-dose cyclophosphamide synergizes with immune responses to the renal cell cancer vaccine IMA901. Oncoimmunology. 2013;2(1):e22246.
Westphal, M., et al., A phase 3 trial of local chemotherapy with biodegradable carmustine (BCNU) wafers (Gliadel wafers) in patients with primary malignant glioma. Neuro-Oncology. 2003;5(2):79-88.
Zeng, J., et al., Anti-PD1 blockade and stereotactic radiation produce longterm survival in mice with intracranial gliomas. International Journal of Radiation Oncology, Biology, Physics. 2013;86(2):343-9.
Mathios, IT-21 PD-1 Blockade shows synergistic survival anti tumor immune response and long term memory with interstitial but not systemic chemotherapy: Study in a murine glioblastoma model. Neuro-Oncology. 2014;110(118).
The International Search Report and the Written Opinion dated Oct. 21, 2016 for a corresponding International Patent Application No. PCT/US2016/028861.
Fritzell, S. et al., 'Intratumoral temozolomide synergizes with immunotherapy in a T cell-dependent fashion' Cancer Immunology, Immunotherapy, 2013, vol. 62, pp. 1463-1474 See abstract; and pp. 1465-1467.
Tong, Y. et al., 'Combined intratumoral injection of bone marrow-derived dendritic cells and systemic chemotherapy to treat pre-existing murine tumors' Cancer Research, 2001, vol. 61, pp. 7530-7535 See abstract; and pp. 7531-7533.
Hurwitz, A. A. et al., 'Combination immunotherapy of primary prostate cancer in a transgenic mouse model using CTLA-4 blockade' Cancer Research, 2000, vol. 60, pp. 2444-2448 See abstract; and pp. 2445-2447.
Sersa, G. et al., 'Improvement of combined modality therapy with cisplatin and radiation using electroporation of tumors' International Journal of Radiation Oncology Biology Physics, 2000, vol. 46, No. 4, pp. 1037-1041 See abstract; and pp. 1037-1039.
Litterman, A. et al., "Profound Impairment of Adaptive Immune Responses by Alkylating Chemotherapy" The Journal of Immunology, May 17, 2013, 190 (12); pp. 6259-6268.

* cited by examiner

Brain

Teff DLNs: Day 30

Day 30

Control

Anti-PD-1

LC i.p. BCNU

DAY 30 CD8eff CELLS

DAY 30 TREG CELLS CONTROL

ISOTYPE CONTROL

S 10,864,180 B2

COMBINATION OF IMMUNOTHERAPY WITH LOCAL CHEMOTHERAPY FOR THE TREATMENT OF MALIGNANCIES

CROSS-REFERENCE TO RELATED APPLICATIONS

This application claims the benefit of U.S. Provisional Application No. 62/151,619, filed Apr. 23, 2015, the contents of which are incorporated herein by reference in their entirety.

BACKGROUND

Glioblastoma is the most common and aggressive primary brain tumor in adults. Despite multimodal treatment, clinical outcomes remain poor with the majority of patients surviving less than 2 years (Stupp et al., 2009; Malmstrom et al., 2012; Gilbert et al., 2013). Although glioblastoma rarely metastasizes, these tumors and their treatment have systemic sequelae, including severe immunosuppression (Parsa et al., 2007; Bloch et al., 2013; Brooks et al., 1972; Grossman et al., 2011). In an attempt to mitigate the systemic effects of chemotherapy and to maximize the dose delivered directly to tumor cells, local intra-tumoral chemotherapy in the form of biodegradable BCNU wafers (Gliadel™ wafers, LC) was introduced in the early 1990s (Brem, 1990) and subsequently approved by the FDA for recurrent GBM in 1996 (Brem et al., 1995) and for newly diagnosed GBM in 2003 (Westphal et al., 2003).

Immunotherapy is an exciting approach to treating cancer. Immunotherapy approaches are showing great promise. As an example, anti-PD1 monoclonal antibodies (mAbs) have emerged as a promising therapeutic strategy as PD1 blockade has demonstrated activity against a number of solid tumors and appears to be associated with robust antitumor immunity with reduced adverse events compared to another effective mAb, CTLA-4 blockade or to the combination of anti-PD1 and anti-CTLA-4 (Topalian et al., 2012; Brahmer et al., 2012; Hamid et al., 2013). PD1 is expressed on the membrane of tumor infiltrating lymphocytes (TILs) and interacts with its ligands PD-L1 and PD-L2, which are expressed on both tumor cells and immune cells. The PD1-PD-L1 interaction results in decreased survival and proliferation of CD8+ T-cells, reduced cytokine production, and eventually T cell exhaustion. Blockade of PD1-PD-L1 interaction can restore the function of T-cells releasing an anti-tumor immune response (Pardoll, 2012; Blackburn et al., 2009). While immunotherapy carries great potential, questions remain about the sequence or role of chemotherapy with immunotherapy. Current thinking in clinical trial design discourages the combination of chemotherapy and immunotherapy due to the concern that the immunosuppressive side effects of chemotherapy may blunt the activity of immunotherapeutic agents (Nowak et al., 2002; Sarkaria et al., 2010; van der Most et al., 2005).

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning. A Laboratory Manual, 3$^{rd}$ ed.*, Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: ncbi.nlm.nih.gov/omim/ and in Online Mendelian Inheritance in Animals (OMIA), a database of genes, inherited disorders and traits in animal species (other than human and mouse), at omia.angis.org.au/contact.shtml. The Kinetochore, Springer, 2009. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

In one aspect, the presently disclosed subject matter provides a method for the treatment of cancer comprising administering to a patient with a cancer an effective amount of a combination treatment comprising: (a) a locally administered chemotherapy; and (b) an immunotherapeutic agent.

In certain aspects, the presently disclosed subject matter provides a method of promoting a combination treatment for the treatment of a patient with a cancer, wherein the combination treatment comprises: (a) a locally administered chemotherapy; and (b) an immunotherapeutic agent.

In some aspects, the presently disclosed subject matter provides a method for prolonging survival of a cancer patient comprising administering to a patient with a cancer an effective amount of a combination treatment comprising: (a) a locally administered chemotherapy; and (b) an immunotherapeutic agent.

In another aspect, the presently disclosed subject matter provides a method of instructing a patient with a cancer by providing instructions to receive a combination treatment comprising; (a) a locally administered chemotherapy; and (b) an immunotherapeutic agent, to extend survival of the patient.

In other aspects, the presently disclosed subject matter provides a kit comprising: (a) a locally administered chemotherapy; (b) an immunotherapeutic agent; and (c) a package insert or label with directions to treat a patient with a cancer by administering a combination treatment comprising the locally administered chemotherapy and the immunotherapeutic agent.

In certain aspects, the presently disclosed subject matter provides an immunotherapeutic, non-immunosuppressive composition comprising: (a) a locally administered chemotherapy; and (b) an immunotherapeutic agent.

In other aspects, the presently disclosed subject matter relates to the use of the immunotherapeutic, non-immunosuppressive composition for the treatment of a cancer.

In still other aspects, the presently disclosed subject matter relates to the use of the immunotherapeutic, non-immunosuppressive composition for the manufacture of a medicament for the treatment of a cancer.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE DRAWINGS

Figure 1:
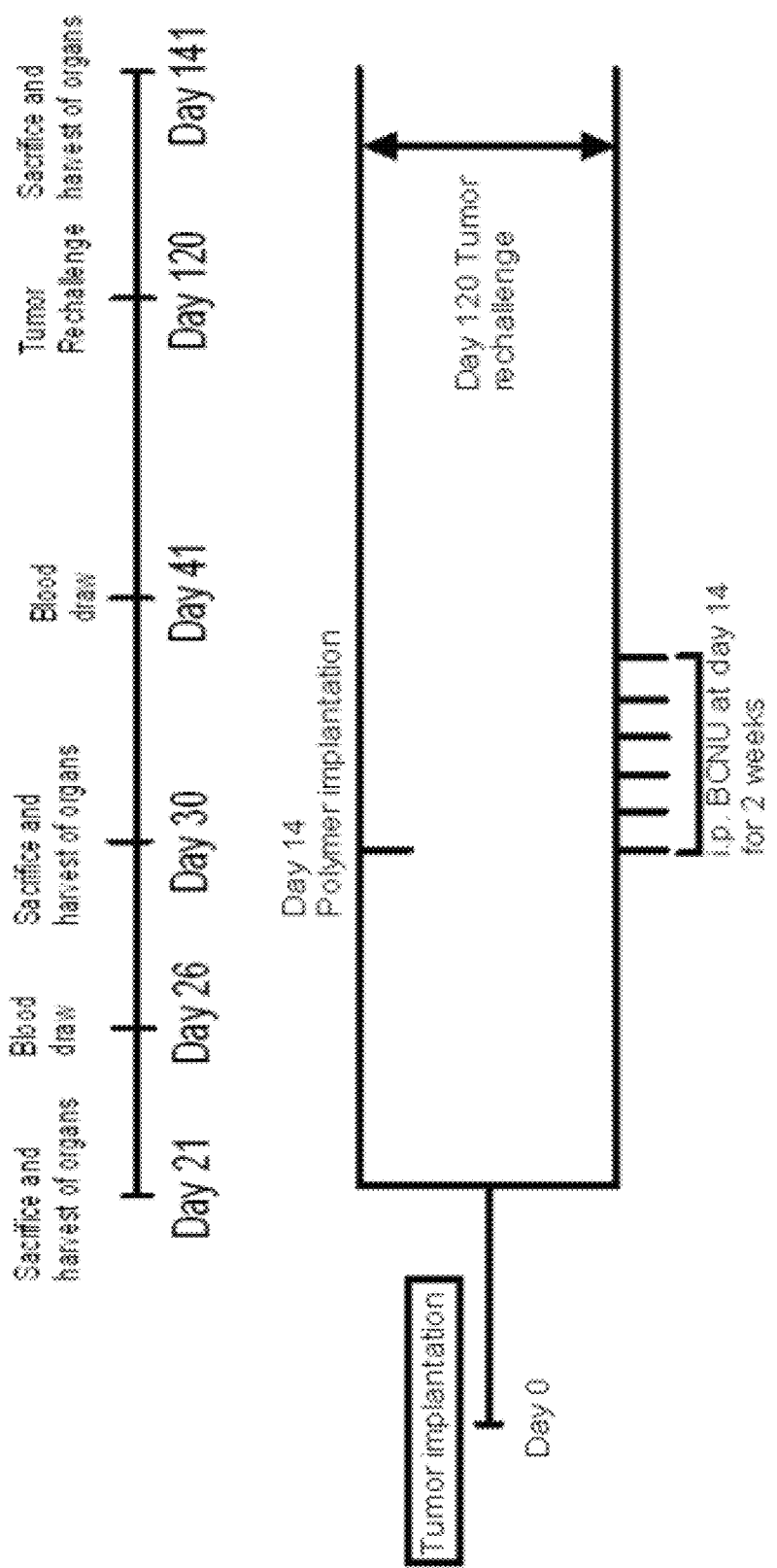
Figure 2:
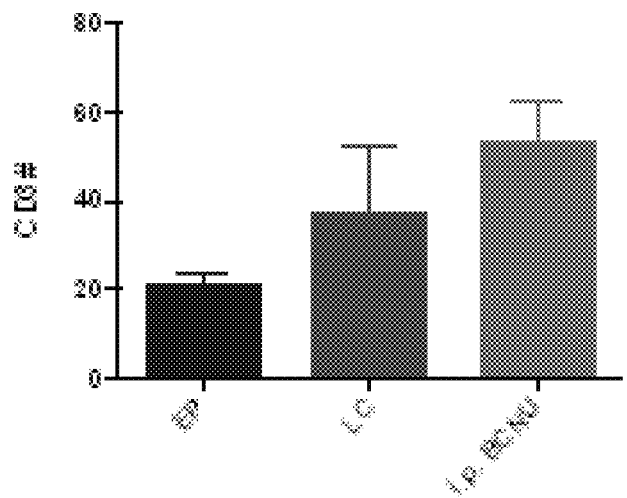
Figure 2:
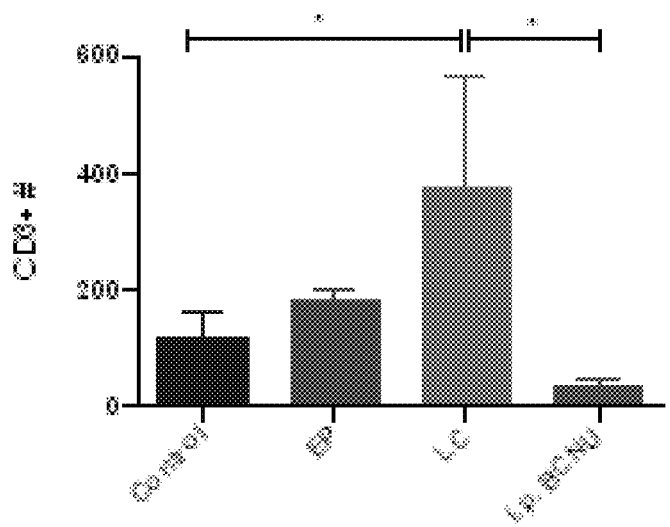
Figure 2:
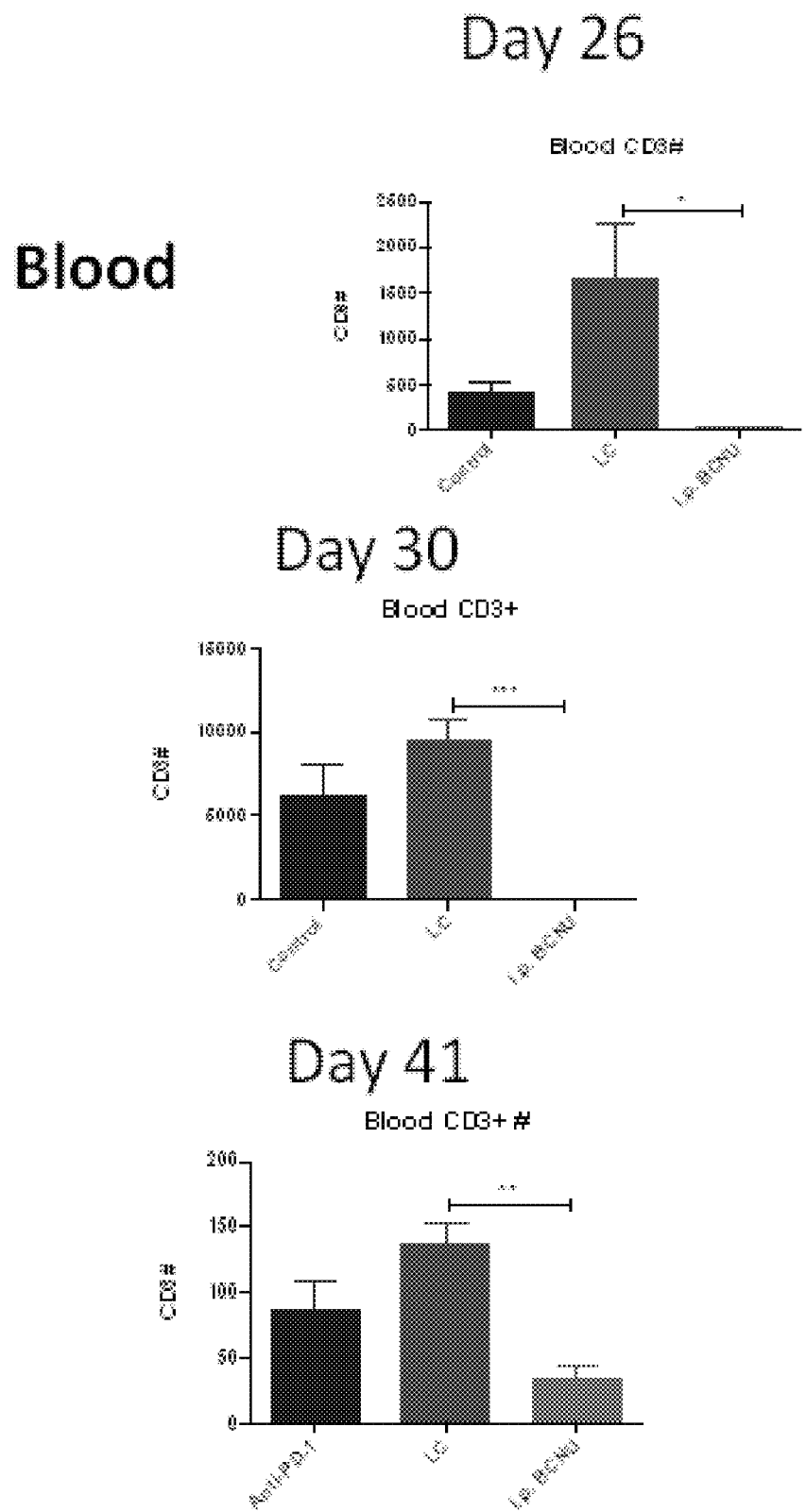
Figure 2:
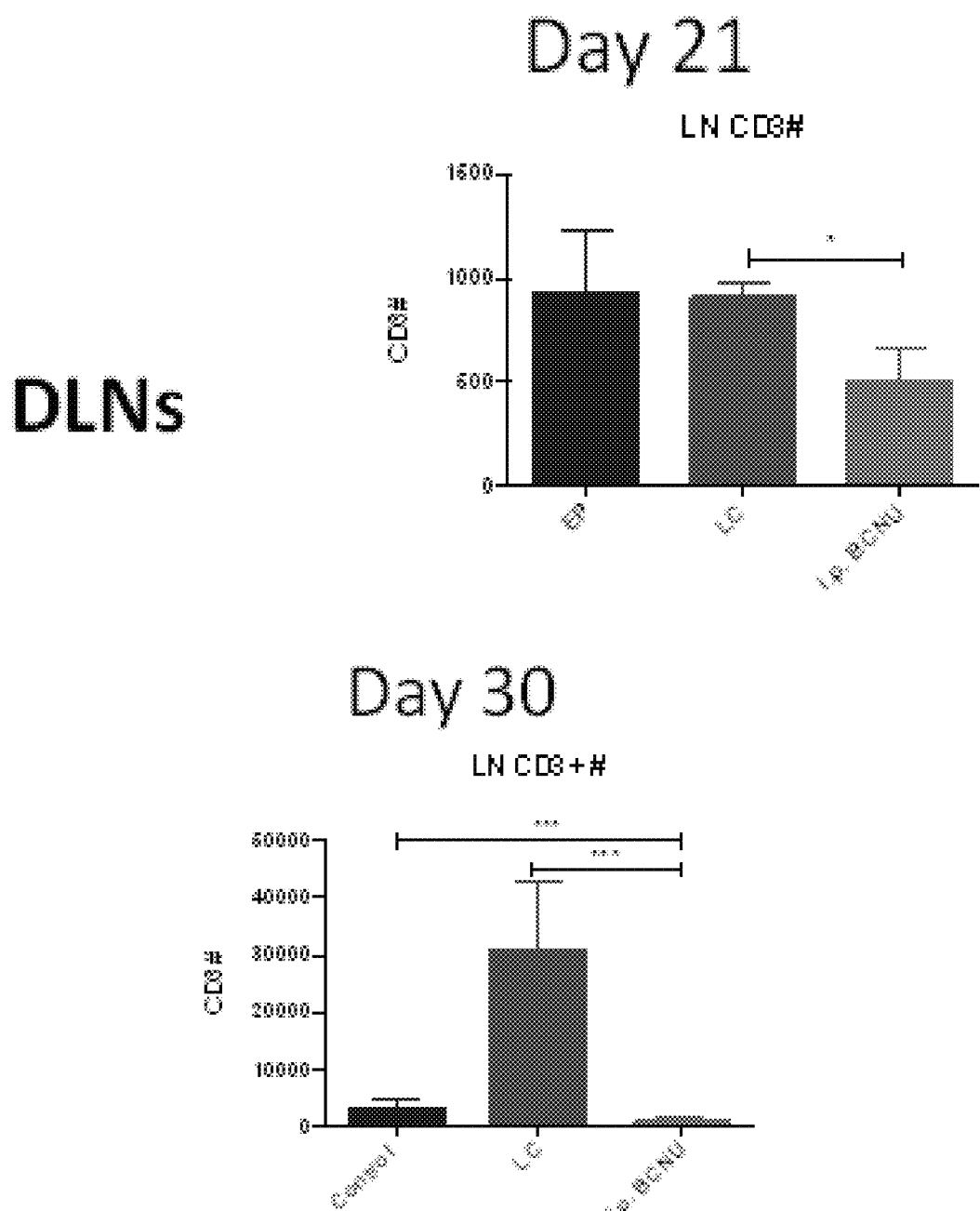
Figure 2:
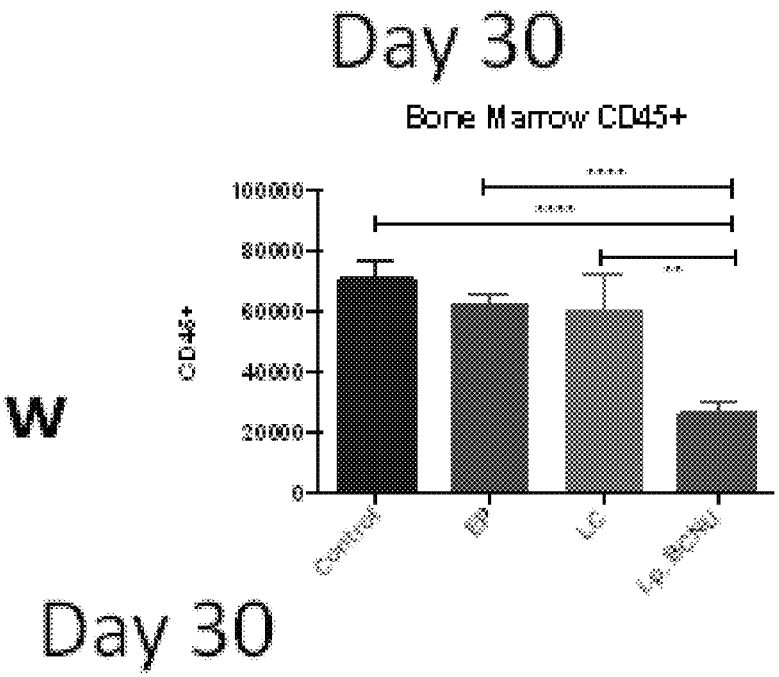
Figure 2:
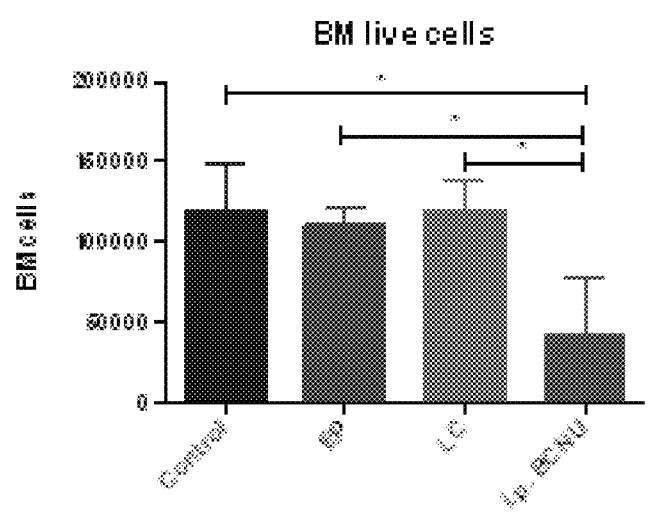
Figure 3:
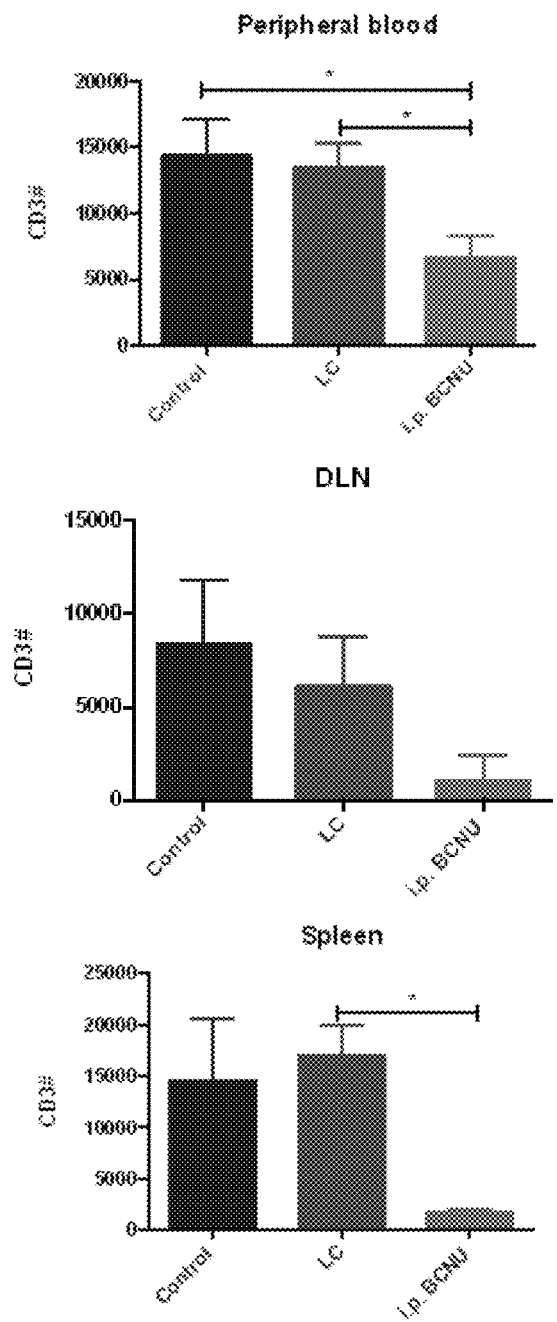
Figure 4:
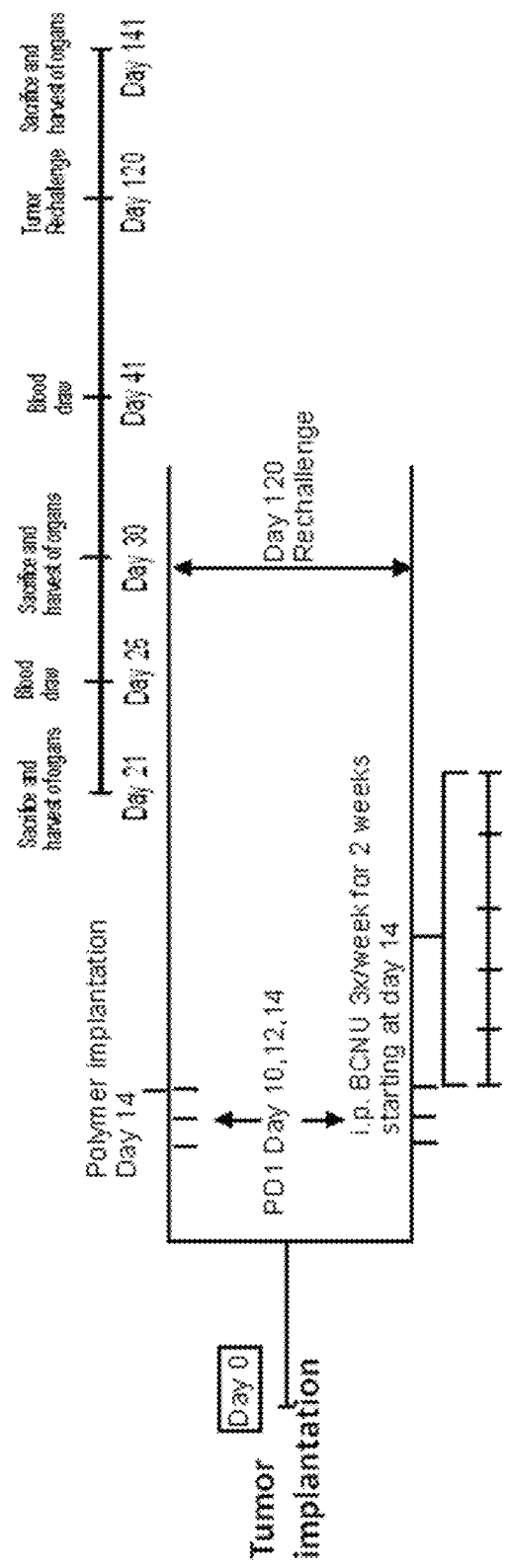
Figure 5:
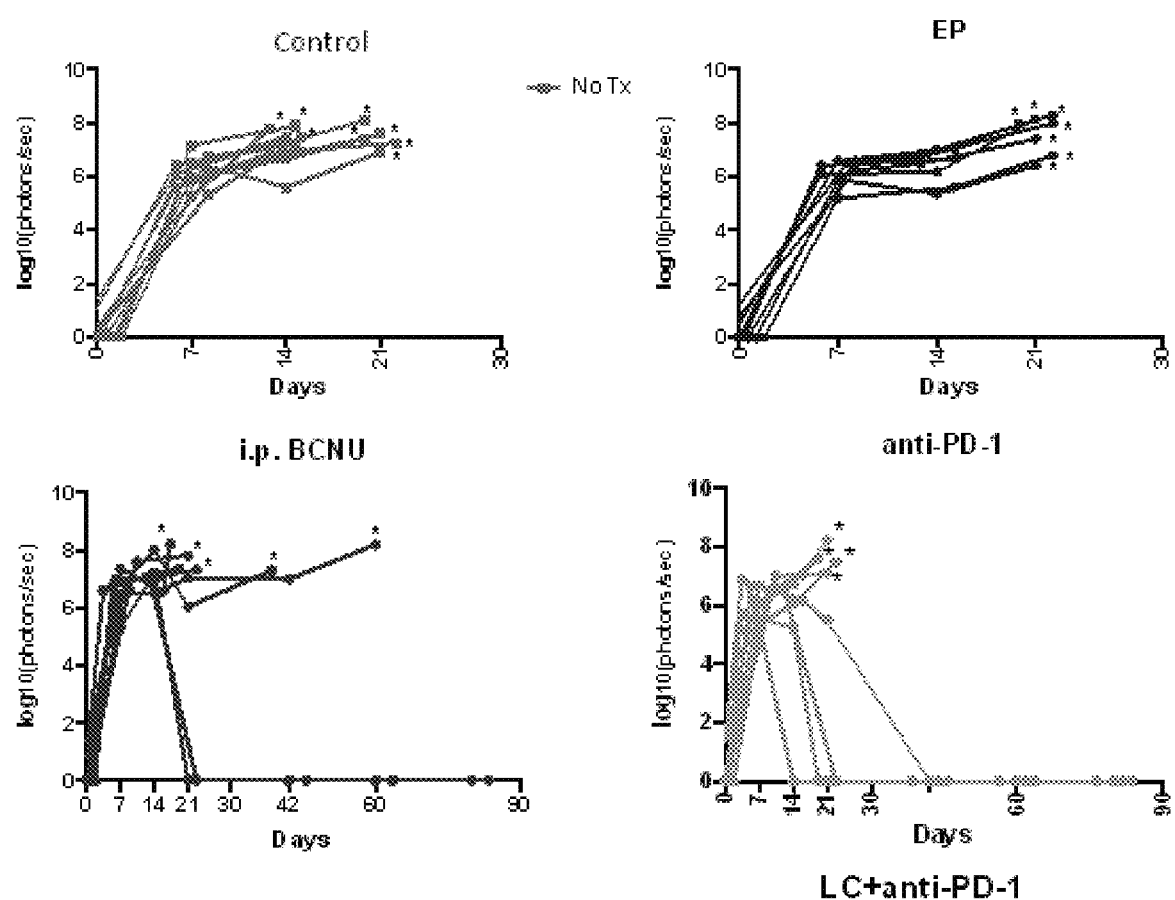
Figure 6:
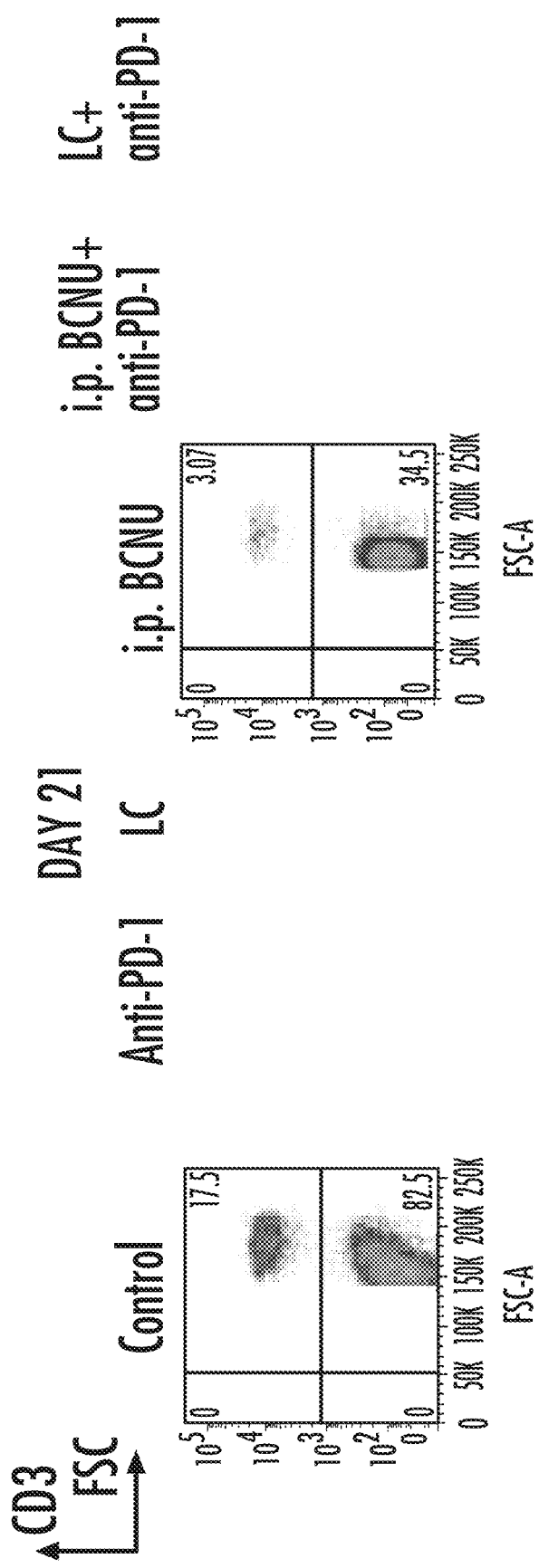
Figure 6:
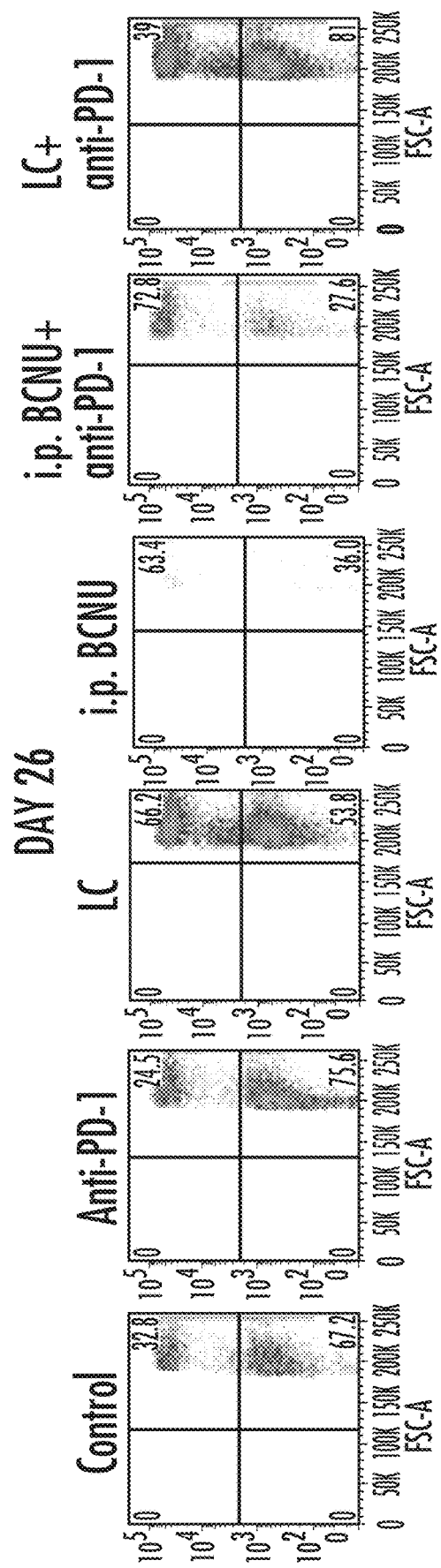
Figure 6:
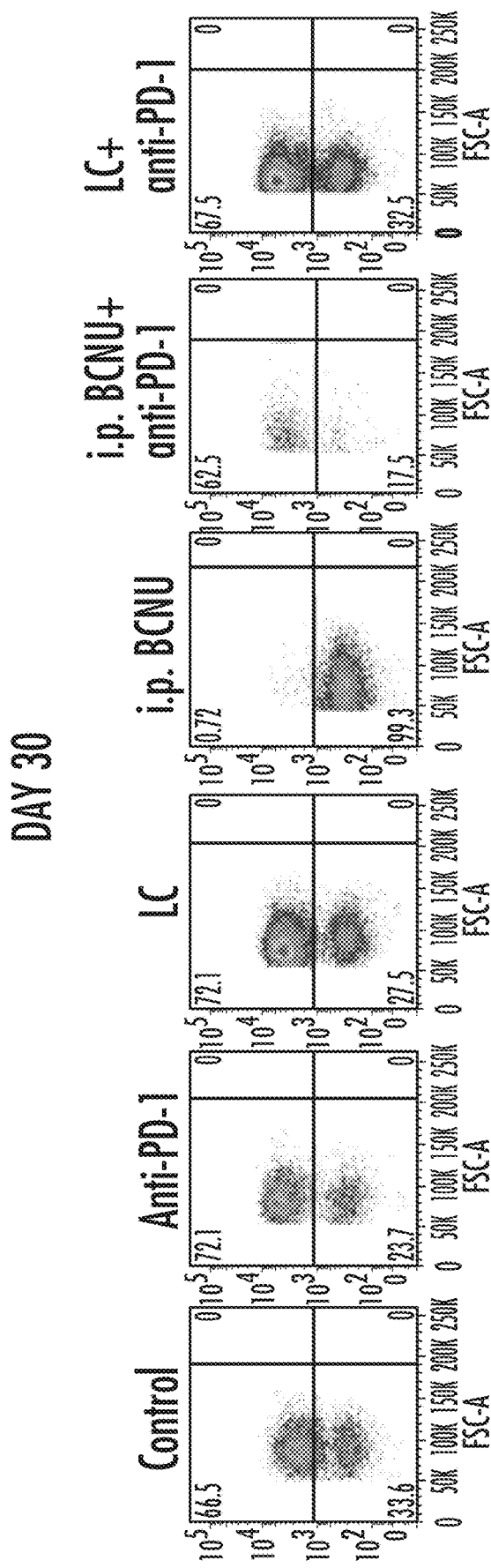
Figure 6:
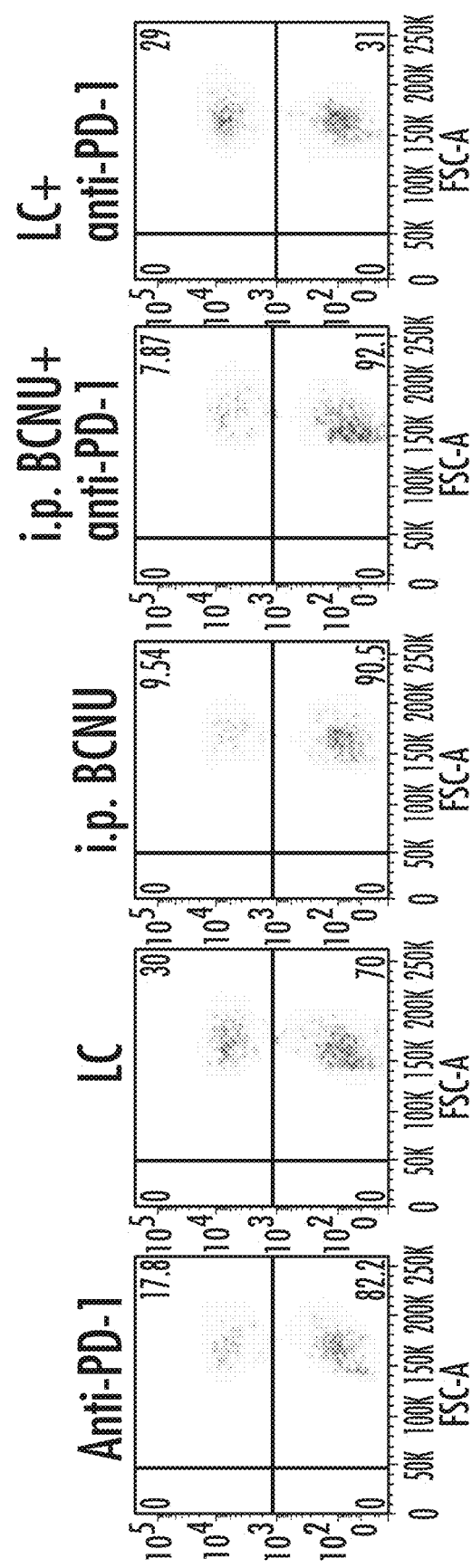
Figure 7:
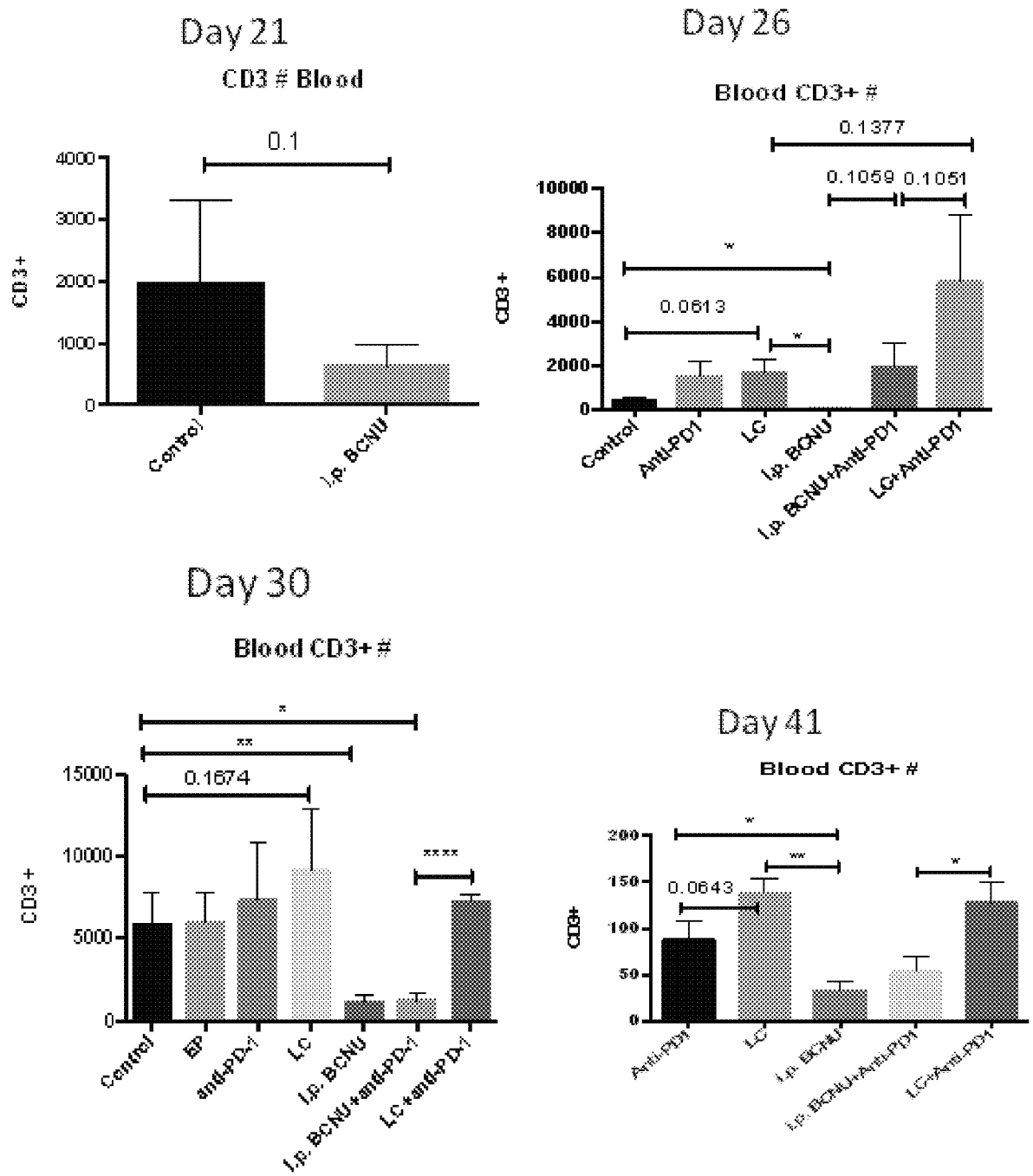
Figure 8:
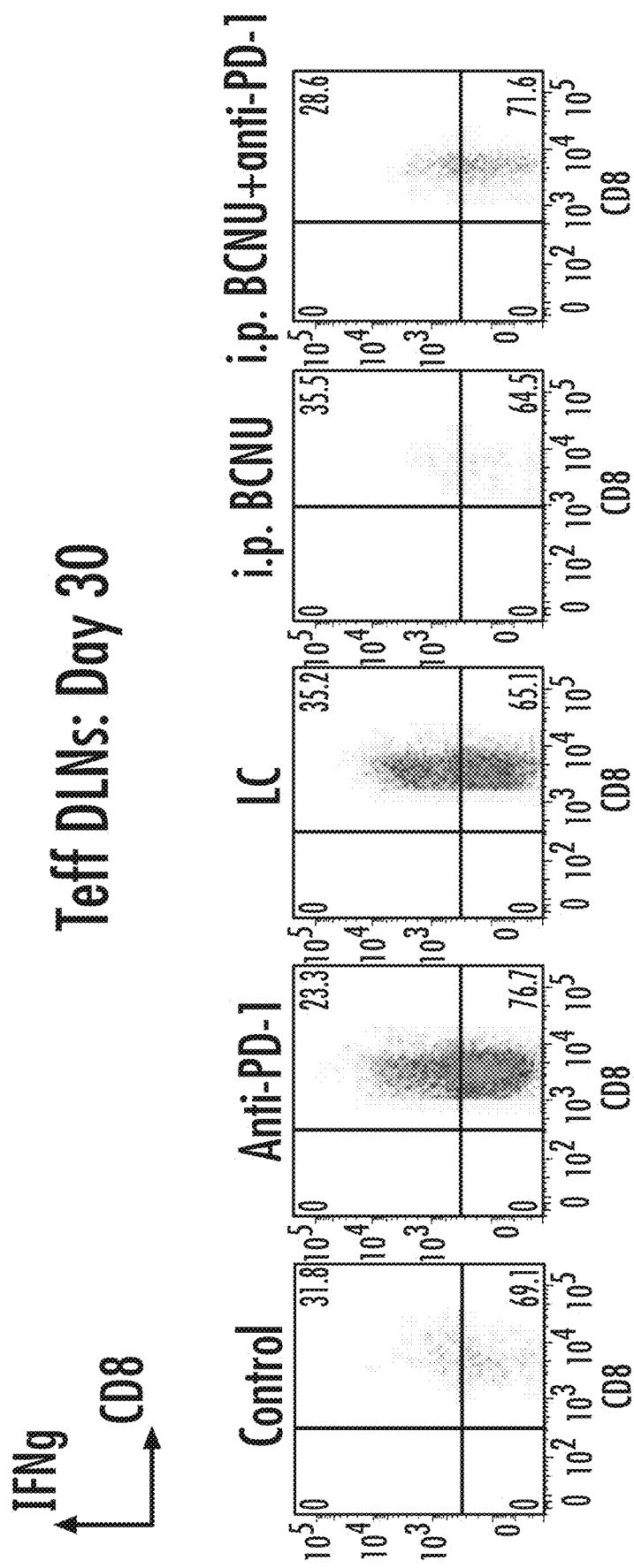
Figure 8:
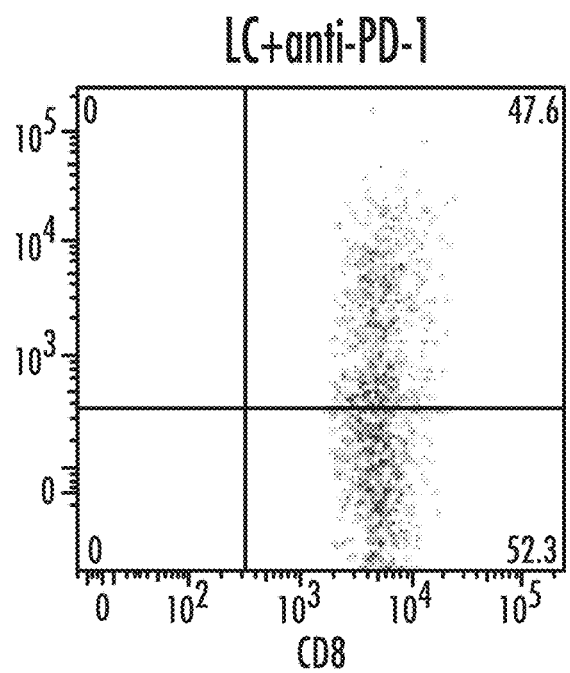
Figure 8:
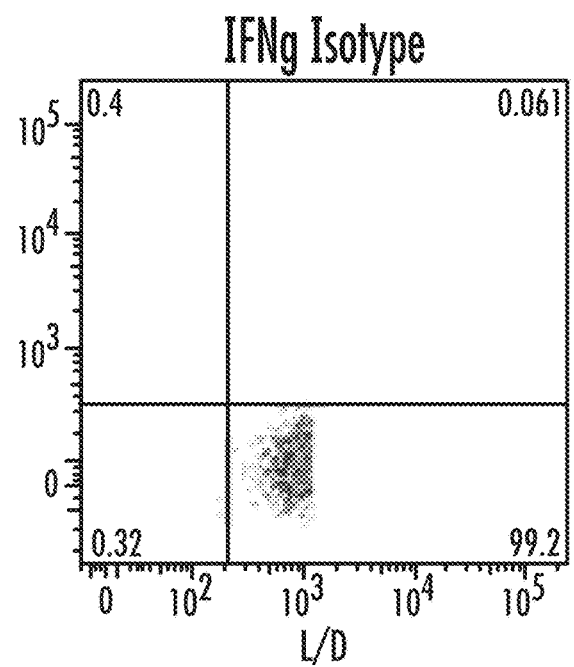
Figure 8:
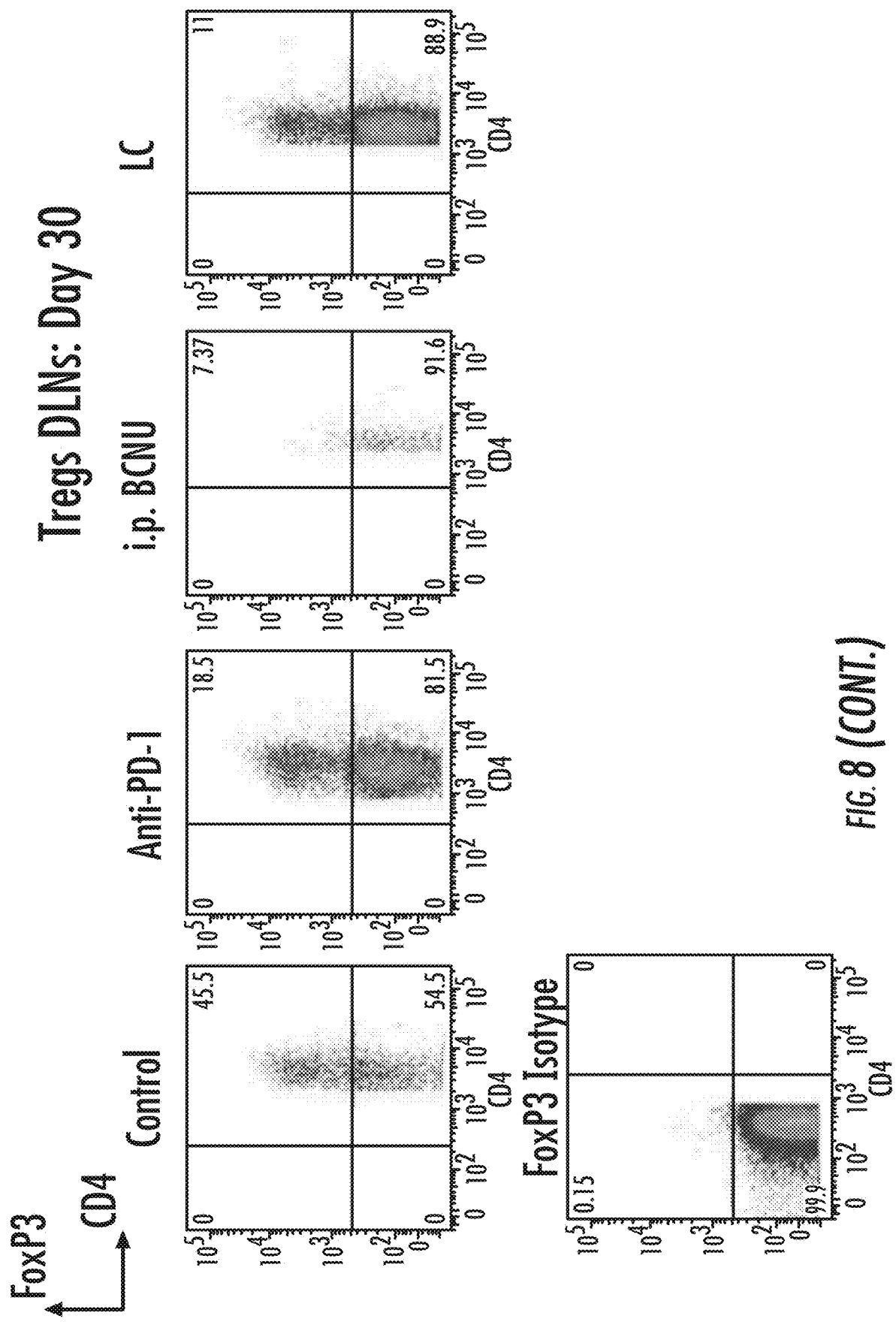
Figure 8:
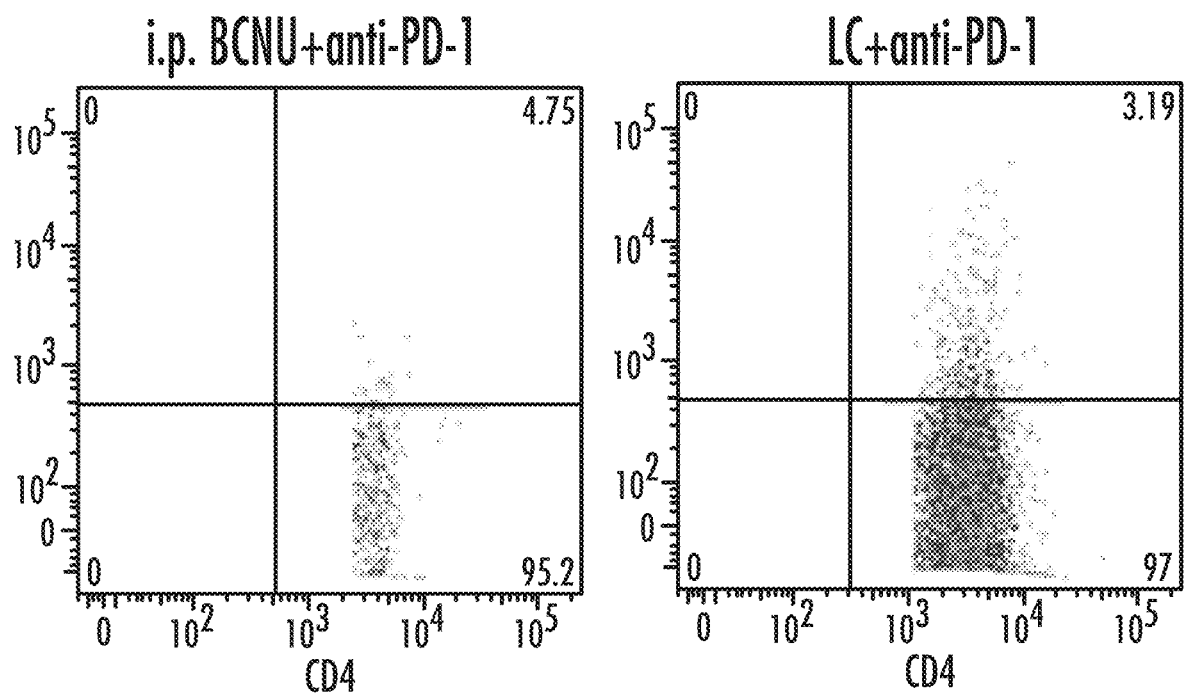
Figure 9:
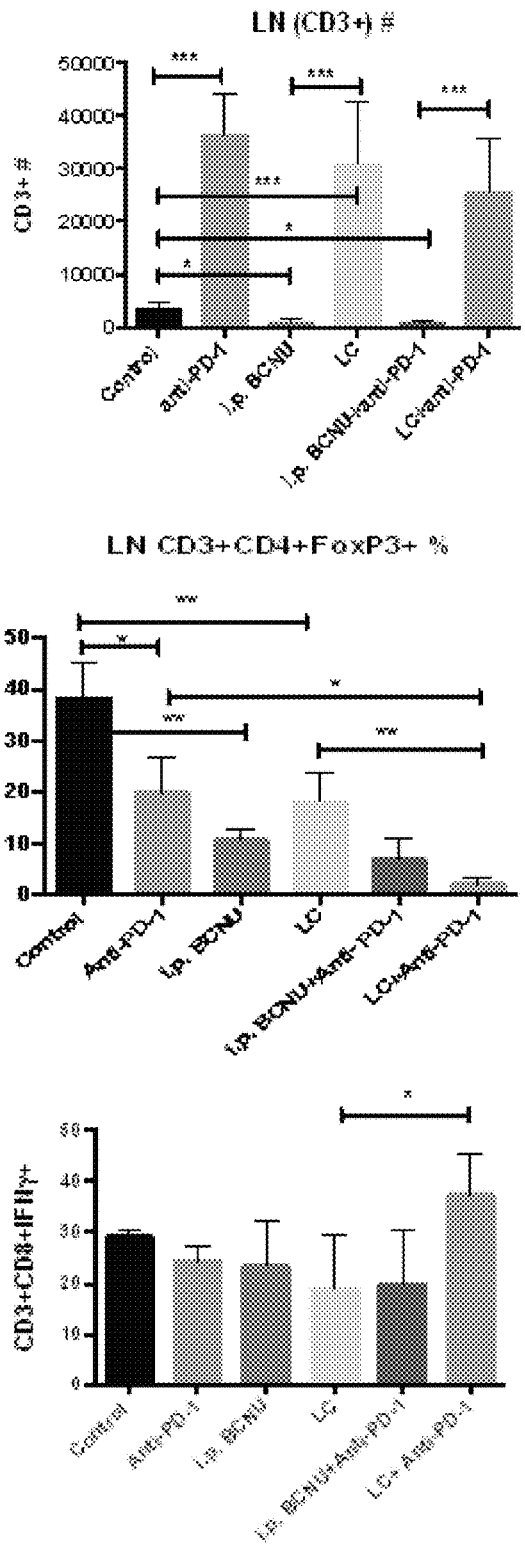
Figure 10:
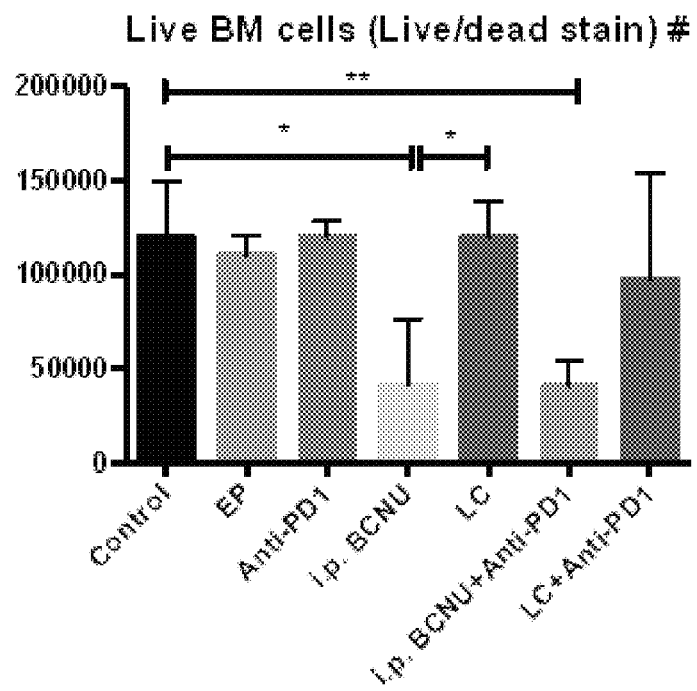
Figure 10:
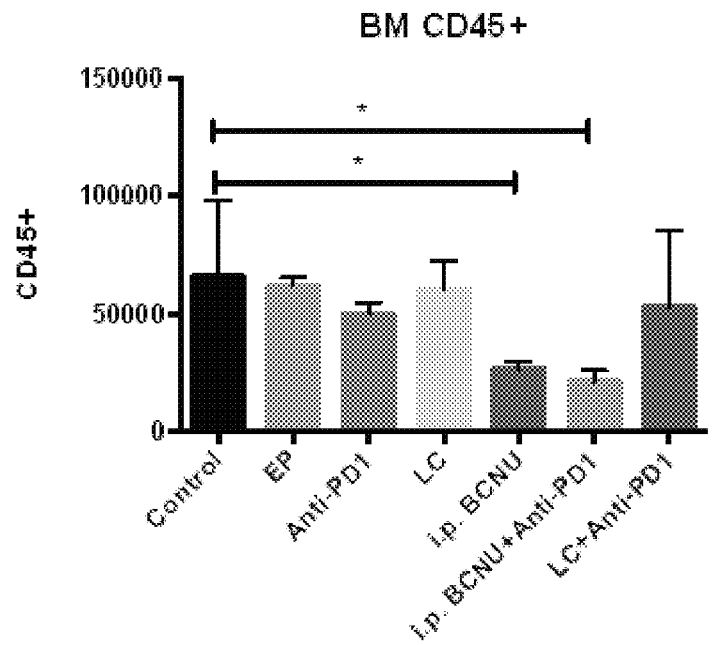
Figure 11:
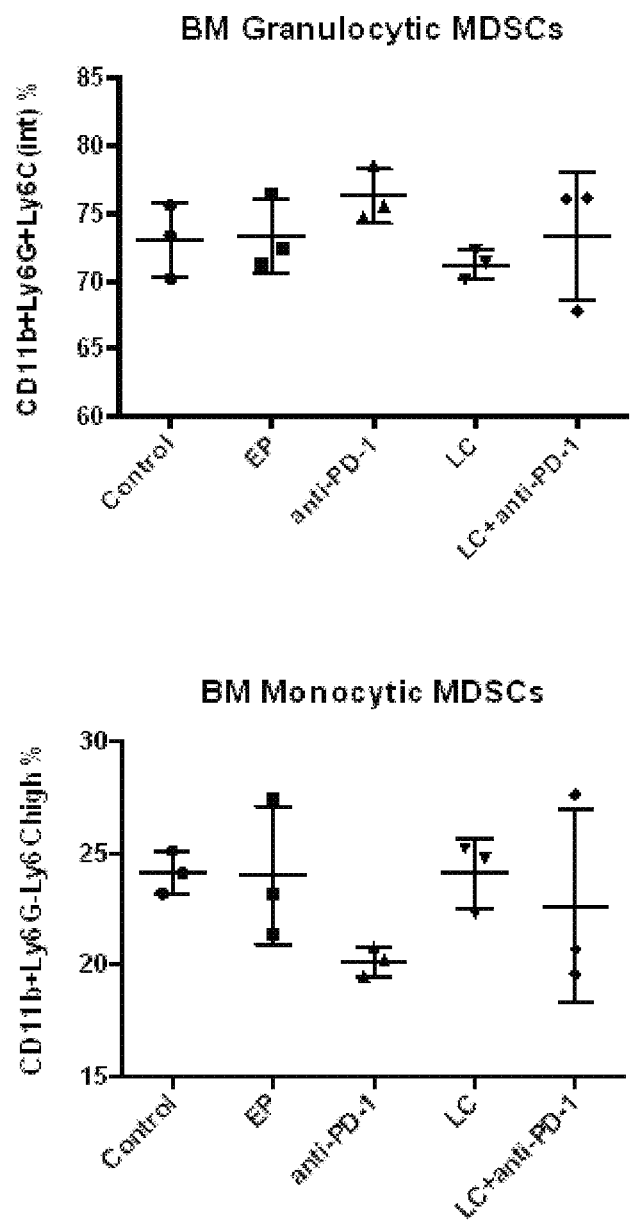
Figure 11:
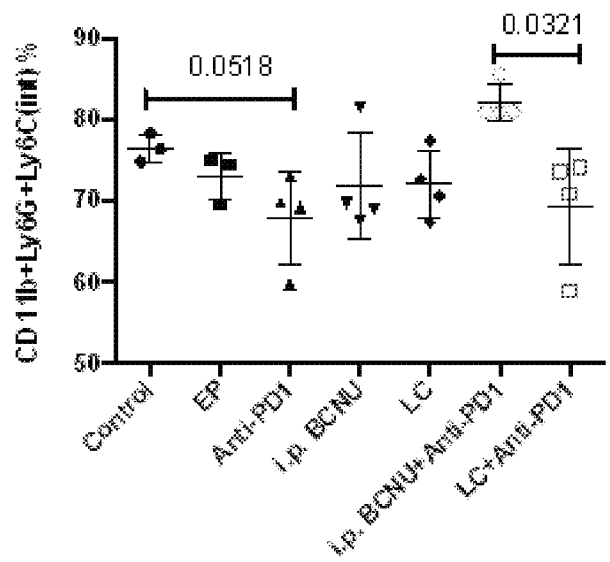
Figure 11:
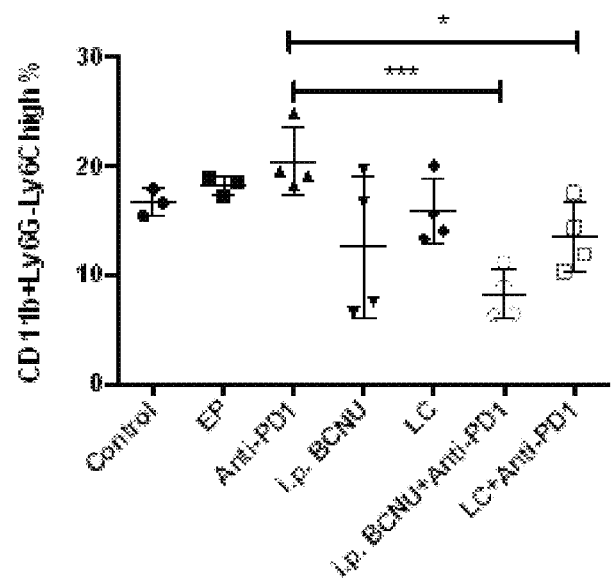
Figure 12:
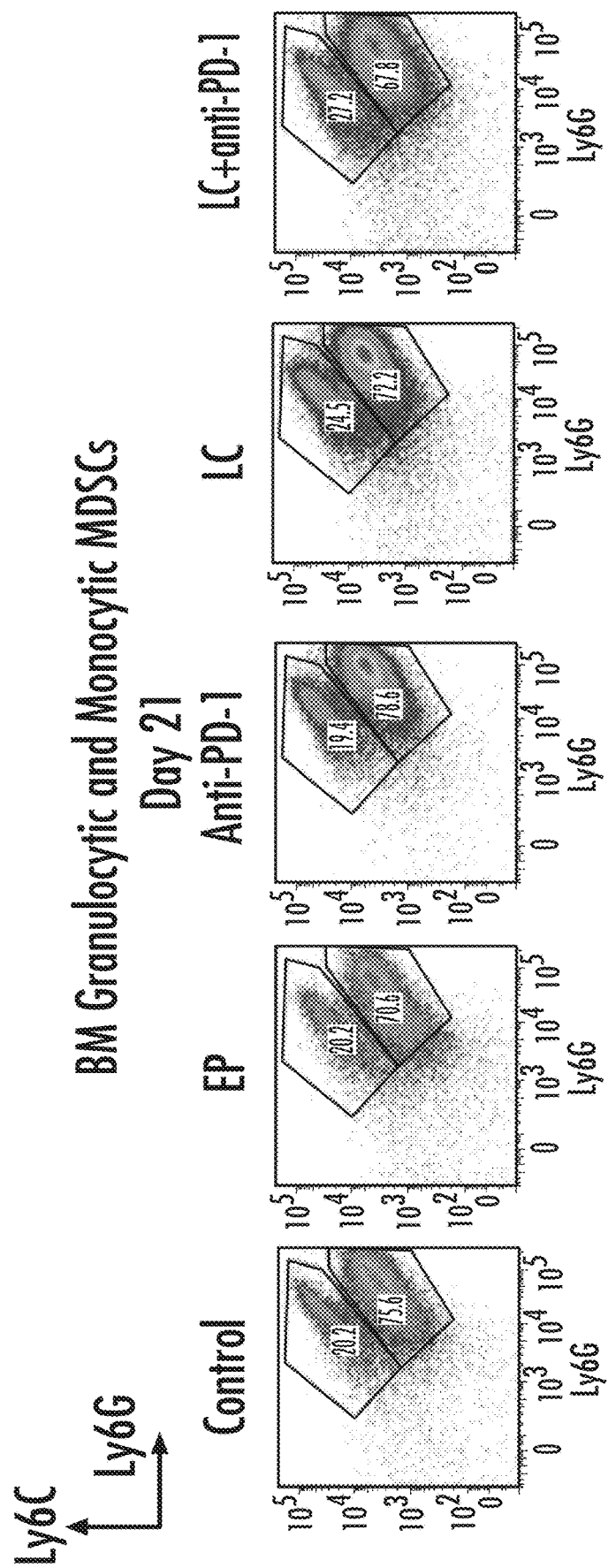
Figure 12:
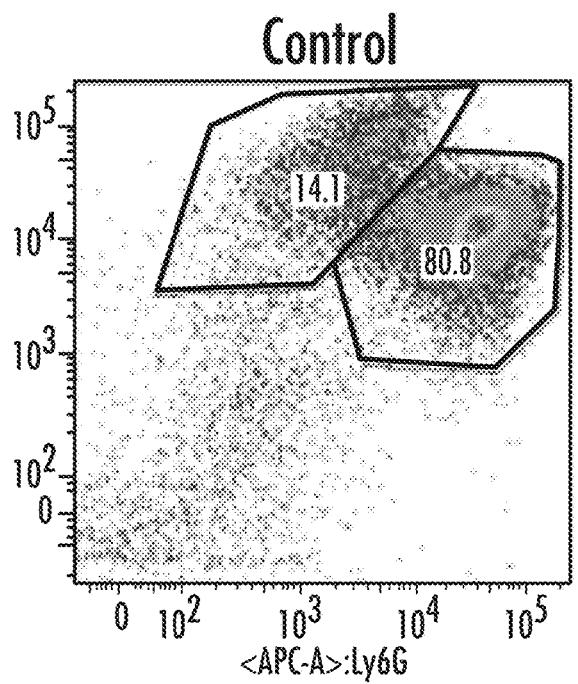
Figure 12:
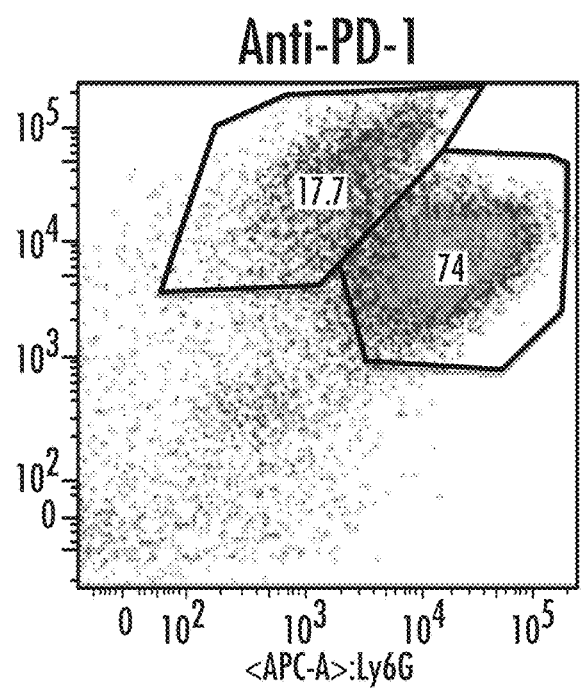
Figure 12:
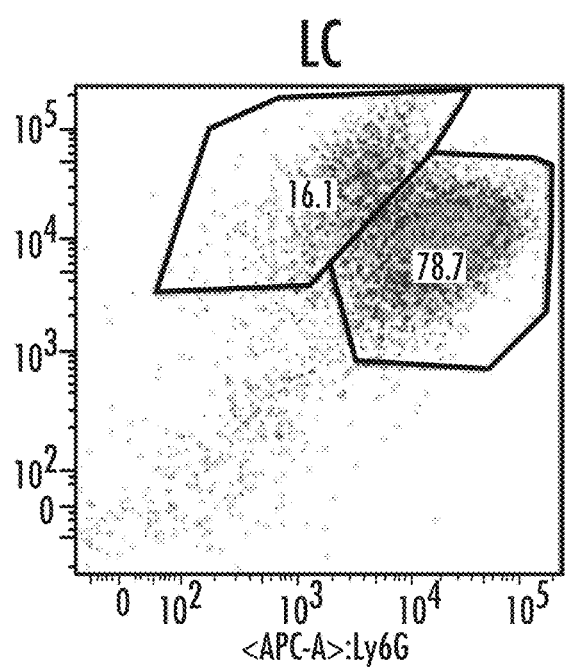
Figure 12:
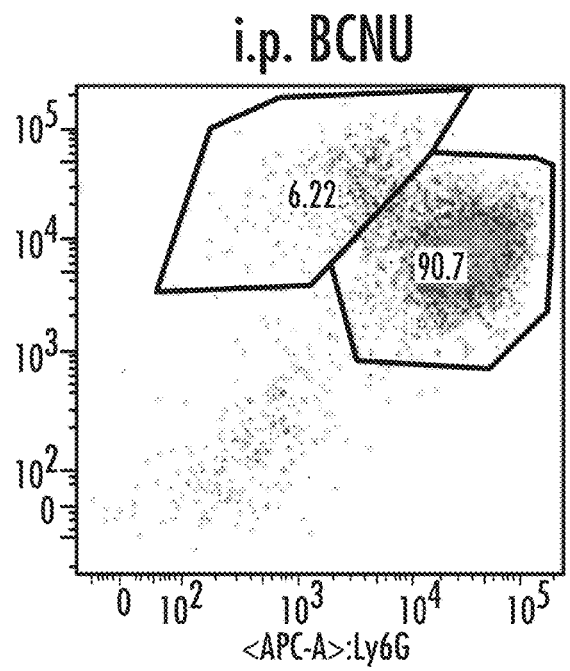
Figure 12:
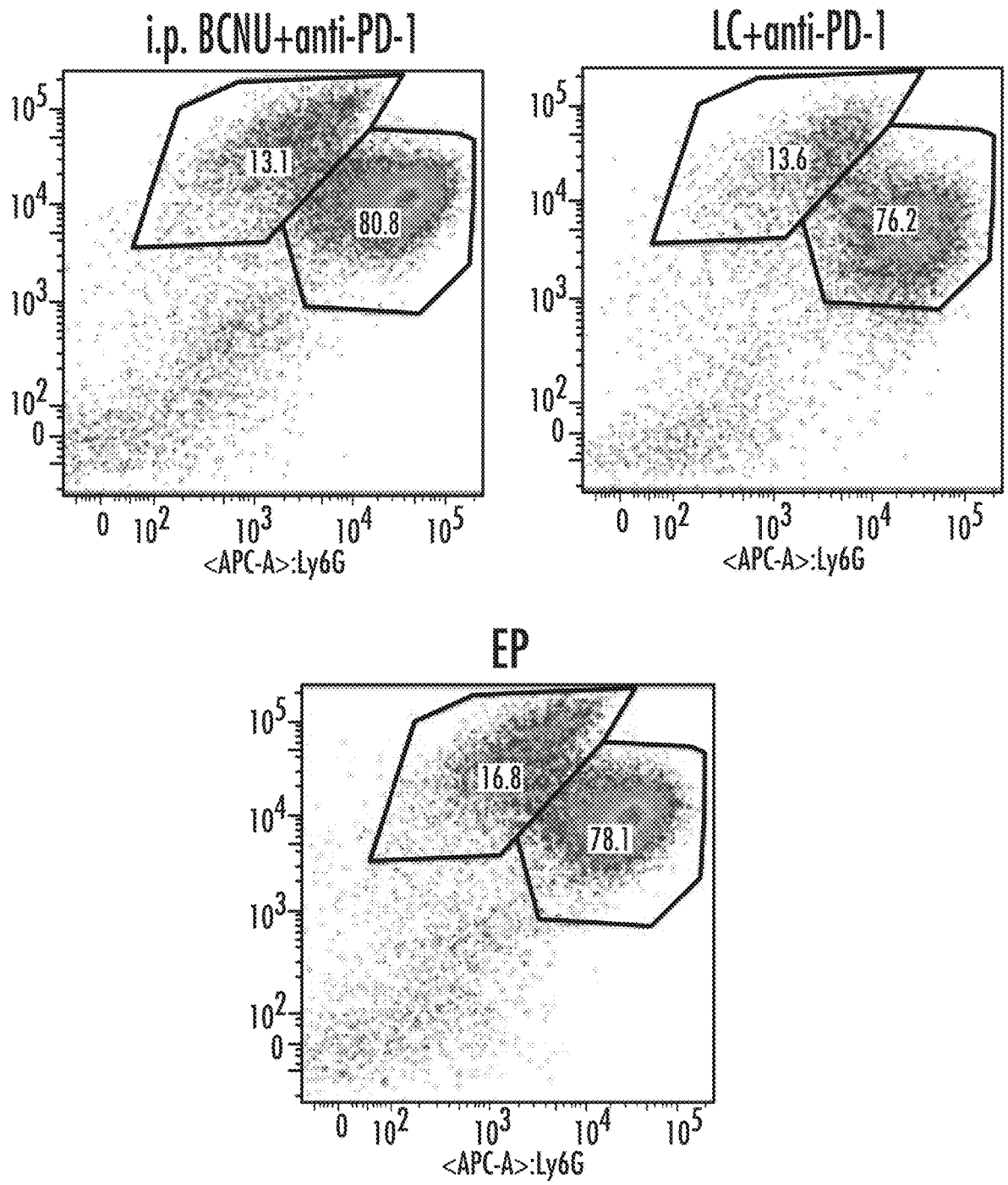
Figure 13:
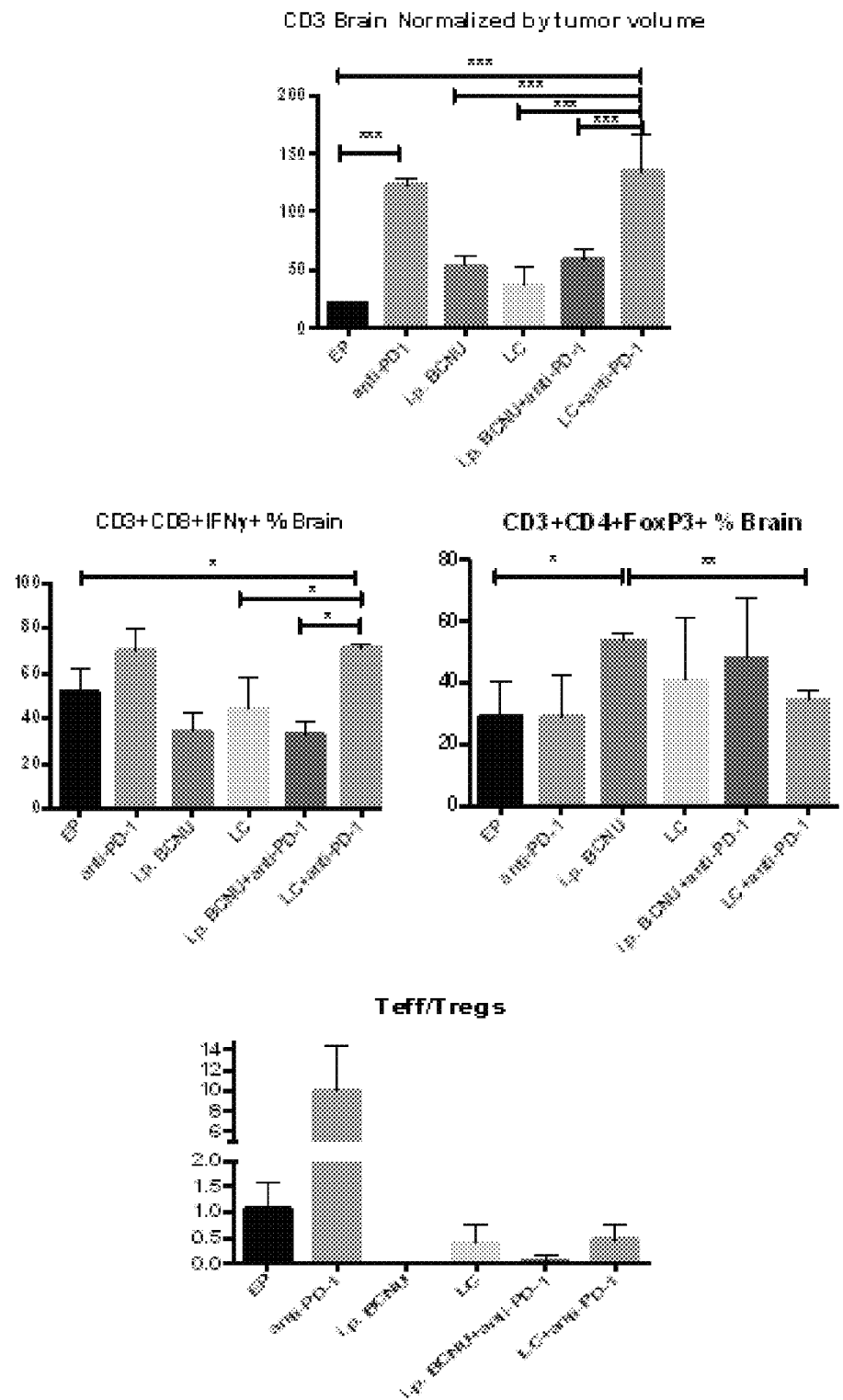
Figure 13:
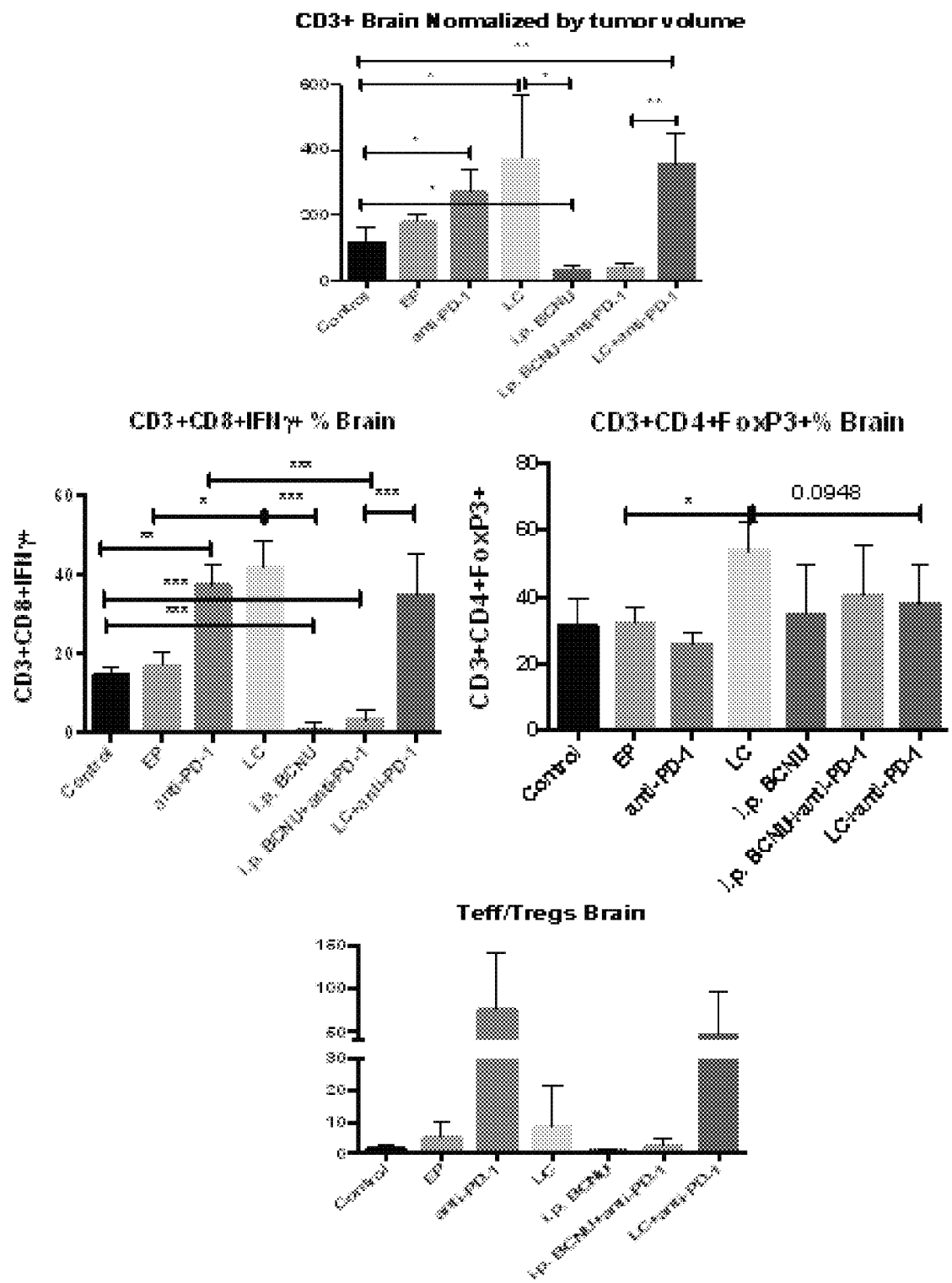
Figure 14:
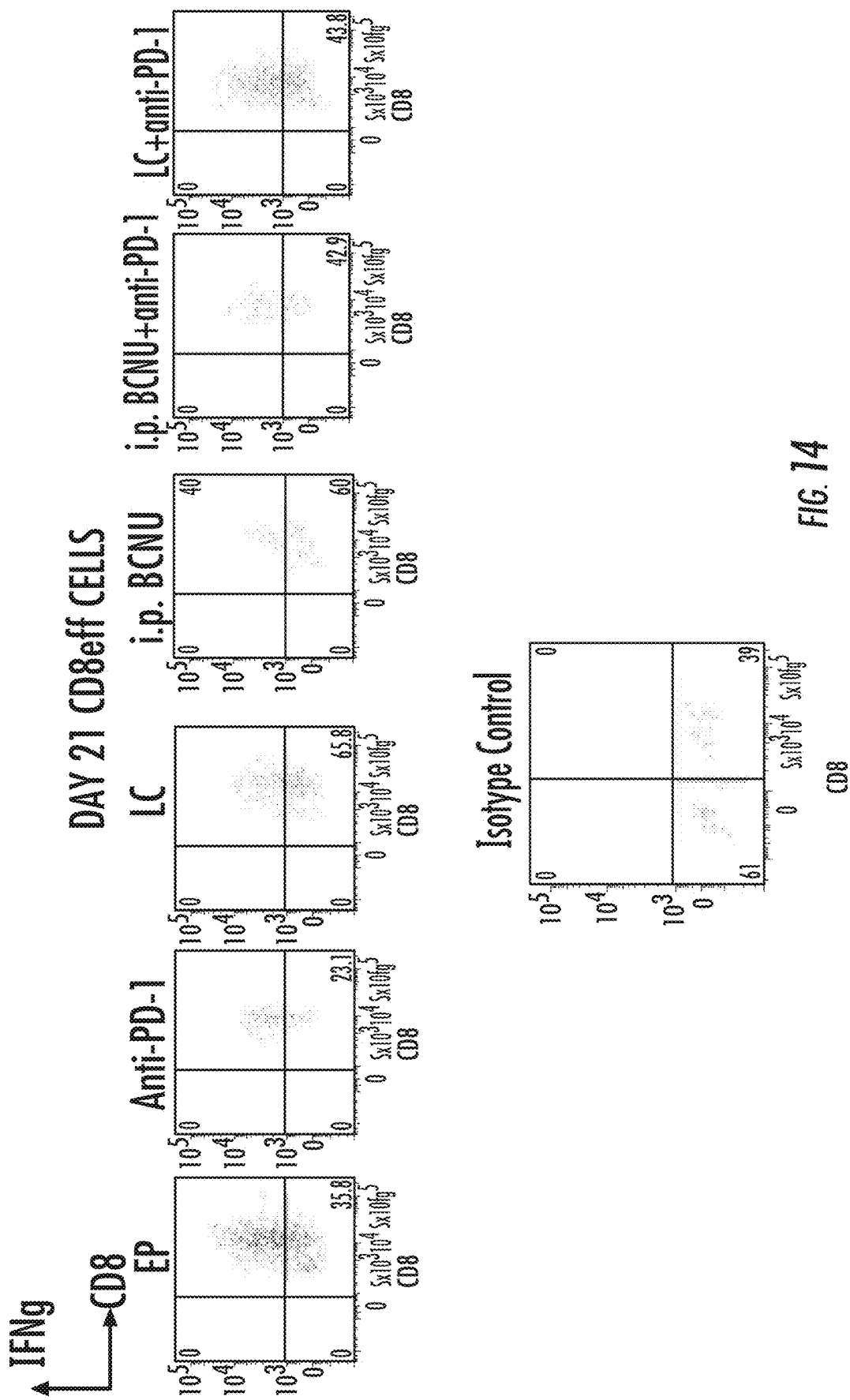
Figure 14:
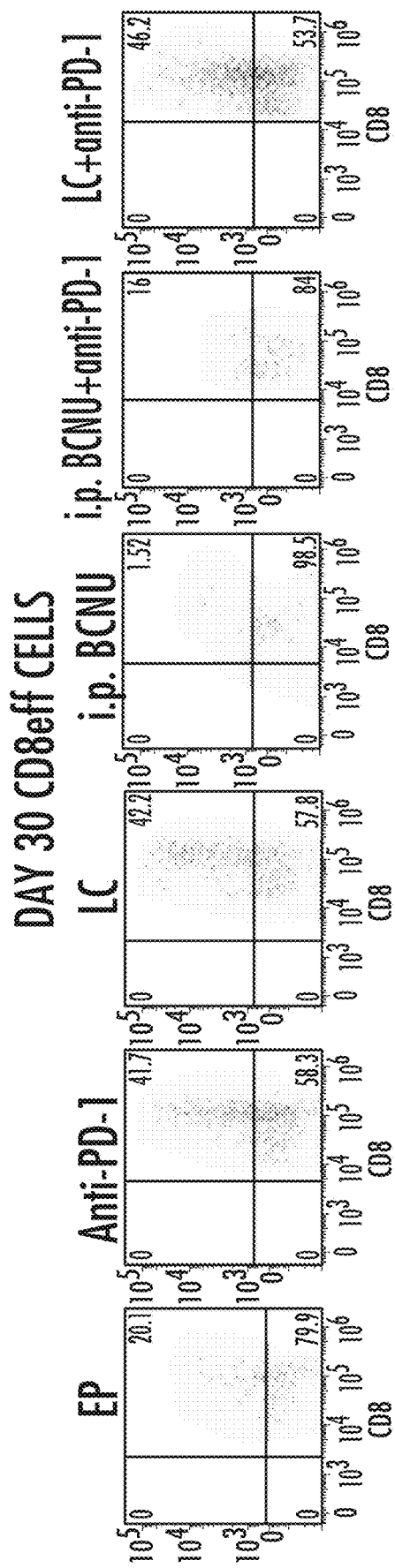
Figure 14:
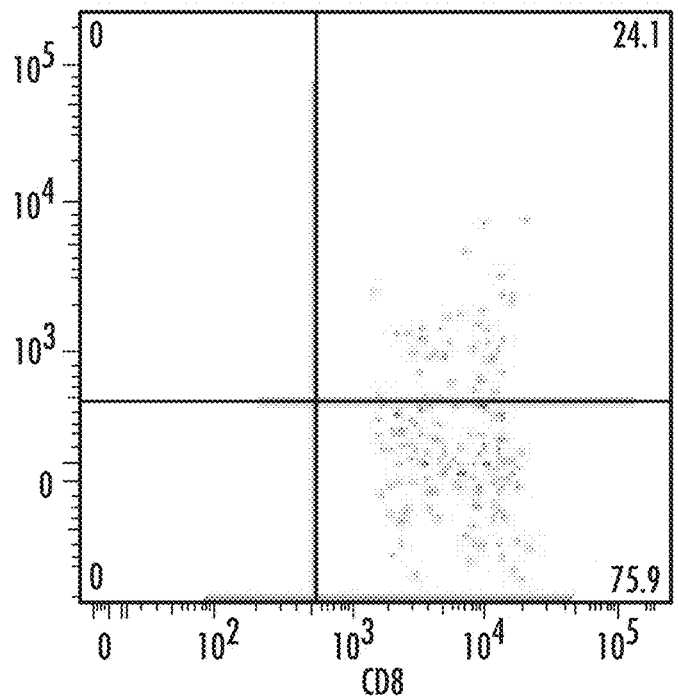
Figure 14:
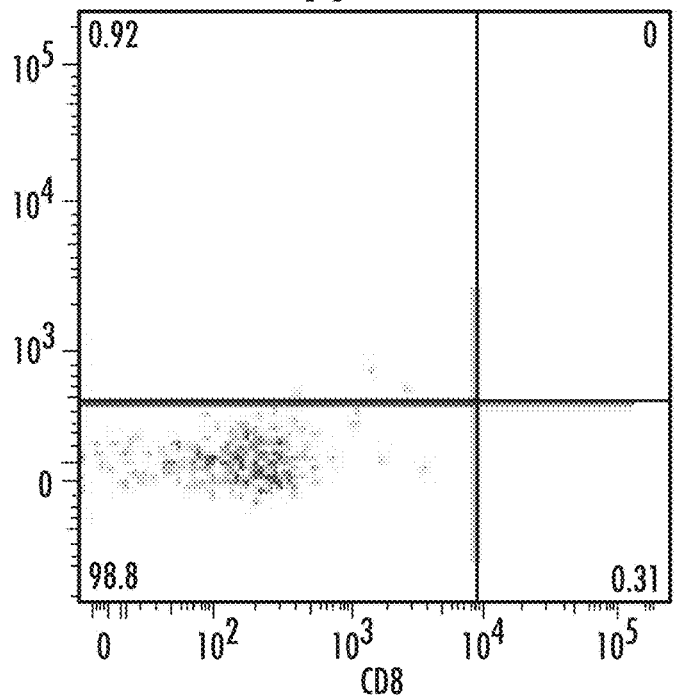
Figure 15:
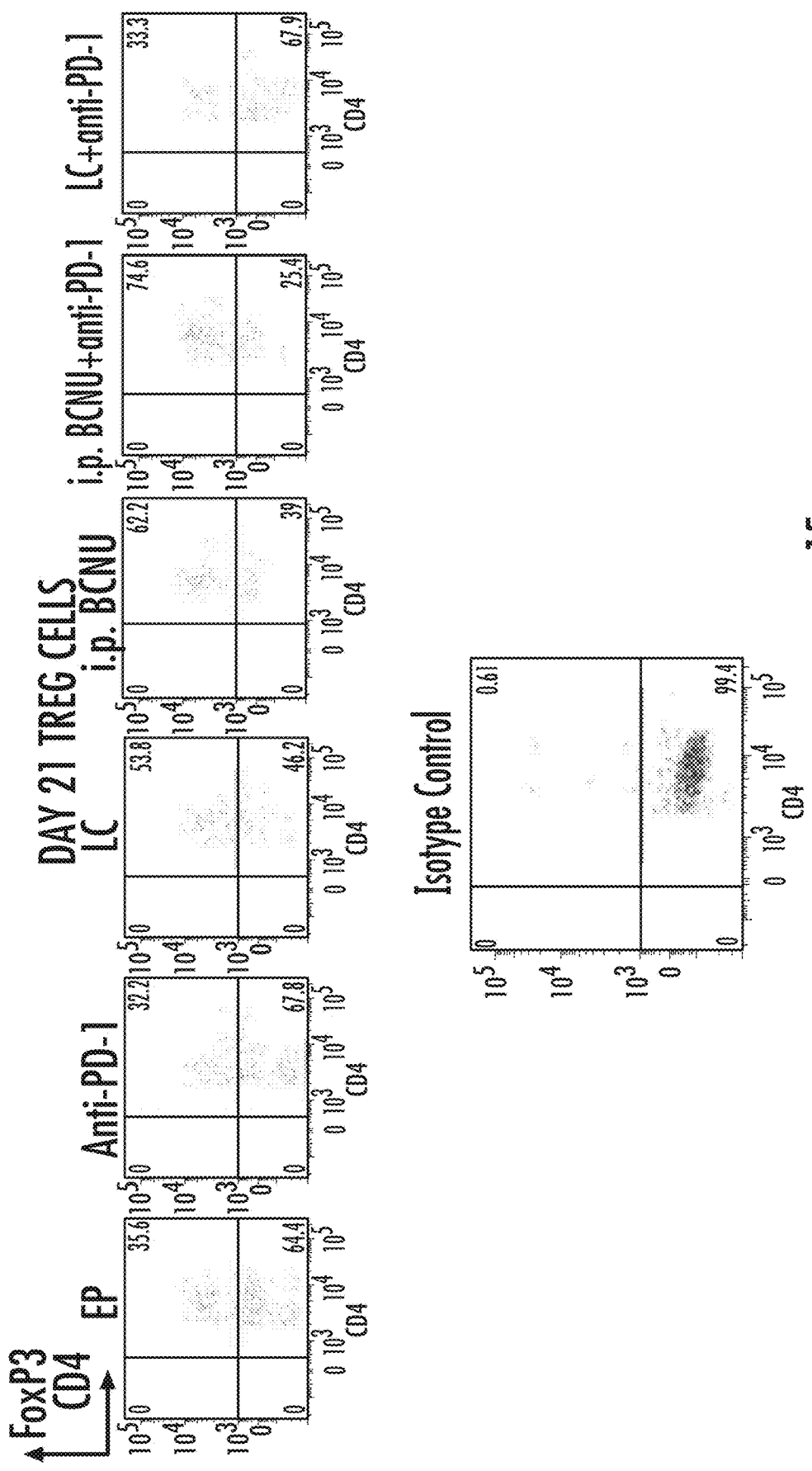
Figure 15:
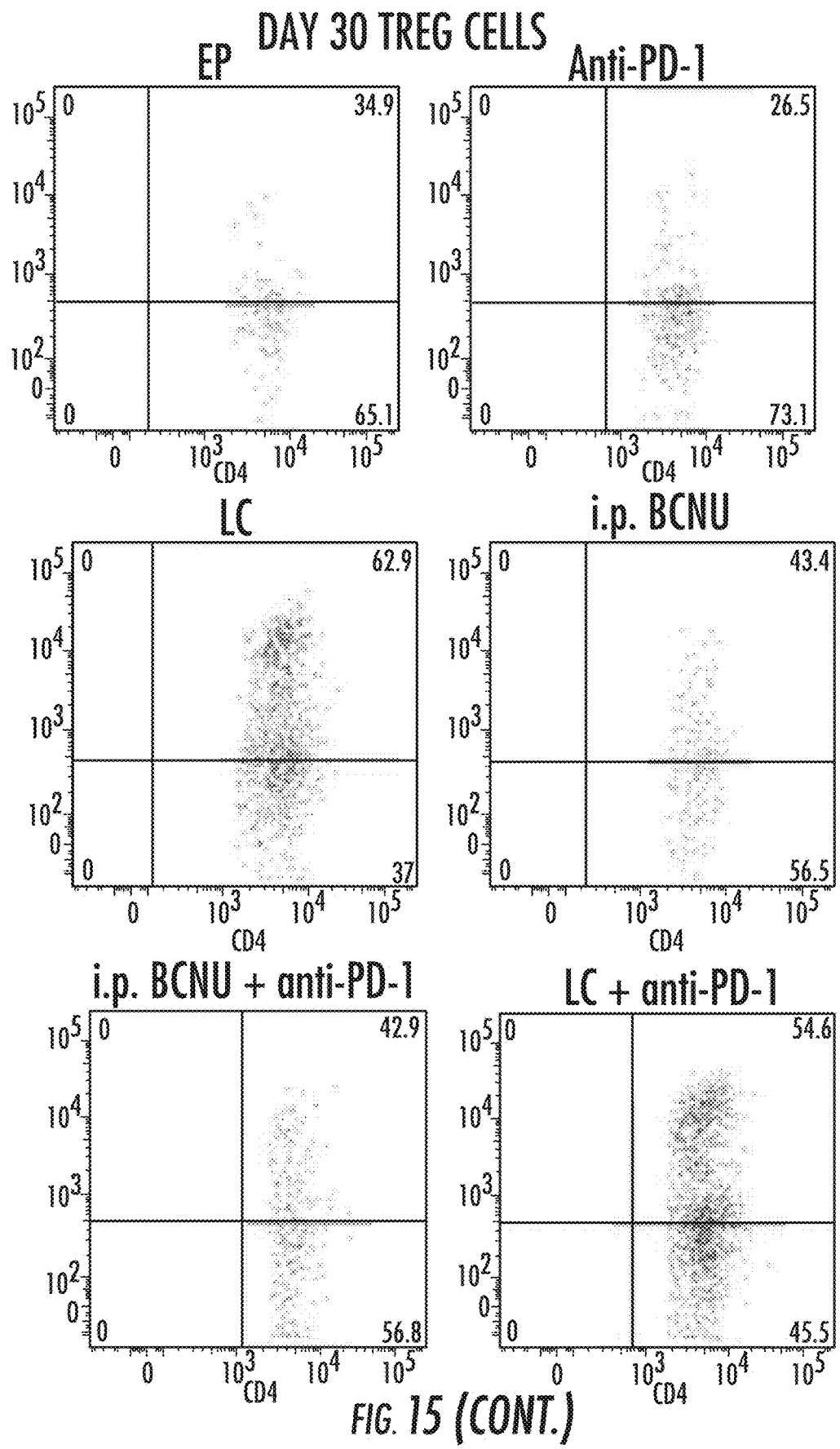
Figure 15:
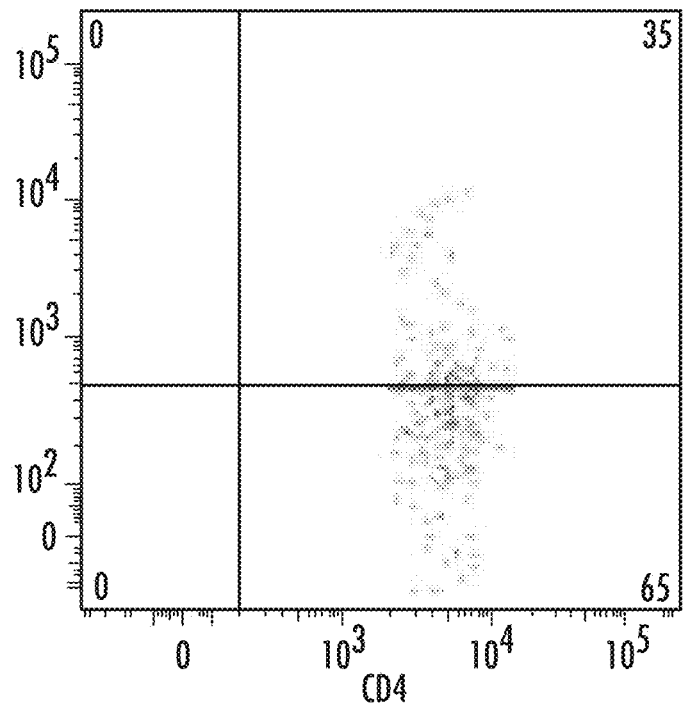
Figure 15:
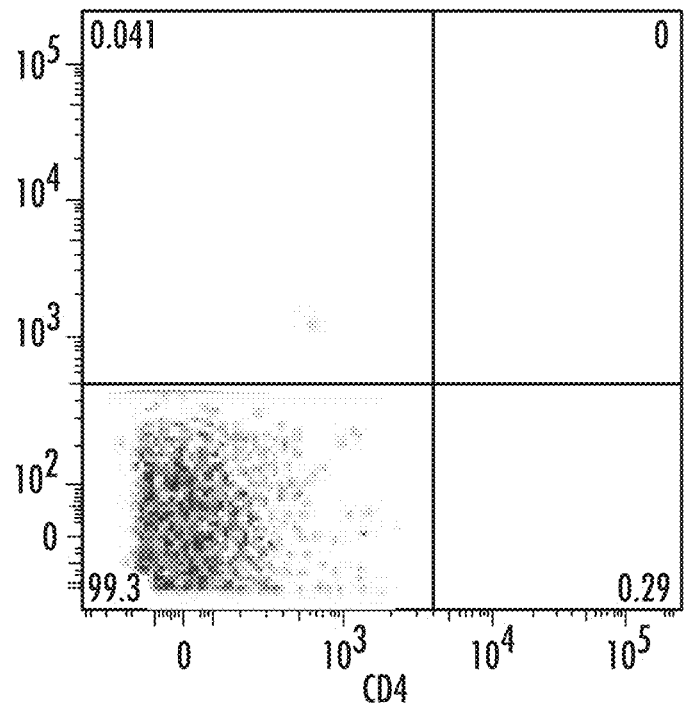
Figure 16:
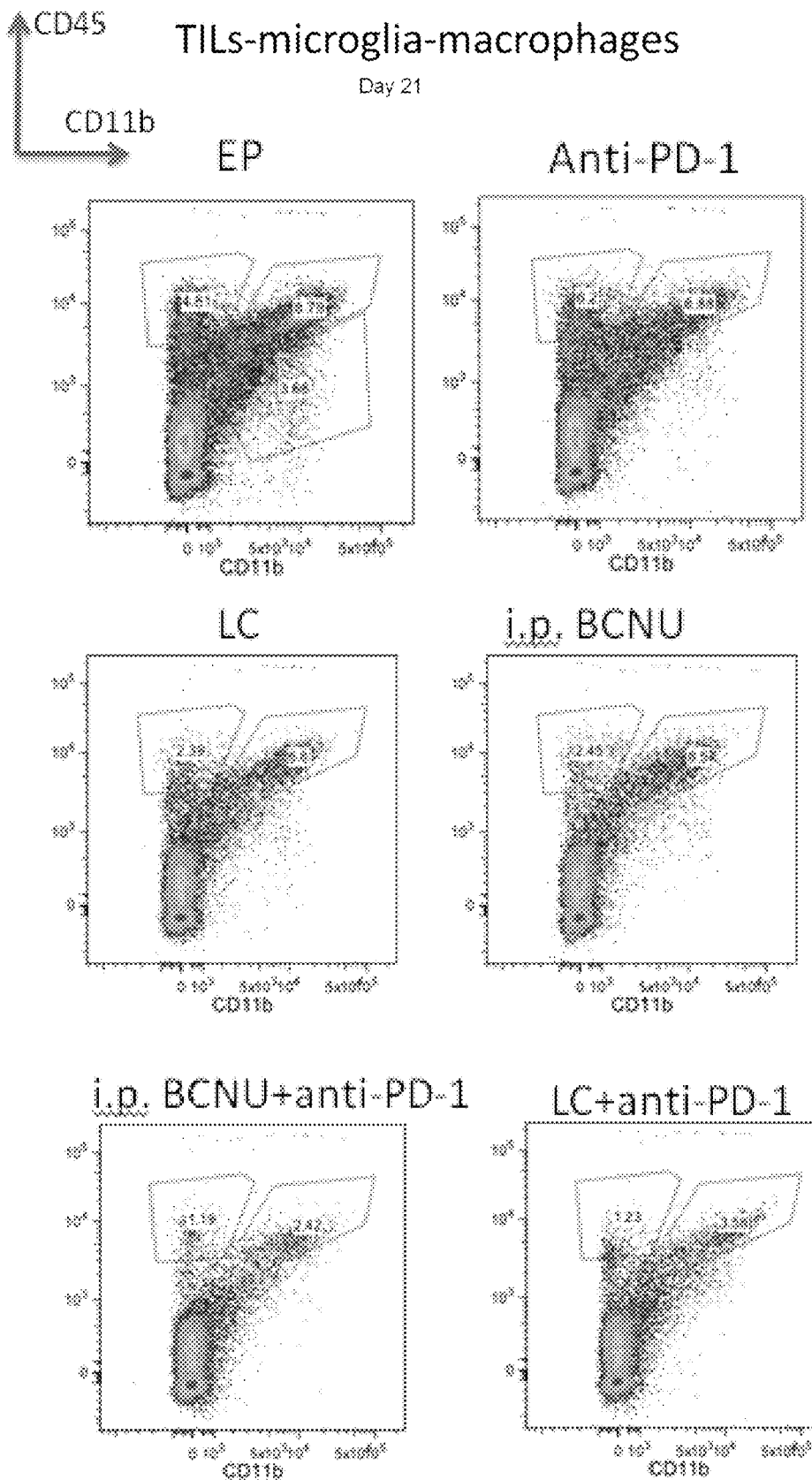
Figure 16:
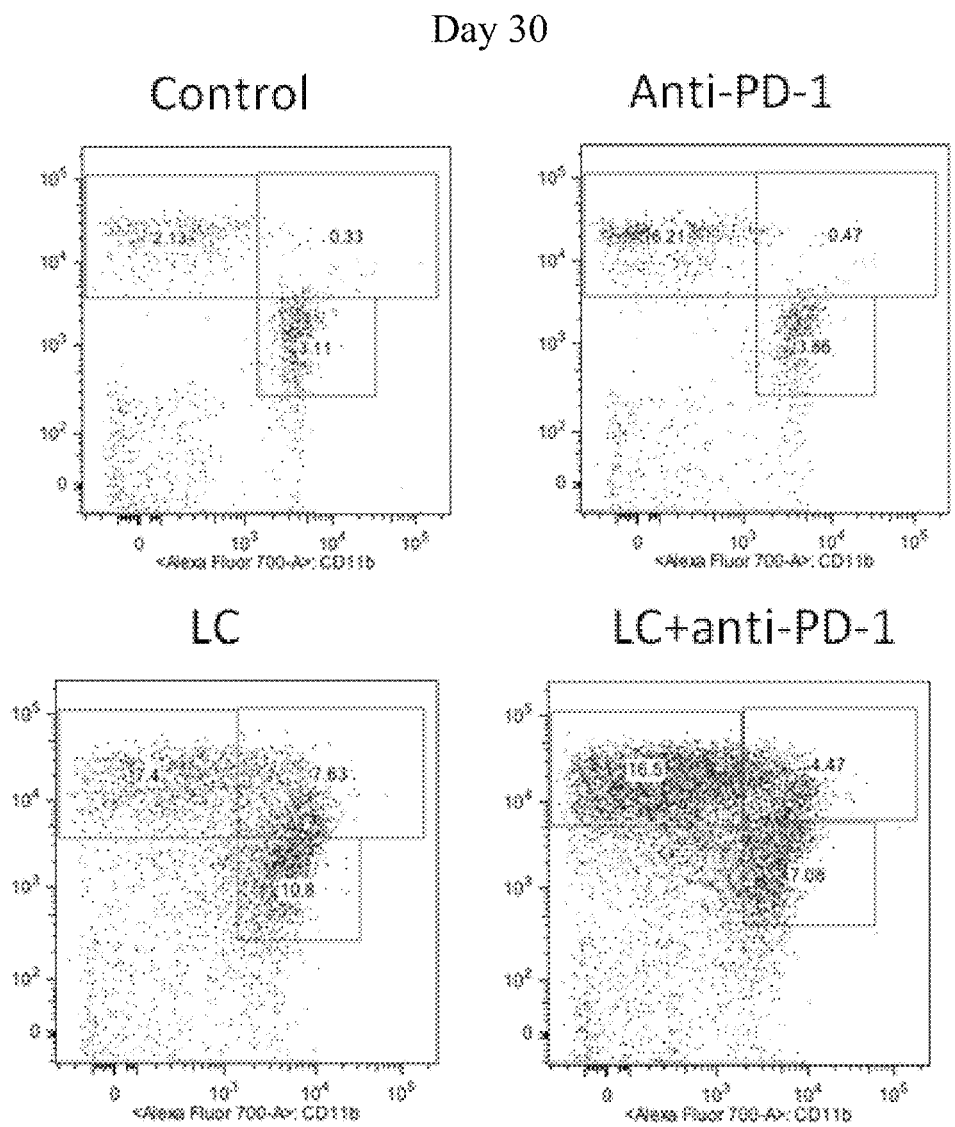
Figure 17:
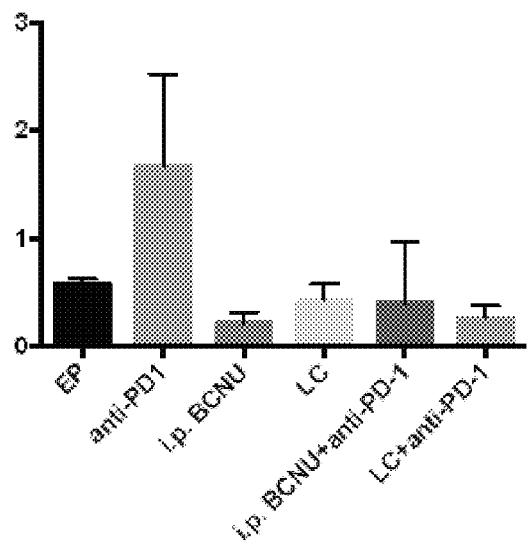
Figure 17:
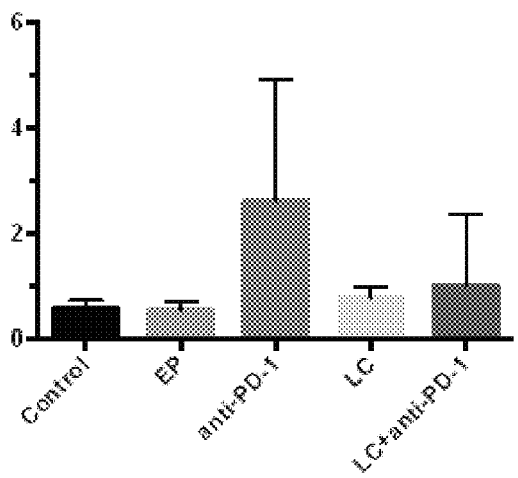
Figure 18:
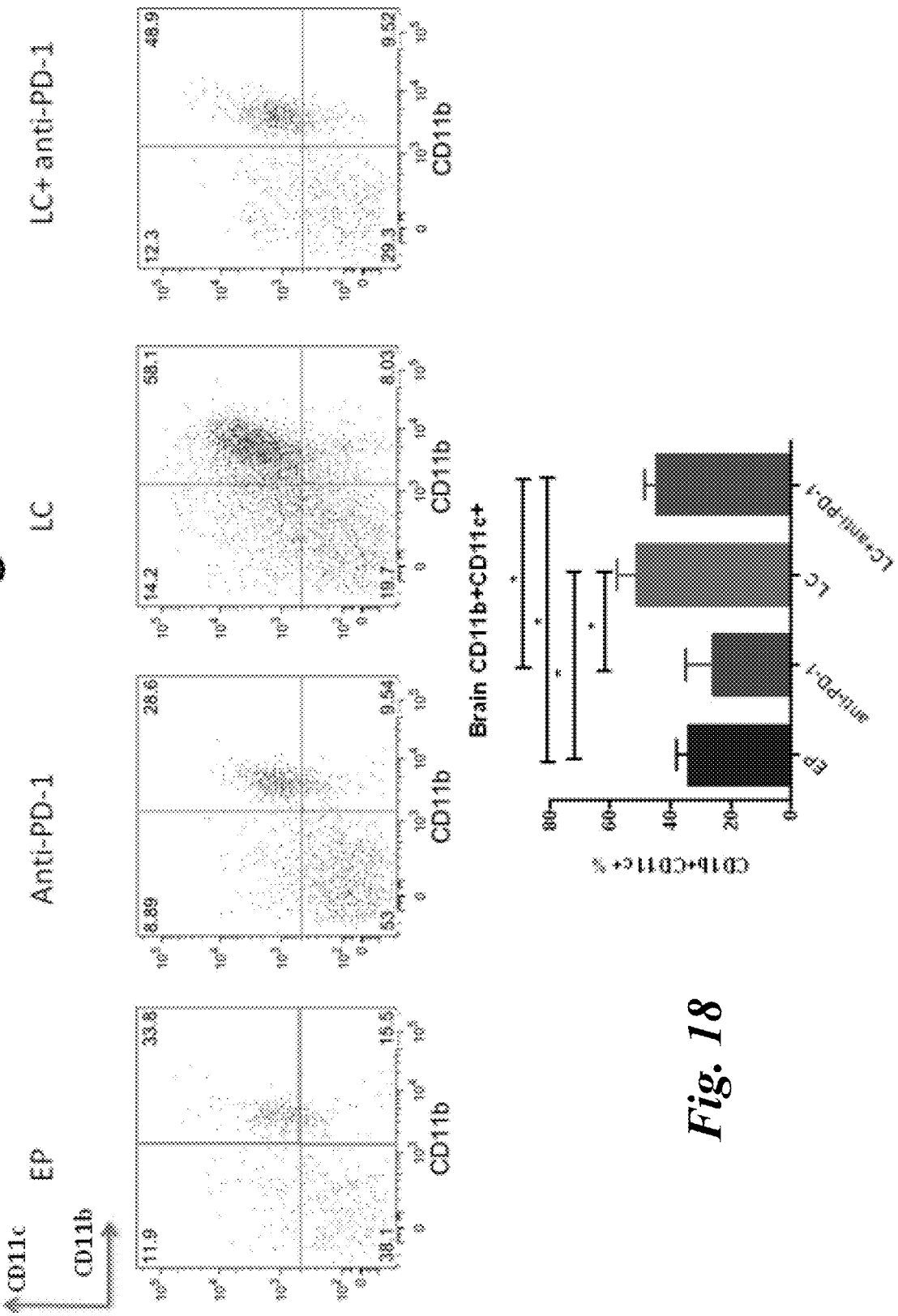
Figure 19:
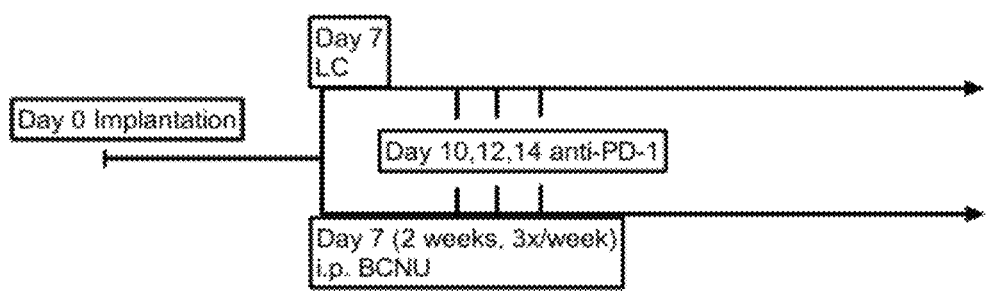
Figure 19:
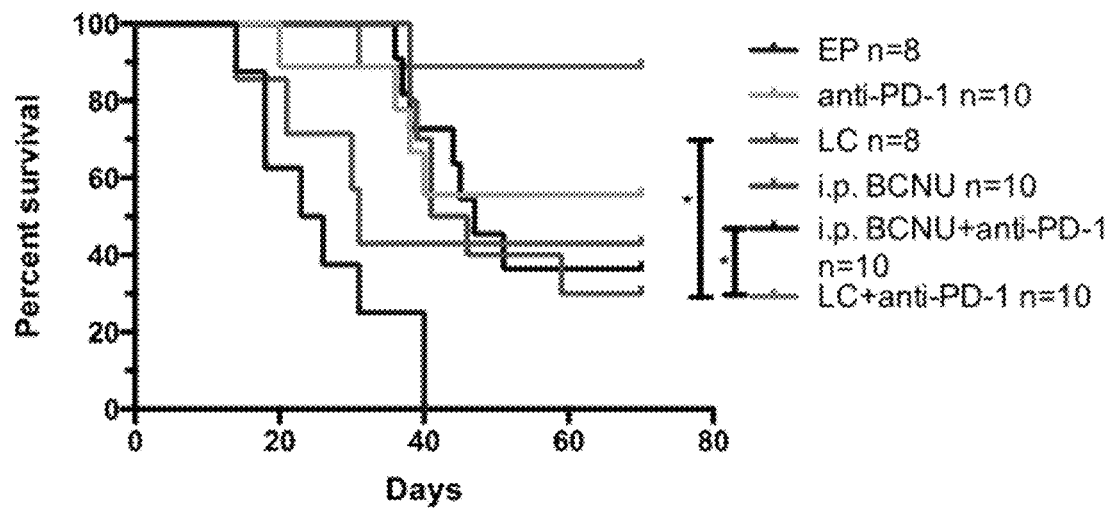
Figure 20:
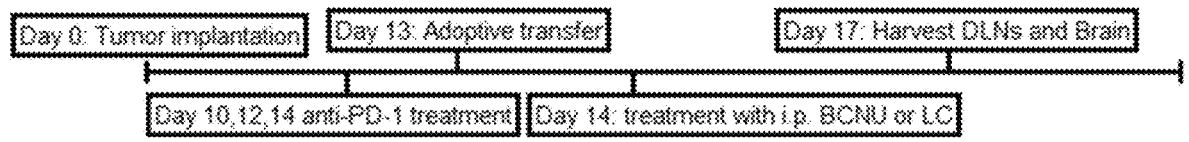
Figure 20:
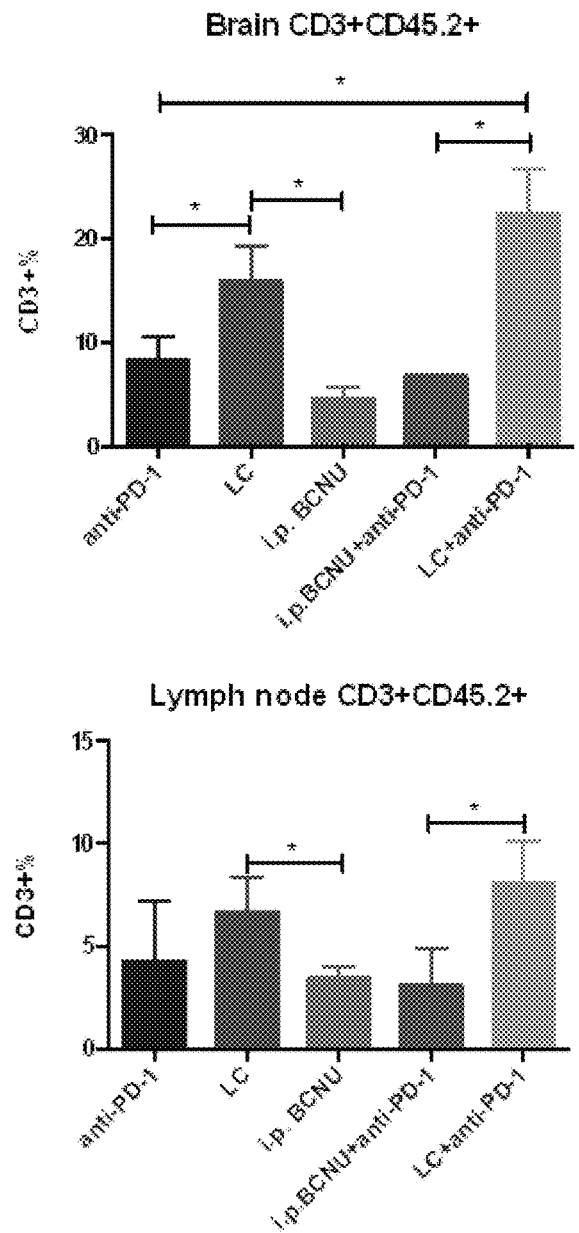
Figure 21:
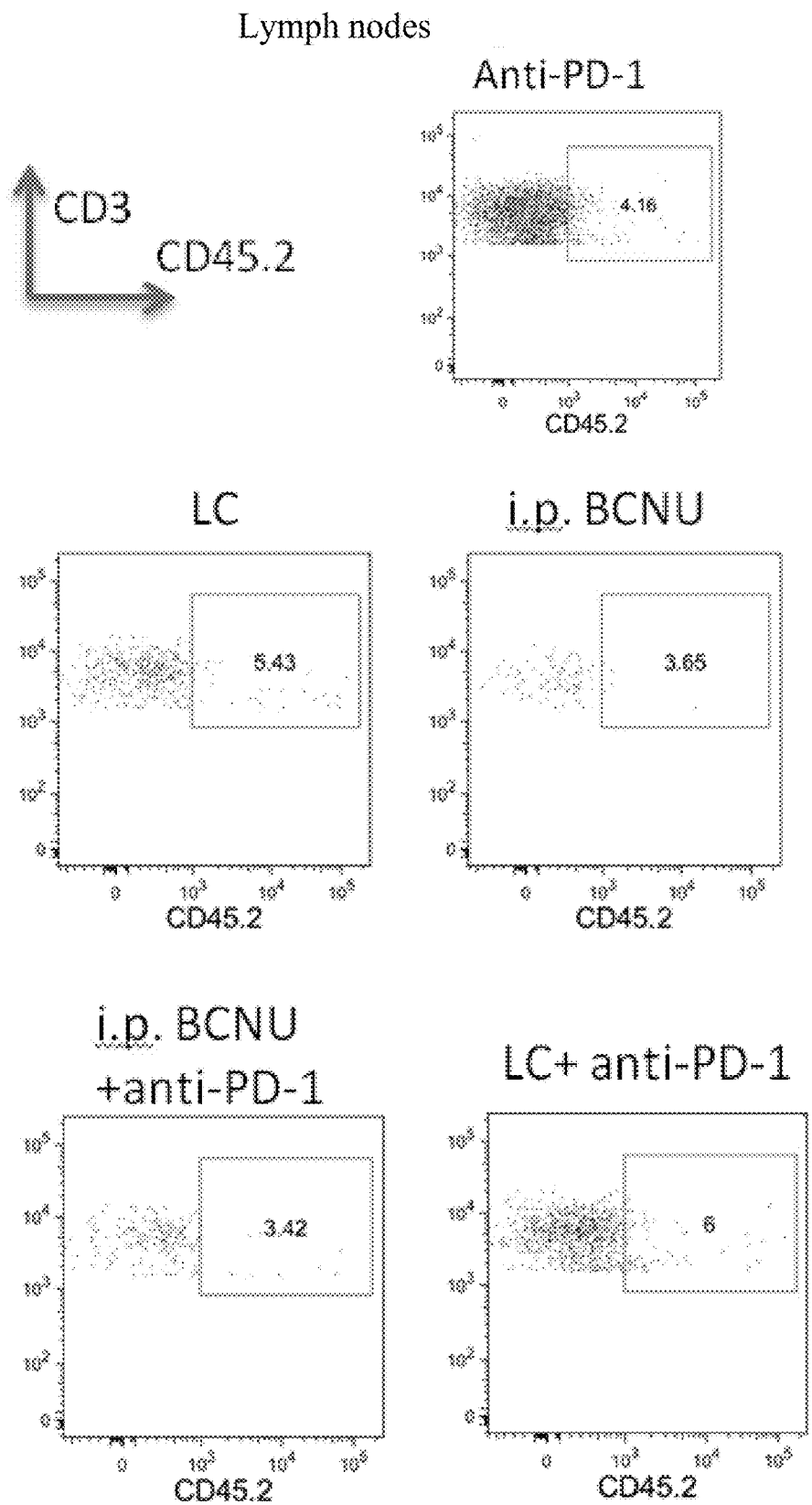
Figure 21:
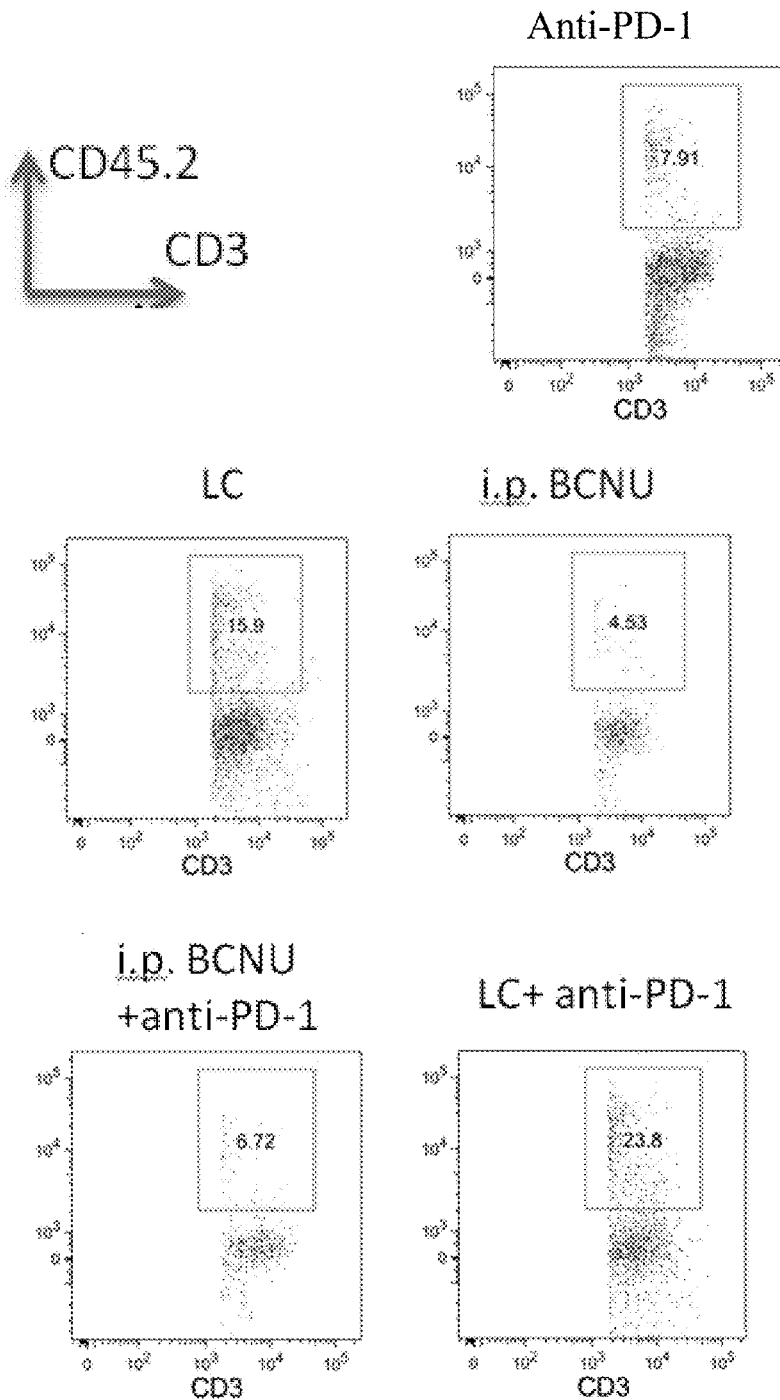
Figure 22:
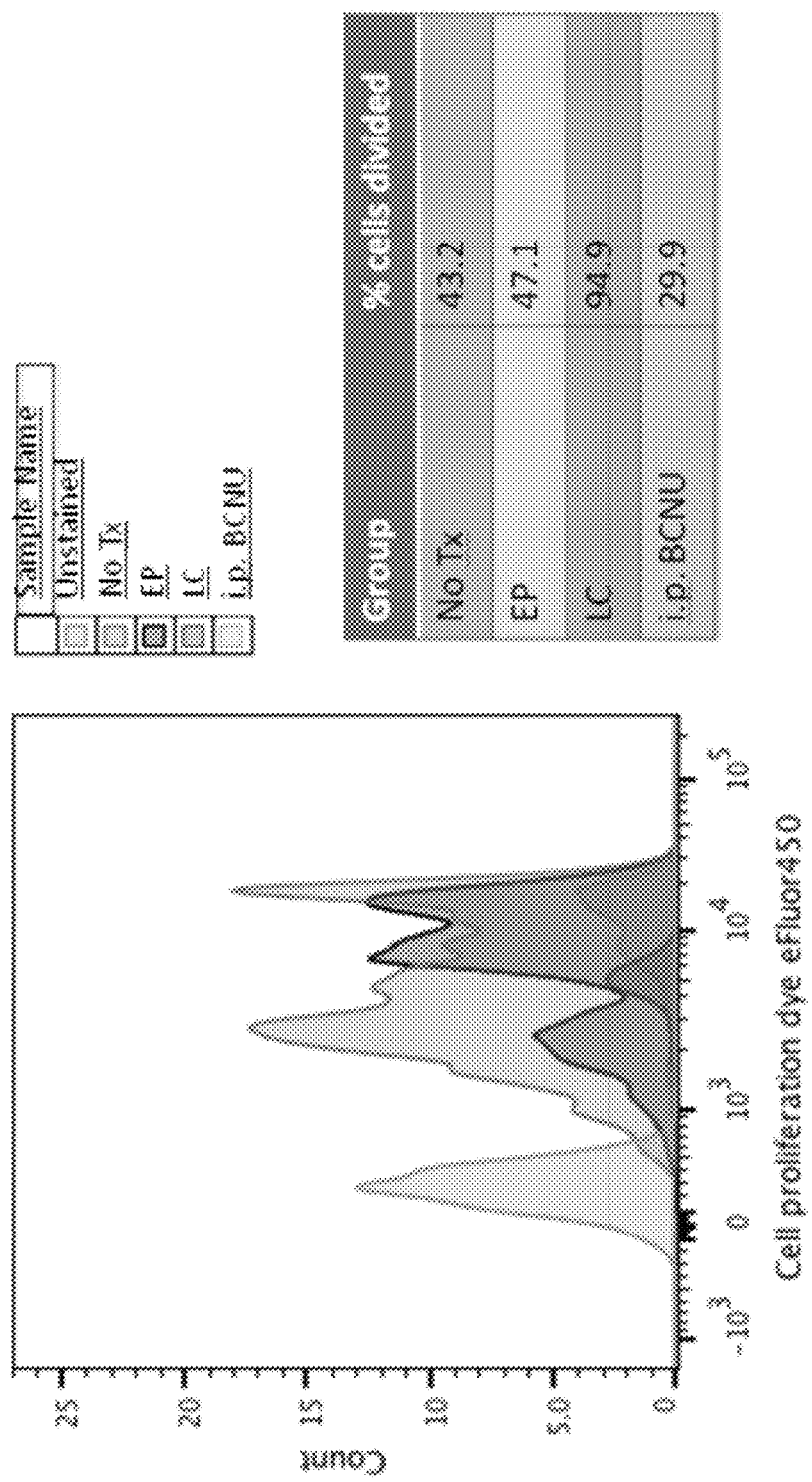
Figure 23:
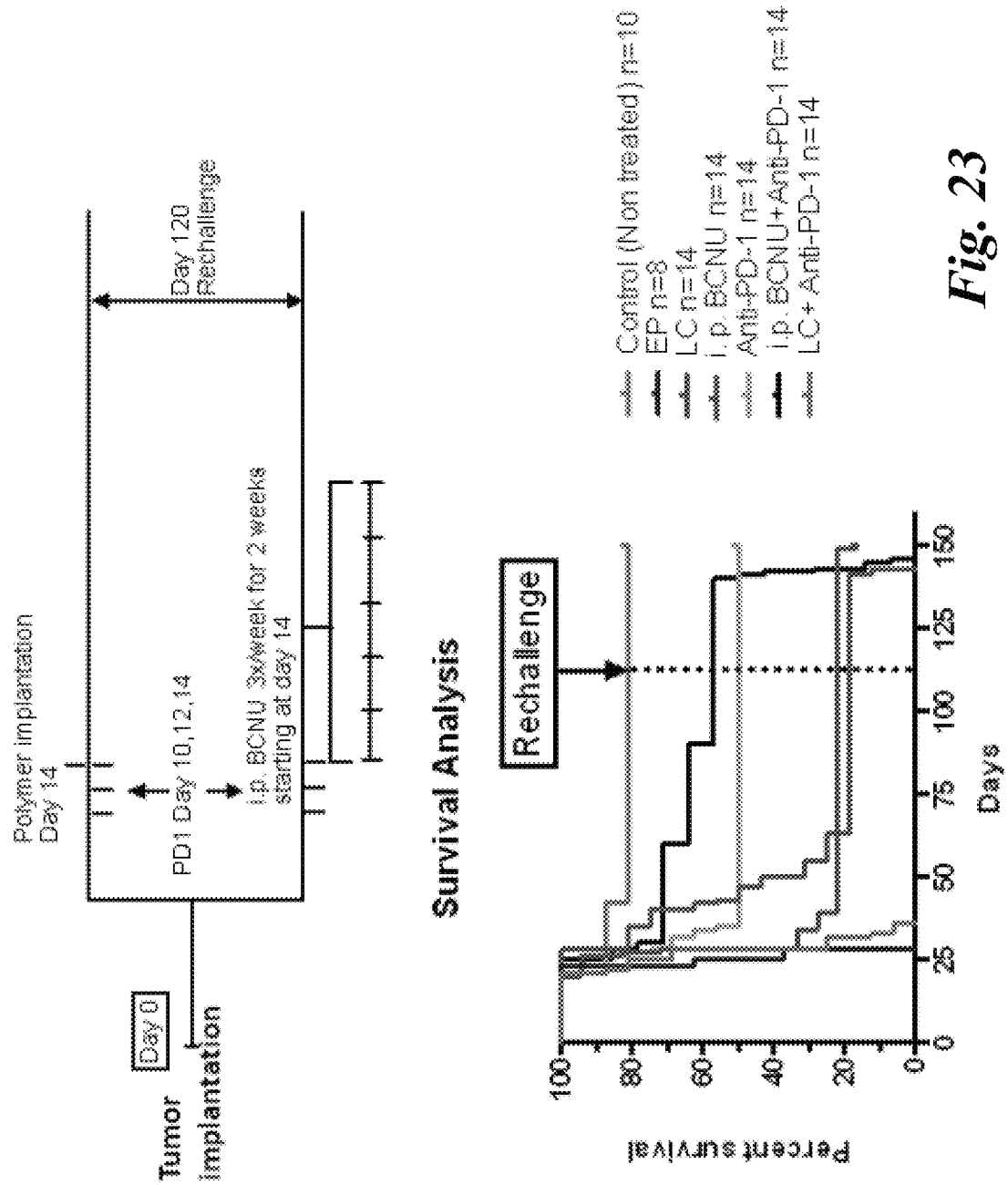
Figure 24:
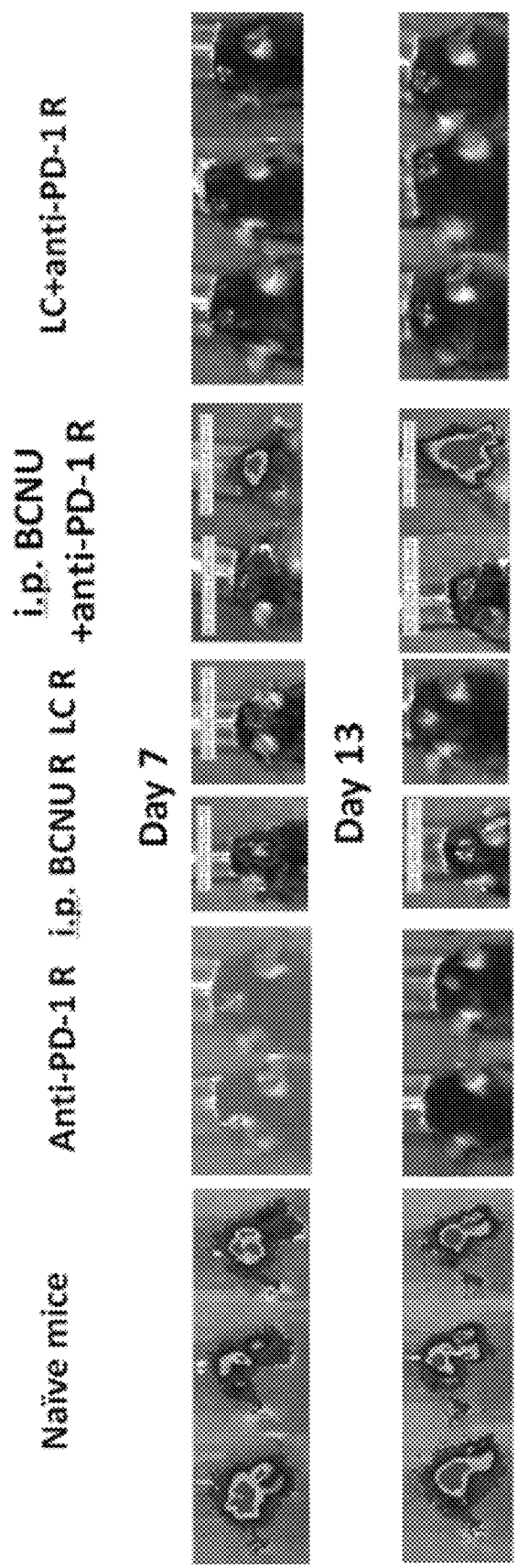
Figure 24:
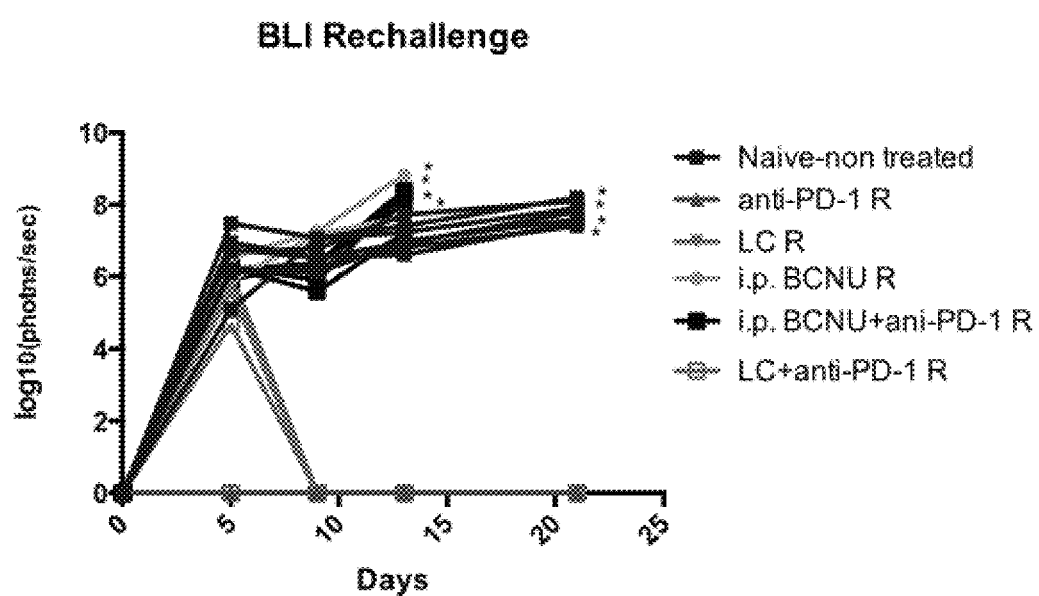
Figure 25:
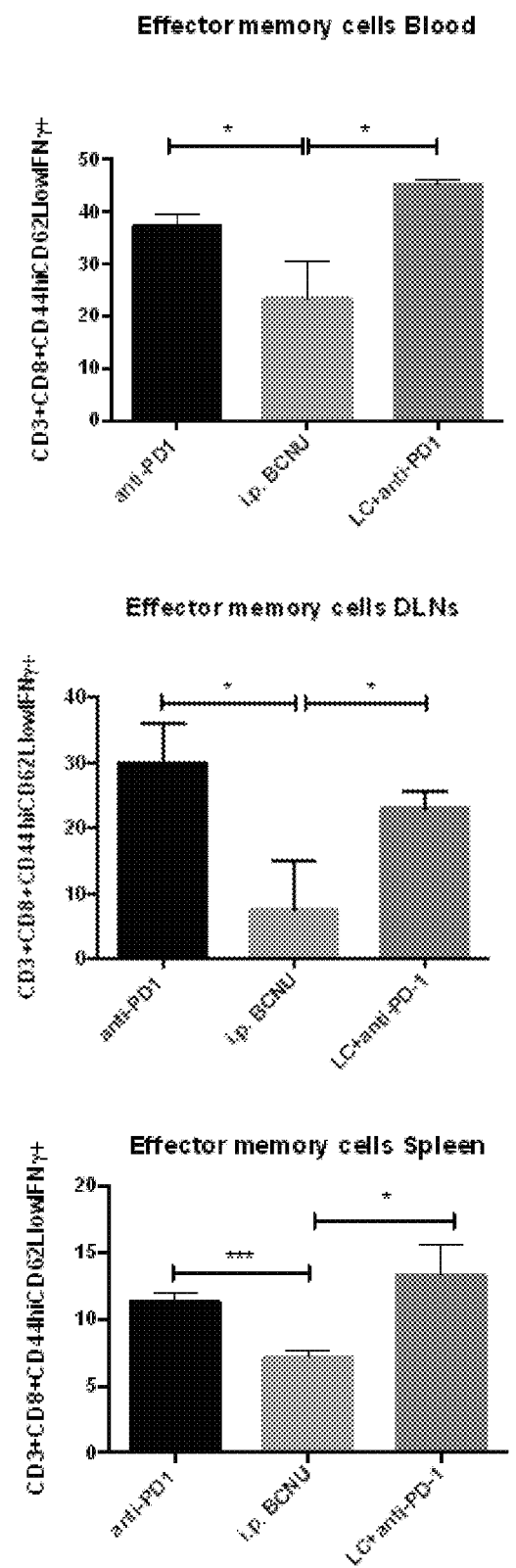
Figure 26:
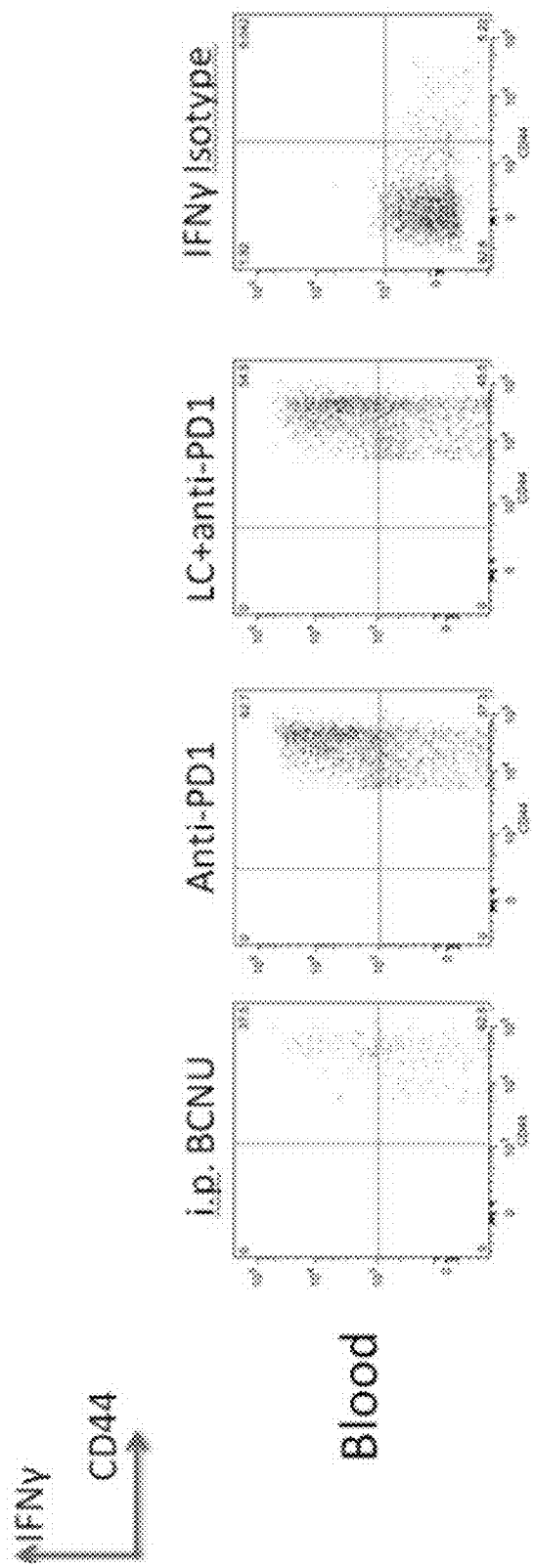
Figure 26:
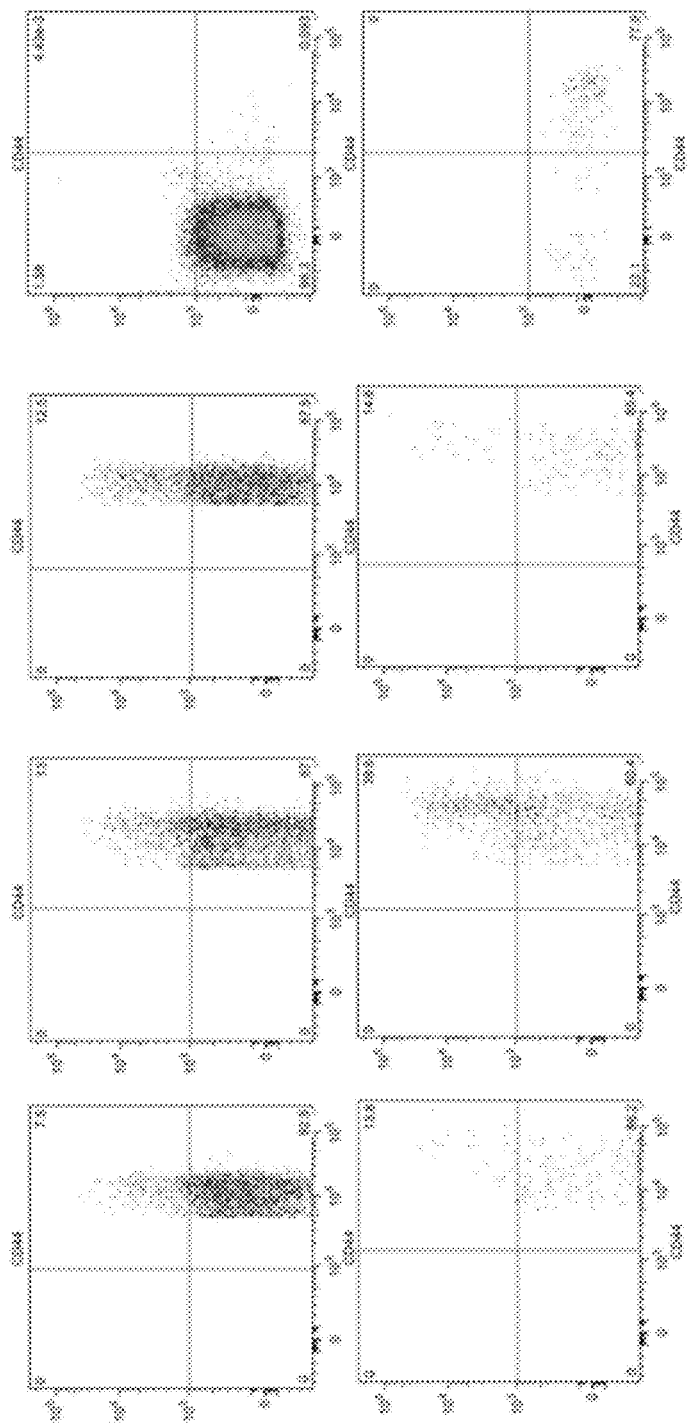
Figure 27:
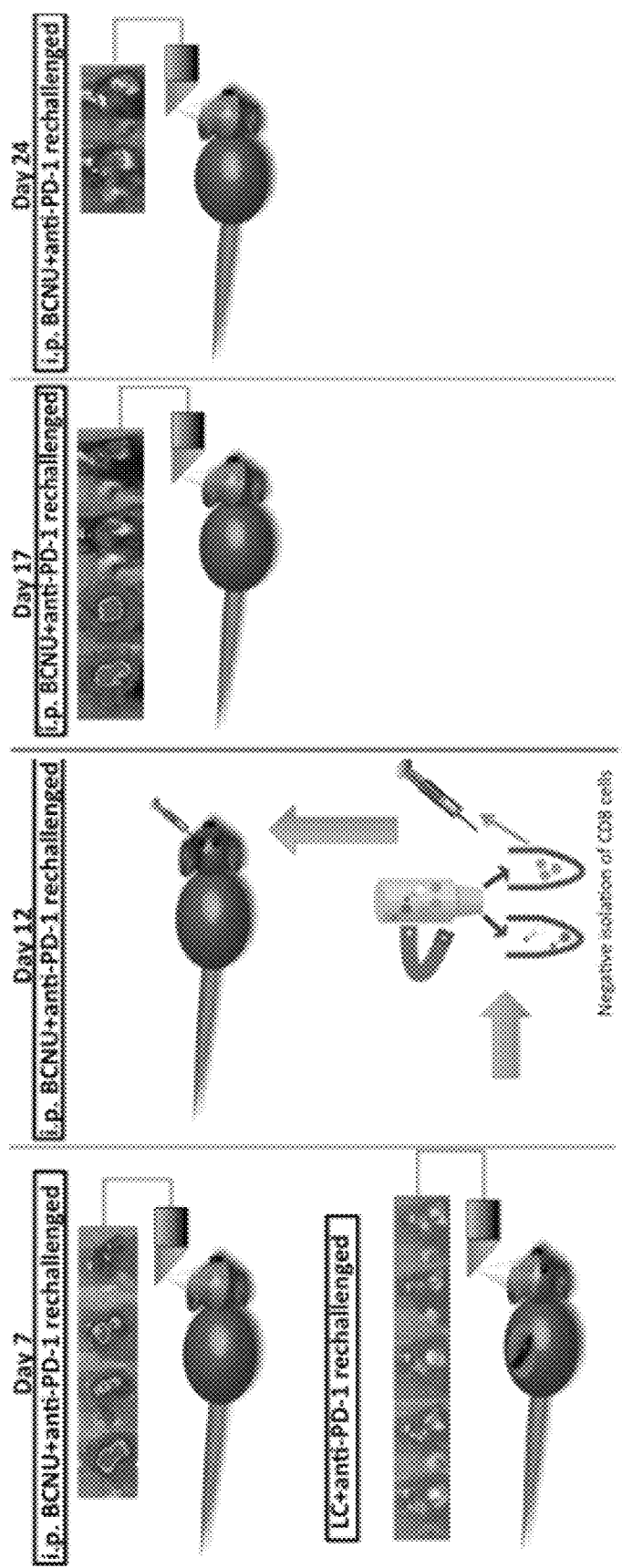
Figure 28:
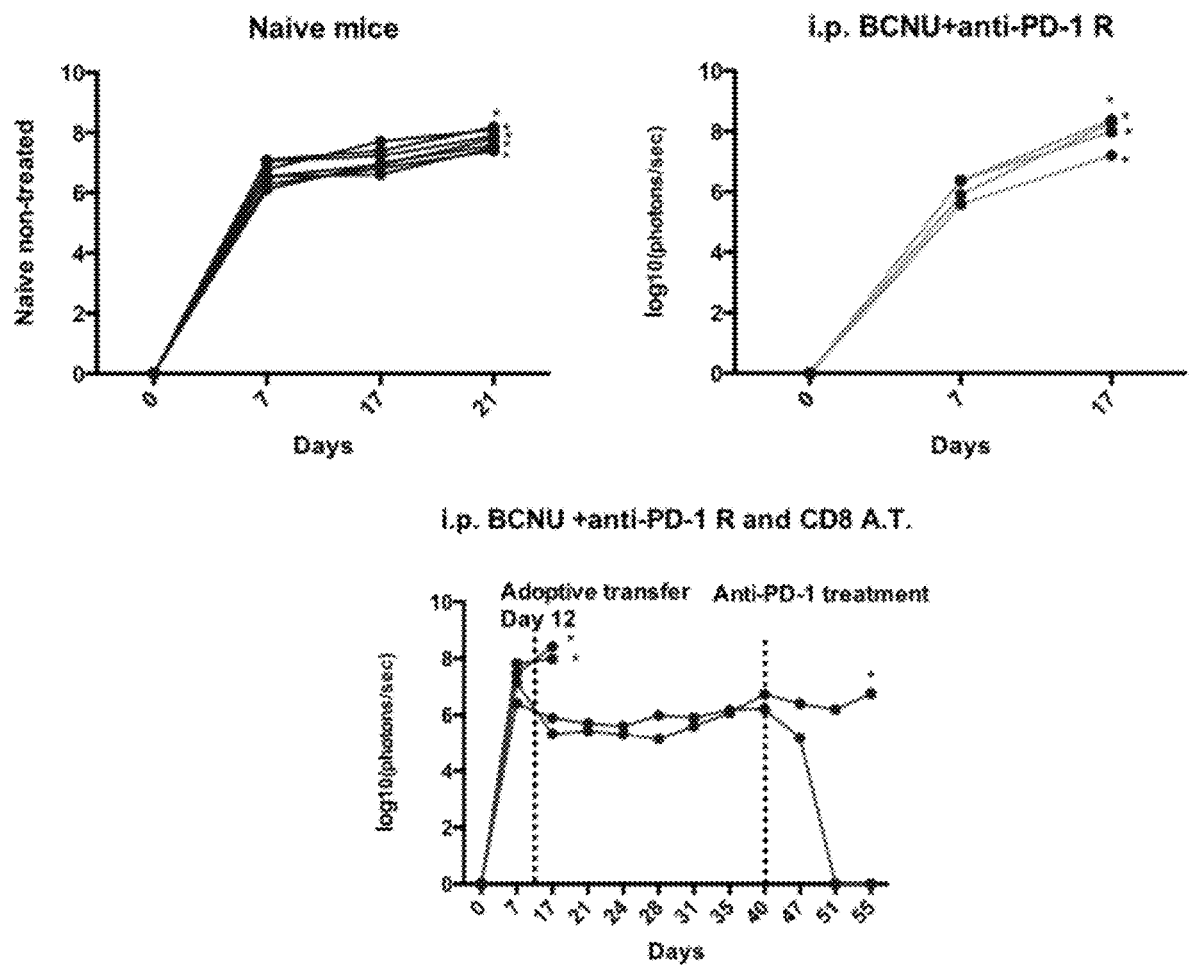
Figure 29:
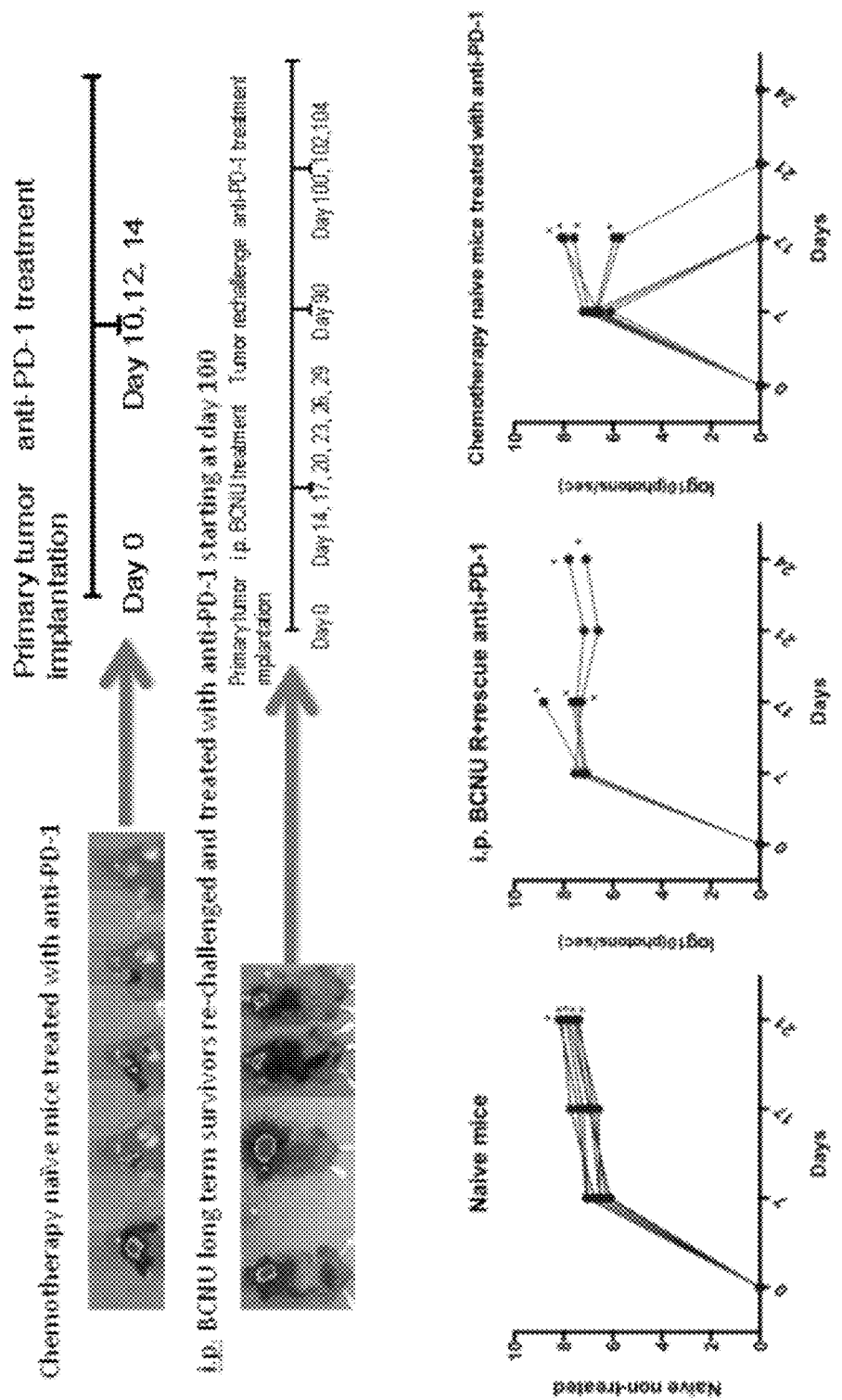
Figure 30:
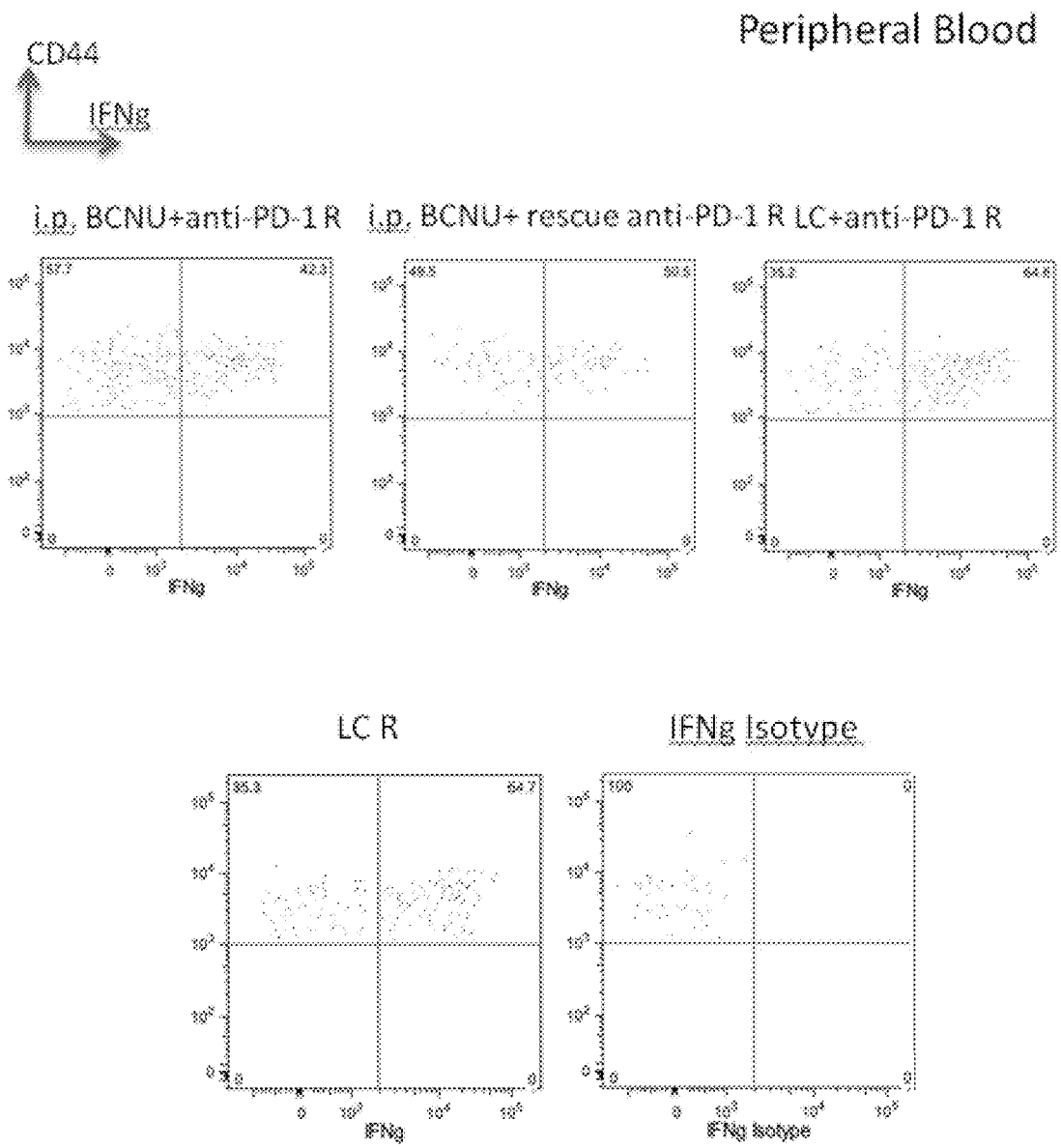
Figure 30:
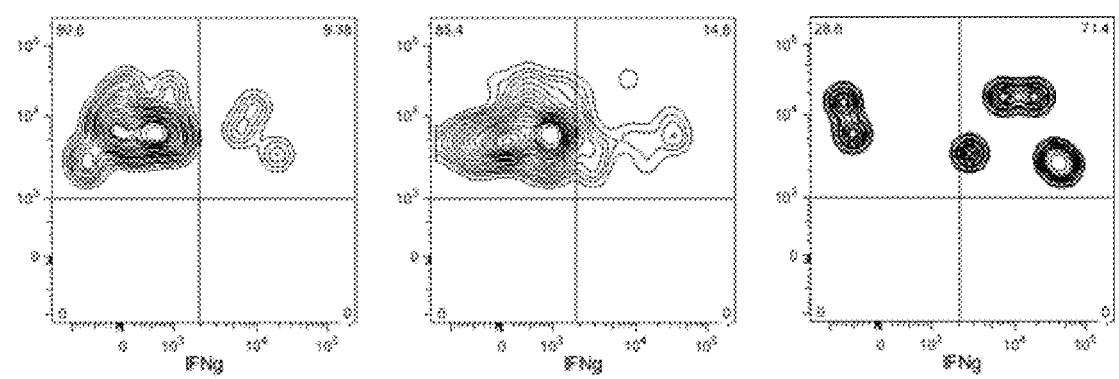
Figure 30:
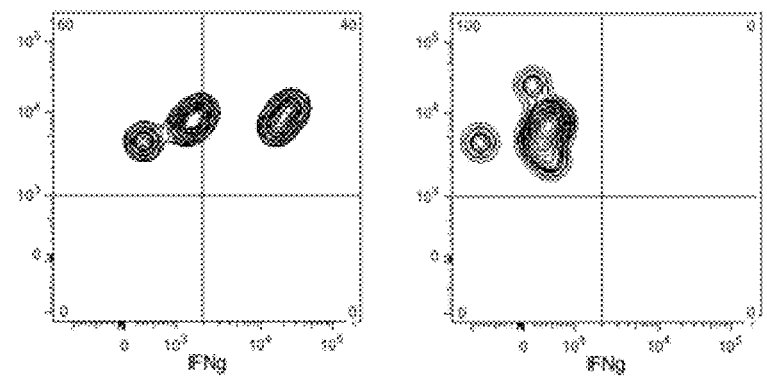
Figure 31:
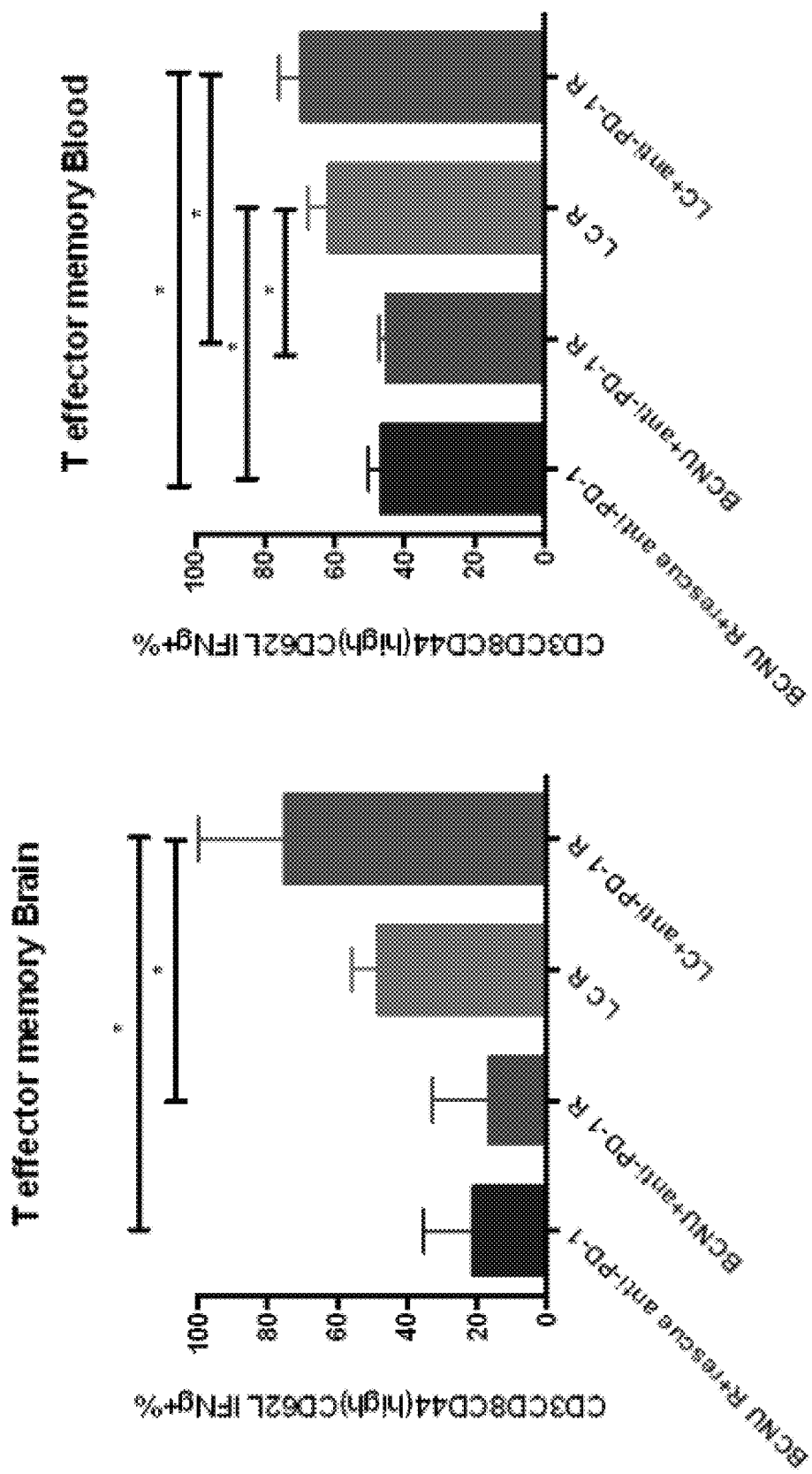
Figure 32:
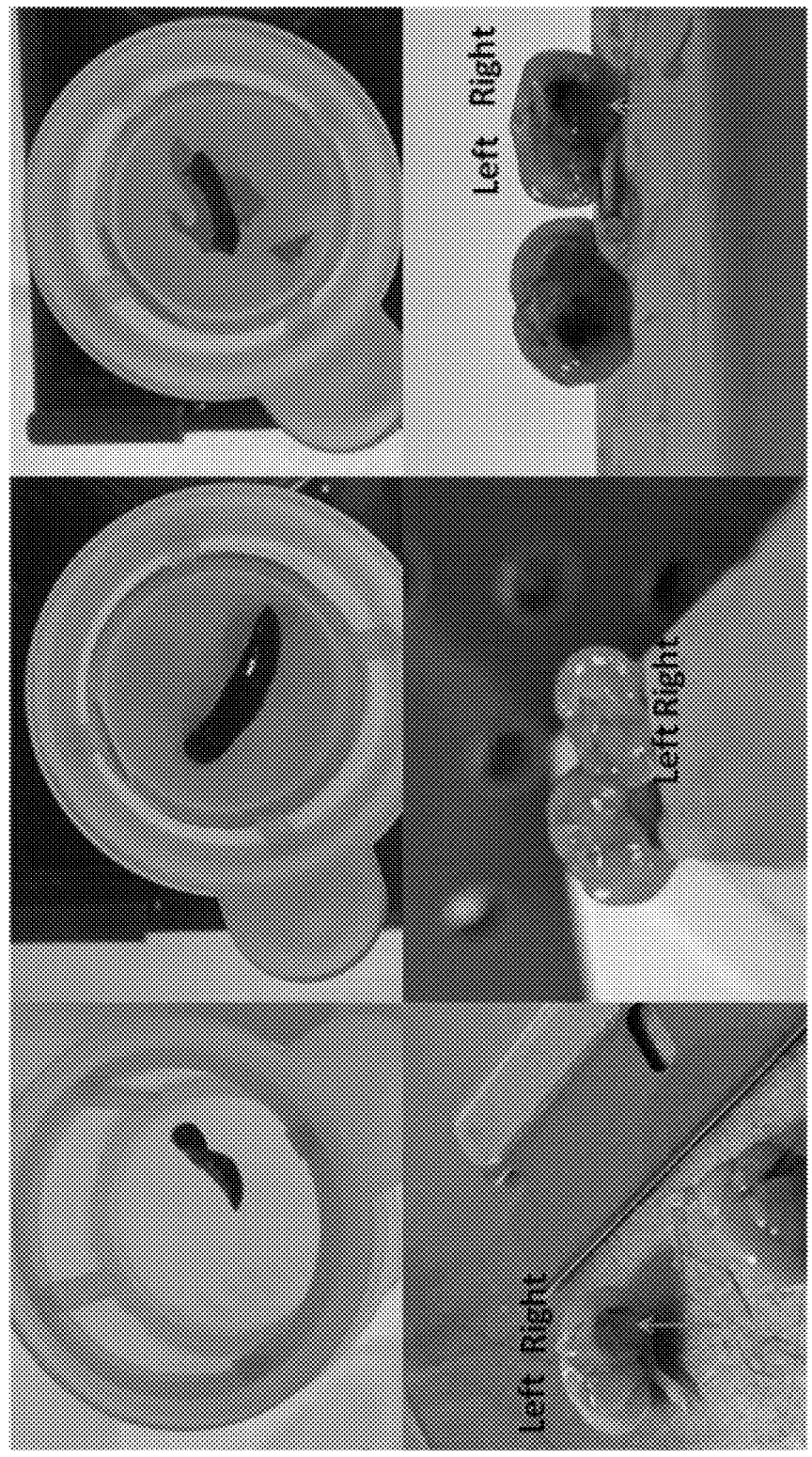

Having thus described the presently disclosed subject matter in general terms, reference will now be made to the accompanying Figures, which are not necessarily drawn to scale, and wherein:

FIG. 1 shows a representative experimental schedule of chemotherapy. Systemic chemotherapy shows severe and persistent lymphodepletion while local chemotherapy (LC) maintains the immune cell populations intact. Mice were treated with either i.p. BCNU or LC at day 14. i.p. BCNU was given 3 times a week for 2 weeks. Flow analysis was performed for all groups for lymphocytes extracted from the brain, draining lymph nodes and the peripheral blood at several time points;

FIG. 2 shows early (day 26) and late (day 41) lymphopenia observed in the peripheral blood of mice treated with i.p. BCNU. The same pattern was observed in the brain and the draining lymph nodes (DLN) of mice treated with systemic chemotherapy. i.p. BCNU exhibited late myelotoxicity (day 30) as indicated by the reduced bone marrow cellularity and the reduced CD45+(leukocytes) population. EP=Empty Polymer (no chemotherapy);

FIG. 3 shows CD3 counts at day 141. Persistent and potentially irreversible lymphopenia is observed in mice receiving i.p. BCNU. The lymphocyte counts (CD3+ cells) were decreased in the peripheral blood, the draining lymph nodes and the spleen of long term survivor mice treated with i.p. BCNU compared to LC treated mice or untreated (control) mice;

FIG. 4 shows that the use of local chemotherapy post anti-PD1 immunotherapy exhibits a superior survival profile compared to monotherapies as well as the combination of systemic chemotherapy and anti-PD1 treatment. The experimental set-up is shown (top);

FIG. 5 shows the tumor progression of intracranially implanted GL-261 tumors measured by bioluminescent imaging. Anti-PD1 treatment exhibits an immediate anti-tumor effect with most mice that are finally cured losing their bioluminescent signal at day 14. Interestingly, some mice treated with anti-PD1 and i.p. BCNU initially lost their signal but they eventually regained it and died of a progressing tumor. *Denotes mice that died after the last IVIS imaging session;

FIG. 6 shows that the combination of LC and anti-PD1 mounts a robust local and systemic immune response, while systemic chemotherapy in combination with anti-PD1 abrogates the immune activation anti-PD1 alone creates. Systemic chemotherapy in combination with anti-PD1 exhibits lymphopenia in the peripheral blood while LC and anti-PD1 maintains high lymphocyte counts at all time points;

FIG. 7 shows an increased number of CD3+ peripheral blood lymphocytes (PBLs) compared to control mice for a prolonged period of time (day 41) after the end of the therapeutic regimen;

FIG. 8 shows that systemic chemotherapy in combination with anti-PD1 exhibits decreased numbers of CD8+IFNγ producing cells (effector cells) compared to LC and anti-PD1 in the DLNs. A decreased percentage of CD4+Foxp3+ (Tregs) cells was exhibited with both systemic chemotherapy and anti-PD1 as well as LC and anti-PD1;

FIG. 9 shows that systemic chemotherapy in combination with anti-PD1 exhibits lymphopenia in the DLNs while LC and anti-PD1 maintains high lymphocyte counts. The percent of Tregs is decreased with any treatment and the percent of CD8+IFNγ+ (Teffectors) cells was highest in the combination of LC and anti-PD1;

FIG. 10 shows that bone marrow cellularity was decreased in mice treated with systemic chemotherapy and anti-PD1. Gating on CD45+ cells (leukocytes) reveals decreased leukocyte production from the bone marrow in mice treated with systemic chemotherapy or systemic chemotherapy and anti-PD1;

FIG. 11 shows that analysis of specific myeloid subpopulations in the bone marrow (BM) reveals an increased granulocytic population (CD11b+Ly6G+Ly6C(intermediate) in the bone marrow of mice treated with systemic chemotherapy and anti-PD1 and a decreased monocytic population (CD11b+Ly6G-Ly6Chigh) compared to any other treatment. Anti-PD1 or LC did not preferentially affect a specific subpopulation of myeloid cells;

FIG. 12 shows flow cytometric analysis of bone marrow granulocytic and monocytic myeloid-derived suppressor cells (MDSCs);

FIG. 13 shows that analysis of tumor infiltrating lymphocytes shows lymphodepletion in the systemic chemotherapy groups and an immune suppressive phenotype. At day 21, LC and anti-PD1 exhibits high numbers of TILs and increased percentage of Teffectors compared to i.p. BCNU+ anti-PD1 or LC alone. At day 30, systemic chemotherapy groups exhibited lymphodepletion and decreased Teffector function (decreased IFNγ production). However, LC increased the Teffector function resulting in an increased effector T cell (Teff)/regulatory T cell (Treg) ratio;

FIG. 14 shows that the addition of anti-PD1 antibody to LC treatment increased the percentage of CD8-IFNγ producing cells;

FIG. 15 shows that the addition of anti-PD1 to LC treatment did not significantly decrease the percentage of regulatory T cells (Treg cells);

FIG. 16 shows the analysis of tumor infiltrating immune cells in tumor bearing mice for all treatment groups. CD11b+CD45 intermediate cells are microglial cells, CD11b+CD45 high are myeloid cells and CD11b−CD45 high are tumor infiltrating lymphocytes (TILs);

FIG. 17 shows that the anti-PD1 treated group is enriched for TILs compared to microglia-macrophages at both Day 21 and 30. However, none of the other treatment groups showed any changes in the TILs/Myeloid cells ratio;

FIG. 18 shows gating on the CD45+ cells (leukocytes) infiltrating the brain. Focusing on the CD11b+CD11c+ cells (dendritic cells), an increased infiltration of dendritic cells in the LC treated mice was observed;

FIG. 19 shows the use of chemotherapy prior to immunotherapy—survival analysis: LC and anti-PD1 exhibits an increase in survival compared to monotherapies or i.p. BCNU and anti-PD1. The combination of i.p. BCNU with anti-PD1 abrogates the positive survival profile anti-PD1 produced as monotherapy;

FIG. 20 shows the adoptive transfer of OT-I lymphocytes from RAG−/− mice in GL-261 ova tumor bearing mice. LC allows for expansion of antigen specific T cells intratumorally and in the DLNs. Adoptively transferred OT-I lymphocytes expressing the congenic marker CD45.2 were recovered from recipient mice 4 days after the transfer; LC increased the homing and expansion of OT-I cells in the LC and LC+anti-PD1 groups compared to anti-PD1 or i.p. BCNU and i.p. BCNU+anti-PD1;

FIG. 21 shows adoptive transfer of OT-I lymphocytes from RAG−/− mice in GL-261 ova tumor bearing mice;

FIG. 22 shows in vivo proliferation of adoptively transferred OT-I T cells in the spleen. Splenocytes from OT-I RAG−/− CD45.2 mice were labeled with cell proliferation dye and were adoptively transferred to CD45.1 B6 mice treated with either i.p. BCNU or LC (and the appropriate controls: EP and No Tx). Three days after adoptive transfer, the recipient mice were sacrificed and their spleen was harvested. The in vivo proliferation capacity of CD45.2+ CD3+ transferred lymphocytes was assessed by the dilution of cell proliferation dye;

FIG. 23 shows that that systemic chemotherapy abrogates the antitumor memory response in anti-PD1 treated mice and causes functional impairment of T memory cells. Long term survivor mice from all groups were rechallenged; mice in the local chemotherapy groups and the anti-PD1 group prevented tumor recurrence while systemic chemotherapy treated mice failed to reject the rechallenged tumor and died;

FIG. 24 shows a representative study in which long term survivors were re-challenged with GL-261 cells implanted in the contralateral hemisphere of the brain while naïve mice with no previous exposure to tumor cells were challenged in parallel. Rechallenged mice were followed with bioluminescent imaging; mice treated with systemic chemotherapy exhibited progressively increasing bioluminescent imaging (BLI) signal and eventually died of their tumor. *Denotes mice that died after the last IVIS imaging session. Naïve: GL-261 implanted, non-treated mice; anti-PD1 R: anti-PD1 rechallenged mice; BCNU R:BCNU rechallenged mice; i.p. BCNU+anti-PD1 R: i.p. BCNU+anti-PD1 Rechallenged mice; LC+anti-PD1 R: local chemotherapy+anti-PD1 rechallenged mice; and anti-PD1: mice with primary tumor treated with anti-PD1 for the first time;

FIG. 25 shows a representative day 20 post re-challenge experiment. The percent of effector CD8 memory cells producing IFNγ was lower in the systemic chemotherapy treated mice across all peripheral tissues including the spleen, peripheral blood and DLNs;

FIG. 26 shows a representative flow cytometric analysis from a day 20 post re-challenge experiment (FIG. 25). Twenty days after intracranial tumor re-challenge, long-term survivor mice were assessed for the presence of memory cells;

FIG. 27 shows therapeutic adoptive transfer of CD8 cells from rechallenged LC+anti-PD1 mice to i.p. BCNU+anti-PD1 rechallenged mice. Long term survivor mice from the LC+anti-PD1 group rejected the rechallenged tumor whereas i.p. BCNU+anti-PD1 did not. Spleens from mice treated with LC+anti-PD1 R group were harvested and CD8 cells were magnetically isolated. The cells were adoptively transferred via retro-orbital injection to the rechallenged i.p. BCNU+anti-PD1 mice. Two out of four mice (50%) did not respond to the transfer whereas the other 50% (two mice) showed a considerable decrease in the tumor burden and maintained a state of tumor equilibrium with steady bioluminescent signal for more than a week;

FIG. 28 shows the adoptive transfer of CD8 cells from LC+anti-PD1 R mice to i.p. BCNU+anti-PD1 R mice. Bioluminescent imaging shows the progression of the tumor for naïve mice and rechallenged long term survivor mice from the i.p. BCNU+anti-PD1 group with or without the CD8 adoptive transfer. Two out of four mice in the i.p. BCNU+anti-PD1 R with CD8 AT (Adoptive Transfer) group died (denoted with asterisk) and two out of four mice showed a definite decrease in bioluminescent signal after the adoptive transfer and maintained similar signal for at least a week from day 17 to day 24. *Denotes mice that died after the last IVIS imaging session. Naïve: GL-261 implanted, non-treated mice; anti-PD1 R: anti-PD1 rechallenged mice; BCNU R:BCNU rechallenged mice; i.p. BCNU+anti-PD1 R: i.p. BCNU+anti-PD1 rechallenged mice; LC+anti-PD1 R: local chemotherapy+anti-PD1 rechallenged mice; anti-PD1: mice with primary tumor treated with anti-PD1 for the first time;

FIG. 29 shows the anti-PD1 response to chemotherapy naïve and chemotherapy treated mice. Mice treated with systemic chemotherapy do not respond to anti-PD1 treatment as chemotherapy naïve mice. Mice with recurrent tumor after tumor rechallenge were treated with anti-PD1 in an attempt to be cured. Chemotherapy naïve mice were treated with anti-PD1 at the same time as controls with the mice developing recurrent tumors not responding to anti-PD1. Naïve: GL-261 implanted, non-treated mice; anti-PD1 R: anti-PD1 rechallenged mice; BCNU R:BCNU rechallenged mice; i.p. BCNU+anti-PD1 R: i.p. BCNU+anti-PD1 rechallenged mice; LC+anti-PD1 R: local chemotherapy+anti-PD1 rechallenged mice; and anti-PD1: mice with primary tumor treated with anti-PD1 for the first time. *Denotes mice that died after the last IVIS imaging session;

FIG. 30 shows that the T effector memory function of rechallenged mice in the systemic chemotherapy group cannot be restored by anti-PD1 treatment. Naïve: GL-261 implanted, non-treated mice; anti-PD1 R: anti-PD1 rechallenged mice; BCNU R:BCNU rechallenged mice; i.p. BCNU+anti-PD1 R: i.p. BCNU+anti-PD1 rechallenged mice; LC+anti-PD1 R: local chemotherapy+anti-PD1 rechallenged mice; and anti-PD1: mice with primary tumor treated with anti-PD1 for the first time;

FIG. 31 is a graph depicting a quantification of the results obtained in FIG. 30, demonstrating that the T effector memory function of rechallenged mice in the systemic chemotherapy group cannot be restored by anti-PD1 treatment as seen by flow cytometry plots in FIG. 30; and FIG. 32 shows necropsy findings at Day 104. Upon necropsy, the spleens of mice treated with systemic chemotherapy and anti-PD1 or systemic chemotherapy and rescue anti-PD1 were much smaller than the spleens of LC and anti-PD1 mice.

Furthermore, mice treated with systemic chemotherapy and rechallenged on the opposite hemisphere (right) than the initial tumor implantation (left) exhibited big tumor masses indicating uncontrolled tumor progression, unlike the LC and anti-PD1 rechallenged mice that did not show any sign of tumor recurrence. Naïve: GL-261 implanted, non-treated mice; anti-PD1 R: anti-PD1 rechallenged mice; BCNU R:BCNU rechallenged mice; i.p. BCNU+anti-PD1 R: i.p. BCNU+anti-PD1 rechallenged mice; LC+anti-PD1 R: local chemotherapy+anti-PD1 rechallenged mice; and anti-PD 1: mice with primary tumor treated with anti-PD 1 for the first time.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Systemic chemotherapy causes immunosuppression, which in turn abrogates the efficacy immune checkpoint molecules have against cancer. The presently disclosed subject matter provides methods comprising the use of local chemotherapy, such as intratumorally or within the tumor bed, to avoid the systemic immunosuppressive effects of systemic chemotherapy combined with at least one immunotherapeutic agent. In some embodiments, the local chemotherapy further enhances the antitumor activity of the immunotherapeutic agent. In some embodiments, at least one immunotherapeutic agent is an immune checkpoint molecules. This novel combination of local chemotherapy with an immunotherapeutic agent has the potential to change the way patients can be treated in a variety of malignancies.

As seen herein below, the combination of local chemotherapy and an immune checkpoint molecules, such as an anti-PD1 antibody, exhibits a strong survival and immunologic benefit compared to treatment with systemic chemotherapy and an immune checkpoint molecules, or monotherapy treatment using local chemotherapy or the immune checkpoint molecules alone. The presently disclosed subject matter demonstrates superior efficacy of local chemotherapy delivery in combination with immunotherapy for primary brain tumors (gliomas), such as glioblastomas. The presently disclosed subject matter can be used for treating many other tumor types currently treated with systemic chemotherapy.

I. Methods for Treating Cancer

In some embodiments, the presently disclosed subject matter provides a method for the treatment of cancer comprising administering to a patient with a cancer an effective amount of a combination treatment comprising: (a) a locally administered chemotherapy; and (b) an immunotherapeutic agent. In some embodiments, the presently disclosed subject matter provides a method for prolonging survival of a cancer patient comprising administering to a patient with a cancer an effective amount of a combination treatment comprising: (a) a locally administered chemotherapy; and (b) an immunotherapeutic agent. In some embodiments, the immunotherapeutic agent comprises an immune checkpoint molecule. In some embodiments, the locally administered chemotherapy is administered intratumorally and/or within a tumor bed.

As used herein, the term "treating" can include reversing, alleviating, inhibiting the progression of, preventing or reducing the likelihood of the disease, disorder, or condition to which such term applies, or one or more symptoms or manifestations of such disease, disorder or condition (e.g., cancer).

In some embodiments, the combination treatment reduces the likelihood of tumor progression and/or recurrence. For example, the combination treatment can reduce the likelihood of tumor progression and/or recurrence by at least 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99% or more as compared to the likelihood of tumor progression and/or recurrence in the patient when treated with systemic chemotherapy plus the immunotherapeutic agent, such as an immune checkpoint molecule, or as compared to monotherapy treatment with either the locally administered chemotherapy or the immunotherapeutic agent alone. In some embodiments, the combination treatment completely inhibits tumor progression and/or recurrence in the patient. In some embodiments, the combination treatment reduces the likelihood of tumor progression and/or recurrence by at least approximately 40% as compared to the likelihood of tumor progression and/or recurrence in the patient when treated with systemic chemotherapy plus the immunotherapeutic agent, or as compared to monotherapy treatment with either the locally administered chemotherapy or the immunotherapeutic agent alone.

In some embodiments, the combination treatment extends survival of the patient. For example, the combination treatment can extend survival (e.g., progression free survival) of the patient by 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99%, 1-fold, 1.1-fold, 1.2-fold, 1.3-fold, 1.4-fold, 1.5-fold, 1.6-fold, 1.7-fold, 1.8-fold, 1.9-fold, 2.0 fold, 2.5-fold, 3.0-fold, 3.5-fold, 4.0-fold, 5.0-fold, 6-fold, 7-fold, 8-fold, 9-fold, 10-fold, or more as compared to survival of the patient when treated with systemic chemotherapy plus the immunotherapeutic agent, or as compared to monotherapy treatment with either the locally administered chemotherapy or the immunotherapeutic agent alone. In some embodiments, the combination treatment extends survival of the patient by at least approximately 40%_ as compared to survival of the patient when treated with systemic chemotherapy plus the immunotherapeutic agent, or as compared to monotherapy treatment with either the locally administered chemotherapy or the immunotherapeutic agent alone.

In some embodiments, the combination treatment extends progression free survival of the patient until the patient succumbs to another disease, disorder, or condition, or dies naturally as a result of old age.

In some embodiments, the combination treatment stimulates an anti-tumor response in the patient in the absence of inducing immunosuppression in the patient. Unexpectedly and surprisingly, work described herein demonstrates that combination treatment using local chemotherapy (e.g., a locally administered chemotherapy administered intratumorally or within the tumor bed delivered, for example, by catheters, polymers, or nanoparticles) and an immunotherapeutic agent stimulated an anti-tumor immunotherapeutic response, for example by increasing dendritic cell infiltration in the tumor microenvironment, increasing the persistence of antigen specific T cells specific for a tumor antigen of the patient, enhancing retention of immunologic memory upon recurrence of the tumor or tumor antigen, increasing clonal expansion of antigen specific T cells, increasing antigen release from local chemotherapy induced tumor cell death, increasing and/or maintaining CD3+(lymphocyte) cell counts in the patient, increasing and/or maintaining CD45+(leukocyte) cell counts in the patient, increasing and/or maintaining CD8+IFNγ producing cell (effector cell) counts in the patient in the absence of inducing immunosuppression in the patient, for example by stimulating the anti-tumor immunotherapeutic response noted above without causing the patient to exhibit lymphopenia (reduced CD3+ count), myelotoxicity, reduced bone marrow cellularity, leukopenia (reduced CD45+ count), reduced CD8+IFNγ producing cell (effector cell) count; functional impairment of T memory cells. A "cancer" in a patient refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. Cancer as used herein includes newly diagnosed or recurrent cancers, including without limitation, blastomas, carcinomas, gliomas, leukemias, lymphomas, melanomas, myeloma, and sarcomas. Cancer as used herein includes, but is not limited to, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas. In some embodiments, the cancer comprises Stage 0 cancer. In some embodiments, the cancer comprises Stage I cancer. In some embodiments, the cancer comprises Stage II cancer. In some embodiments, the cancer comprises Stage III cancer. In some embodiments, the cancer comprises Stage IV cancer. In some embodiments, the cancer is refractory and/or metastatic. For example, the cancer may be refractory to treatment with radiotherapy, systemic chemotherapy, monotreatment with local chemotherapy, or monotreatment with immunotherapy. In some embodiments, the cancer is metastatic colorectal cancer. In some embodiments, the cancer is diffuse large B-cell lymphoma. In some embodiments, the cancer is follicular lymphoma (e.g., refractory follicular lymphoma). In some embodiments, the cancer is glioblastoma. In some embodiments, the cancer is multiple myeloma comprising solid tumors (see, e.g., Stegman and Alexanian, "Solid tumors in multiple myeloma," *Ann Intern Med.* 1979; 90(5):780-2). In some embodiments, the cancer is non-small cell lung cancer. In some embodiments, the cancer is renal cell carcinoma. In some embodiments, the cancer is urothelial bladder cancer. In some embodiments, the cancer is a solid form of a newly diagnosed or a recurrent cancer selected from the group consisting of a blastoma, a carcinoma, a glioma, a leukemia, a lymphoma, a melanoma, a myeloma, and a sarcoma. In some embodiments, the cancer is selected from the group consisting of colorectal cancer, diffuse large B-cell lymphoma, follicular lymphoma, glioblastoma, lower grade gliomas, melanoma, multiple myeloma, non-small cell lung cancer, renal cell carcinoma, urothelial bladder cancer, ovarian cystadenocarcinoma, stomach adenocarcinoma and other gastrointestinal malignancies, head and neck adenocarcinoma, pancreatic adenocarcinoma, prostate adenocarcinoma, breast adenocarcinoma, breast cancer and pancreatic cancer.

A "tumor," as used herein, refers to all neoplastic cell growth and proliferation, whether malignant or benign, and all precancerous and cancerous cells and tissues. A "solid tumor", as used herein, is an abnormal mass of tissue that generally does not contain cysts or liquid areas. A solid tumor may be in the brain, colon, breasts, prostate, liver, kidneys, lungs, esophagus, head and neck, ovaries, cervix, stomach, colon, rectum, bladder, uterus, testes, and pancreas, as non-limiting examples. In some embodiments, the solid tumor regresses or its growth is slowed or arrested after the solid tumor is treated with the presently disclosed methods. In other embodiments, the solid tumor is malignant.

A "locally administered chemotherapy" is used to connote a compound or composition that is locally administered in the treatment of cancer, such as intratumorally and/or within the tumor bed. In some embodiments, local immunotherapy does not compromise the body's ability to mount an immune response. In some embodiments, locally administered chemotherapy allows generation of a robust immune response, whereas systemic chemotherapy compromises the body's ability to generate an effective immune response.

Locally administered chemotherapy useful in methods, compositions, and kits disclosed herein include, but are not limited to, alkylating agents such as thiotepa, temozolomide, and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g. paclitaxel and docetaxel; chlorambucil; gemcitabine; 6-thioguanine; mercaptopurine; platinum analogs such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine; retinoic acid; esperamicins; capecitabine; immune system blockers, e.g. rapamycin; amino acid modifiers, e.g. asparaginase; and pharmaceutically acceptable salts, acids or derivatives of any of the above. Locally administered chemotherapy also includes anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the locally administered chemotherapy is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide, and irinotecan, as well as pharmaceutically acceptable salts, acids, or derivatives of any of these.

In some embodiments, the locally administered chemotherapy is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the locally administered chemotherapy is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain alternative embodiments, the antimitotic agent comprises a vinca alkaloid, such as vincristine, binblastine, vinorelbine, or vindesine, or pharmaceutically acceptable salts, acids, or derivatives thereof.

In some embodiments, the locally administered chemotherapy is formulated by loading the locally administered chemotherapy into a lipid particulate drug delivery system, a polymeric drug delivery system, or a catheter.

Examples of suitable lipid particulate drug delivery systems include, for example, solid lipid nanoparticles, nanostructured lipid carriers, lipid drug conjugate-nanoparticles, liposomes, transfersomes, ethosomes, lipospheres, niosomes, cubosomes, virosomes, iscoms, nanoemulsions, cochleates, and phytosomes. In some embodiments, the lipid particulate drug delivery system is selected from the group consisting of a solid lipid nanoparticle, a nanostructured lipid carrier, a lipid drug conjugate-nanoparticle, a liposome, a transfersome, an ethosome, a liposphere, a niosome, a cubosome, a virosome, an iscom, a nanoemulsion, a cochleate, and a phytosome.

Examples or suitable polymeric drug delivery systems include, for example, dendrimers, micelles, polymeric microspheres, polymeric nanoparticles, and wafers. Polymer microspheres include those fabricated from PLGA, poly (methylidene malonate), PMM, poly(epsilon-caprolactone), chitosan, and the like. In other embodiments, particularly for intracranial applications, convection-enhanced delivery (CED) of nanoparticles, in which compositions in nanoparticles are infused continuously into the brain tissue via bulk fluid flow using a syringe pump, can be used. Examples of drug delivery wafers include, but are not limited to, the Gliadel® like device, electrospun/rotary jet-spun wafers, biodegradable polymers giving a sustained drug release, the DC Bead®, a composite nanofiber mat electrospun from an emulsion containing PLGA, biodegradable electrospun polymeric implants in the form of microfiber discs and sheets, electrospun PLGA fibers, PLA/PLGA electrospun fibers, fibrous wafers made up of two different kinds of polymeric fibers loaded separately with two different drugs, and the like. In some embodiments, the locally administered chemotherapy comprises a BCNU implantable wafer. In some embodiments, the polymeric drug delivery system is selected from the group consisting of a dendrimer, a micelle, a polymeric microsphere, a polymeric nanoparticle, and a wafer. In some embodiments, the delivery by a catheter is selected from the group consisting of microcatheter delivery and convection enhanced delivery.

As used herein, the term "immunotherapeutic agent" refers to a molecule that can aid in the treatment of a disease by inducing, enhancing, or suppressing an immune response. Examples of immunotherapeutic agents include, but are not limited to, immune checkpoint molecules (e.g., antibodies to immune checkpoint proteins), interleukins (e.g., IL-2, IL-7, IL-12, IL-15), cytokines (e.g., interferons, G-CSF, imiquimod), chemokines (e.g., CCL3, CCL26, CXCL7), vaccines (e.g., peptide vaccines, dendritic cell (DC) vaccines, EGFRvIII vaccines, mesothilin vaccine, G-VAX, listeria vaccines), and adoptive T cell therapy including chimeric antigen receptor T cells (CAR T cells).

As used herein, the term "immune checkpoint molecule" refers to molecules that totally or partially reduce, inhibit, interfere with, activate, or modulate one or more checkpoint proteins (i.e., an immune checkpoint receptor or a ligand for the immune checkpoint receptor). In some embodiments, the immune checkpoint molecule is an inhibitor molecule.

Examples of immune checkpoint molecules that can be used in the presently disclosed methods include, but are not limited to, small organic molecules (e.g., haptens) or small inorganic molecules; saccharides; oligosaccharides; polysaccharides; a biological macromolecule selected from the group consisting of peptides (e.g., aptides), proteins, peptide analogs and derivatives; peptidomimetics; nucleic acids selected from the group consisting of miRNAs, siRNAs, shRNAs, antisense nucleic acids, such as antisense RNAs, ribozymes, and aptamers; an extract made from biological materials selected from the group consisting of bacteria, plants, fungi, animal cells, and animal tissues; naturally occurring or synthetic compositions; and any combination thereof. Other examples of immune checkpoint molecules include orthosteric inhibitors, allosteric regulators, interfacial binders, and molecular analogues of substrates that act as competitive inhibitors. Specific examples of immune checkpoint molecules include anti-PD-1, anti-PD-L1, anti-CTLA-4, anti-Lag-3, Anti-CD137, Anti-KIR, anti-Tim3, anti-Ox40, SP4205, a small molecule blocker for the interaction between Interleukin-2 (IL-2) and the IL-2 receptor and inhibitors of indoleamine-pyrrole 2,3-dioxygenase (IDO), such as the natural products cabbage extract brassinin, the marine hydroid extract annulin B, and the marine sponge extract exiguamine A, and 1-methyl tryptophan (1-MT), a tryptophan mimetic.

As used interchangeably herein, the terms "nucleic acids," "oligonucleotides," and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one of the following modifications: (a) an alternative linking group, (b) an analogous form of purine, (c) an analogous form of pyrimidine, or (d) an analogous sugar. For examples of analogous linking groups, purine, pyrimidines, and sugars, see for example PCT Patent App. Pub. No. WO 95/04064. The polynucleotide sequences of the presently disclosed subject matter may be prepared by any known method, including synthetic, recombinant, ex vivo generation, or a combination thereof, as well as utilizing any purification methods known in the art.

The term "antisense nucleic acid" refers to an oligonucleotide that has a nucleotide sequence that interacts through base pairing with a specific complementary nucleic acid sequence involved in the expression of the target such that the expression of the gene is reduced. Preferably, the specific nucleic acid sequence involved in the expression of the gene is a genomic DNA molecule or mRNA molecule that encodes (a part of) the gene. This genomic DNA molecule can comprise regulatory regions of the gene, or the coding sequence for the mature gene.

The down regulation of gene expression using antisense nucleic acids can be achieved at the translational or transcriptional level using an expression-inhibitory agent. Antisense nucleic acids of the invention are preferably nucleic acid fragments capable of specifically hybridizing with all or part of a nucleic acid encoding a protein kinase or a corresponding messenger gene or mRNA. The preparation and use of antisense nucleic acids, DNA encoding antisense RNAs and the use of oligo and genetic antisense is known in the art.

Small interfering RNA (siRNA) mediate the post-transcriptional process of gene silencing by double stranded RNA (dsRNA) that is homologous in sequence to the silenced RNA. A small hairpin RNA or short hairpin RNA (shRNA) is an artificial RNA molecule with a tight hairpin turn. A microRNA (miRNA) is a small non-coding RNA molecule which also functions in RNA silencing.

Ribozymes are catalytic RNA molecules (RNA enzymes) that have separate catalytic and substrate binding domains. The substrate binding sequence combines by nucleotide complementarity and, possibly, non-hydrogen bond interactions with its mRNA sequence. The catalytic portion cleaves the mRNA at a specific site.

As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. The term "polypeptide" or "protein" as used herein refers to a molecule comprising a string of at least three amino acids linked together by peptide bonds. The terms "protein" and "polypeptide" may be used interchangeably. Proteins may be recombinant or naturally derived.

As used herein, the term "reduce" or "inhibit," and grammatical derivations thereof, refers to the ability of an agent to block, partially block, interfere, decrease, reduce or deactivate a biological molecule, pathway or mechanism of action. Thus, one of ordinary skill in the art would appreciate that the term "inhibit" encompasses a complete and/or partial loss of activity, e.g., a loss in activity by at least 10%, in some embodiments, a loss in activity by at least 20%, 30%, 50%, 75%, 95%, 98%, and up to and including 100%.

As used herein, the terms "immune checkpoint protein" and "checkpoint protein" are used synonymously to refer to a molecule that transmits an inhibitory signal to an immune cell. In some embodiments, checkpoint proteins regulate T-cell activation or function. Numerous checkpoint proteins are known, such as CTLA-4 and its ligands CD80 and CD86; and PD1 with its ligands PDL1 and PDL2. These proteins are responsible for co-stimulatory or inhibitory interactions of T-cell responses. Immune checkpoint proteins regulate and maintain self-tolerance and the duration and amplitude of physiological immune responses. With respect to an immune checkpoint, the term "activity" includes the ability of an immune checkpoint to modulate an inhibitory signal in an activated immune cell, e.g., by engaging an immune checkpoint ligand on an antigen presenting cell. Modulation of an inhibitory signal in an immune cell results in modulation of proliferation of, and/or cytokine secretion by, an immune cell. Thus, the term "an immune checkpoint activity" includes the ability of an immune checkpoint to bind its natural ligand(s), the ability to modulate immune cell costimulatory or inhibitory signals, and the ability to modulate the immune response.

PD1 (Programmed Cell Death Protein 1; e.g. GenBank Accession No. NP_005009.2), also known as CD279 (Cluster of Differentiation 279), is a cell surface membrane protein that is expressed mainly on a subset of activated T lymphocytes. In humans, it is encoded by the PDCD1 gene (Entrez Gene GeneID: 5133). PD1 is a member of the immunoglobulin gene superfamily, and has an extracellular region containing immunoglobulin superfamily domain, a transmembrane domain, and an intracellular region including an immunoreceptor tyrosine-based inhibitory motif. PD1 is rapidly induced on the surface of T-cells in response to anti-CD3. PD1 is also induced on the surface of B-cells (in response to anti-IgM) and is expressed on a subset of thymocytes and myeloid cells. Two types of human PD1 ligands have been identified: PDL1 and PDL2. PD1 ligands comprise a signal sequence, and an IgV domain, an IgC domain, a transmembrane domain, and a short cytoplasmic tail. Both PDL1 (NCBI Reference Sequence: NP_001254635.1) and PDL2 (NCBI Reference Sequence: NP_079515.2) are members of the B7 family of polypeptides.

In some embodiments, the immune checkpoint receptor is PD1. In some embodiments, the immune checkpoint molecule comprises an anti-PD1 antibody. Examples of anti-PD1 antibodies of use in the presently disclosed methods, compositions, and kits include, without limitation, AMP-224, lambrolizumab, nivolumab, and pidilizumab, as shown in Table 1 below. In some embodiments, the anti-PD1 antibody is selected from the group consisting of AMP-224, lambrolizumab, nivolumab, and pidilizumab.

In some embodiments, the ligand for the immune checkpoint receptor is selected from the group consisting of PDL1 and PDL2. In some embodiments, the immune checkpoint molecule is an anti-PDL1 antibody. Examples of anti-PDL1 antibodies of use in the presently disclosed methods, compositions, and kits include, without limitation, BMS-936559, MEDI-4736, and MPDL3280A as shown in Table 1 below. In some embodiments, the anti-PDL1 antibody is selected from the group consisting of BMS-936559, MEDI-4736, and MPDL3280A.

TABLE 1

Exemplary Immune Checkpoint Proteins and Immune Checkpoint Molecules

| Target | Biological function | Antibody or Ig fusion protein | State of clinical development as of January 2012 |
|---|---|---|---|
| CTLA4 | Inhibitory receptor | Ipilimumab | FDA approved for melanoma, Phase II and Phase III trials ongoing for multiple cancers |
| | | Tremelimumab | Previously tested in a Phase III trial of patients with melanoma |
| PD1 | Inhibitory receptor | Nivolumab (BMS-936558, MDX-1106, ONO-4538) fully human Immunoglobulin G4 (IgG4) monoclonal PD-1 antibody | Phase I/II trials in patients with melanoma and renal and lung cancers |
| | | Lambrolizumab (MK3475) humanized monoclonal IgG4 PD-1 antibody | Phase I trial in multiple cancers |
| | | Pidilizumab (CT-011) humanized monoclonal antibody (mAb) | Phase I trial in multiple cancers |
| | | AMP-224 (PDL2-Ig fusion protein that blocks PD1 from binding its partners) | Phase I trial in multiple cancers |
| PDL1 | Ligand for PD1 | MDX-1105 | Phase I trial in multiple cancers |
| | | Multiple mAbs | Phase I trials planned for 2012 |
| LAG3 | Inhibitory receptor | IMP321 (LAG3-Ig fusion protein) | Phase III trial in breast cancer |
| | | Multiple mAbs | Preclinical development |
| B7-H3 | Inhibitory ligand | MGA271 | Phase I trial in multiple cancers |
| B7-H4 | Inhibitory ligand | | Preclinical development |
| TIM3 | Inhibitory receptor | | Preclinical development |

CTLA4, cytotoxic T-lymphocyte-associated antigen 4; FDA, US Food and Drug Administration; Ig, immunoglobulin; LAG3, lymphocyte activation gene 3; mAbs, monoclonal antibodies; PD1, programmed cell death protein 1; PDL, PD1 ligand; TIM3, T cell membrane protein 3.

The term "antibody," also known as an immunoglobulin (Ig), is a large Y-shaped protein produced by B cells that is used by the immune system to identify and neutralize foreign objects such as bacteria and viruses by recognizing a unique portion (epitope) of the foreign target, called an antigen. As used herein, the term "antibody" also includes an "antigen-binding portion" of an antibody (or simply "antibody portion"). The term "antigen-binding portion," as used herein, refers to one or more fragments of an antibody that retain the ability to specifically bind to an antigen (e.g., PD1). It has been shown that the antigen-binding function of an antibody can be performed by fragments of a full-length antibody. Examples of binding fragments encompassed within the term "antigen-binding portion" of an antibody include: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment, which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv)). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and V1 can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (e.g., Holliger et al. (1993) *Proc. Natl. Acad. Sci. USA* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the presently disclosed subject matter bind specifically or substantially specifically to an immune checkpoint protein or functional variants thereof. The terms "monoclonal antibodies" and "monoclonal antibody composition," as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the presently disclosed subject matter may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities (e.g., an isolated antibody that specifically binds an immune checkpoint protein is substantially free of antibodies that specifically bind antigens other than the immune checkpoint protein). Moreover, an isolated antibody may be substantially free of other cellular material and/or chemicals.

An isolated immune checkpoint protein or functional variant thereof (or a nucleic acid encoding such polypeptides), can be used as an immunogen to generate antibodies that bind to the respective immune checkpoint protein or functional variant thereof using standard techniques for polyclonal and monoclonal antibody preparation. A full-length immune checkpoint protein can be used, or alternatively, the presently disclosed subject matter relates to antigenic peptide fragments of an immune checkpoint protein (e.g., receptor or ligand) or functional variants thereof for use as immunogens. An antigenic peptide of an immune checkpoint protein or a functional variant thereof comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptides are regions of an immune checkpoint protein or a functional variant thereof that are located on the surface of the protein, e.g., hydrophilic regions. A standard hydrophobicity analysis of the polypeptide molecule can be performed to identify hydrophilic regions. Highly preferred epitopes encompassed by the antigenic peptides are the regions of the polypeptide molecule which are in the extracellular domain, and therefore are involved in binding. In one embodiment, such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

An immunogen comprising an immune checkpoint protein or a functional variant thereof typically is used to prepare antibodies by immunizing a suitable subject, (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497; Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; and Yeh et al. (1982) *Int. J. Cancer* 29:269-75), a human B cell hybridoma technique (Kozbor et al. (1983) *Immunol. Today* 4:72), the EBV-hybridoma technique (Cole et al. (1985) *Monoclonal Antibodies and Cancer Therapy, Alan R. Liss, Inc., pp.* 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner (1981) *Yale J. Biol. Med.* 54:387-402; Gefter et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well known protocols used for fusing lymphocytes and immortalized cell lines can be applied for the purpose of generating a monoclonal antibody to an immune checkpoint protein (e.g., Galfre, G. et al. (1977) *Nature* 266:55052; Kenneth, R. H. in *Monoclonal Antibodies: A New Dimension In Biological Analyses*, Plenum Publishing Corp., New York, N.Y. (1980); Lerner (1981) *Yale J. Biol. Med.* 54:387-402; Gefter et al. (1977) *Somatic Cell Genet.* 3:231-36). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present presently disclosed subject matter with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the presently disclosed subject matter are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides antibody can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening an antibody display library can be found in, for example, U.S. Pat. No. 5,223,409; PCT Patent App. Pub. No. WO 92/18619; PCT Patent App. Pub. No. WO 91/17271; PCT Patent App. Pub. No. 92/20791; PCT Patent App. Pub. No. WO 92/15679; PCT Patent App. Pub. No. WO 93/01288; PCT Patent App. Pub. No. WO 92/01047; PCT Patent App. Pub. No. WO 92/09690; PCT Patent App. Pub. No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant immunotherapeutic agents, such as immune checkpoint molecules, such as chimeric and humanized monoclonal antibodies, comprising both human and non-human portions, which can be made using standard recombinant DNA techniques, are within the scope of the presently disclosed subject matter. Such chimeric and humanized monoclonal antibodies can be produced by recombinant DNA techniques known in the art, for example using methods described in PCT Patent App. Pub. No. PCT/US86/02269; European Patent App. No. 184,187; European Patent App. No. 171,496; European Patent App. No. 173,494; PCT Application WO 86/01533; U.S. Pat. No. 4,816,567; European Patent App. No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (e.g., Carlson (1988) *Mol. Cell. Biol.* 8:2638-2646; Biocca et al. (1990) *EMBO J.* 9:101-108; Werge et al. (1990) *FEBS Lett* 274:193-198; Carlson (1993) *Proc. Natl. Acad. Sci. USA* 90:7427-7428; Marasco et al. (1993) *Proc. Natl. Acad. Sci. USA* 90:7889-7893; Biocca et al. (1994) *Biotechnology* (NY) 12:396-399; Chen et al. (1994) *Hum. Gene Ther.* 5:595-601; Duan et al. (1994) *Proc. Natl. Acad. Sci. USA* 91:5075-5079; Chen et al. (1994) *Proc. Natl. Acad. Sci. USA* 91:5932-5936; Beerli et al. (1994) *J. Biol. Chem.* 269: 23931-23936; Beerli et al. (1994) *Biochem. Biophys. Res. Commun.* 204:666-672; Mhashilkar et al. (1995) *EMBO J.* 14:1542-1551; Richardson et al. (1995) *Proc. Natl. Acad. Sci. USA* 92:3137-3141; PCT Publication No. WO 94/02610; and PCT Publication No. WO 95/03832).

Additionally, fully human antibodies could be made against an immune checkpoint protein or a functional variant thereof. Fully human antibodies can be made in mice that are transgenic for human immunoglobulin genes, e.g. according to Hogan, et al., "Manipulating the Mouse Embryo: A Laboratory Manual," Cold Spring Harbor Laboratory. Briefly, transgenic mice are immunized with a purified immune checkpoint protein or a functional variant thereof. Spleen cells are harvested and fused to myeloma cells to produce hybridomas. Hybridomas are selected based on their ability to produce antibodies which bind to an immune checkpoint protein or a functional variant thereof. Fully human antibodies would reduce the immunogenicity of such antibodies in a human.

In one embodiment, an antibody for use in the instant presently disclosed subject matter is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to an immune checkpoint protein or a functional variant thereof. In one embodiment, the bispecific antibody could specifically bind to both an immune checkpoint receptor ligand or a functional variant thereof and an immune checkpoint receptor or a functional variant thereof.

Yet another aspect of the presently disclosed subject matter pertains to antibodies that are obtainable by a process comprising, immunizing an animal with an immunogenic immune checkpoint protein or a functional variant thereof, or an immunogenic portion thereof unique to the immune checkpoint protein, and then isolating from the animal antibodies that specifically bind to the polypeptide.

In some embodiments, other immunoregulatory entities can be combined with antibodies against an immune checkpoint protein. Such immunoregulatory entities may include, for example, immunostimulatory cytokines such as GM-CSF, Interleukin-12 (IL-12), and IL-15.

"Functional variants" of immune checkpoints proteins include functional fragments, functional mutant proteins, and/or functional fusion proteins. A functional variant of a selected polypeptide refers to an isolated and/or recombinant protein or polypeptide which has at least one property, activity and/or functional characteristic of the selected polypeptide (e.g., PD1). As used herein, the term "activity," when used with respect to a polypeptide, e.g., PD1, includes activities which are inherent in the structure of the wild-type protein.

Generally, fragments or portions of an immune checkpoint protein encompassed by the presently disclosed subject matter include those having a deletion (i.e. one or more deletions) of an amino acid (i.e., one or more amino acids) relative to the wild-type immune checkpoint protein (such as N-terminal, C-terminal or internal deletions). Fragments or portions in which only contiguous amino acids have been deleted or in which non-contiguous amino acids have been deleted relative to a wild-type immune checkpoint protein are also envisioned. Generally, mutants or derivatives of immune checkpoint proteins encompassed by the present presently disclosed subject matter include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of immune checkpoint proteins differing by the addition, deletion and/or substitution of one or more contiguous or non-contiguous amino acid residues.

Generally, a functional variant of an immune checkpoint protein has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to the wild-type amino acid sequence for an immune checkpoint protein over the length of the variant.

"Sequence identity" or "identity" in the context of proteins or polypeptides refers to the amino acid residues in two amino acid sequences that are the same when aligned for maximum correspondence over a specified comparison window.

Thus, "percentage of sequence identity" refers to the value determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized. The "Clustal V method of alignment" corresponds to the alignment method labeled Clustal V (described by Higgins and Sharp (1989) *CABIOS* 5:151-153; Higgins et al. (1992) *Comput. Appl. Biosci.* 8:189-191) and found in the MegAlign™ program of the LASERGENE bioinformatics computing suite (DNASTAR Inc., Madison, Wis.).

It is well understood by one skilled in the art that many levels of sequence identity are useful in identifying proteins or polypeptides (e.g., from other species) wherein the proteins or polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present presently disclosed subject matter, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

The terms "subject" and "patient" are used interchangeably herein. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease.

Aspects of the presently disclosed subject matter relate to immunotherapeutic, non-immunosuppressive compositions comprising a locally administered chemotherapy and/or an immunotherapeutic agent, such as an immune checkpoint molecule, formulated for local administration (e.g., intratumoral). In some embodiments, the presently disclosed subject matter provides an immunotherapeutic, non-immunosuppressive composition comprising: (a) a locally administered chemotherapy; and (b) an immunotherapeutic agent.

The presently disclosed subject matter also contemplates the use of such immunotherapeutic, non-immunosuppressive compositions for the treatment of a cancer. In some embodiments, the presently disclosed methods comprise the use of the presently disclosed immunotherapeutic, non-immunosuppressive compositions for the manufacture of a medicament for the treatment of a cancer. Generally, the presently disclosed compositions (e.g., comprising an immunotherapeutic agent) can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art. However, in some particular embodiments, the presently disclosed compositions are administered locally, such as intratumorally, so that the compositions are directly administered into a solid tumor (or injected or implanted into a microenvironment in which the solid tumor resides). In some embodiments, intratumoral administration comprises injection into a solid tumor of the patient or injection or implantation into a microenvironment in which the solid tumor resides or resided. The means of administration into a solid tumor include a needle, needleless injection device, or any other means by which the immunotherapeutic agent and locally administered chemotherapy can be administered locally. It should be appreciated that all or a portion of the solid tumor may be surgically removed prior to locally administered chemotherapy and/or immunotherapeutic agent. In some embodiments, the methods further comprise surgically removing all or a portion of the solid tumor prior to locally administered chemotherapy. In some embodiments, the immunotherapeutic agent and the locally administered chemotherapy are delivered to the tumor site using drug delivery wafers, either separately or together.

The phrases "systemic administration", "administered systemically", "peripheral administration" and "administered peripherally" as used herein mean the administration of compositions comprising at least one immunotherapeutic agent combined with at least one locally administered chemotherapy, such that they enter the patient's system and, thus, are subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The phrases "local administration" and "administered locally" as used herein mean the administration of compositions comprising at least one immunotherapeutic agent combined with at least one locally administered chemotherapy, such that they enter into a patient's solid tumor and the area surrounding the tumor (i.e., tumor microenvironment), without entering into the rest of the patient's system. In some embodiments, the administration of compositions allows the immunotherapeutic agent and locally administered chemotherapy to be distributed over a larger regional area, e.g. through large volumes of brain tissue.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al. (1981) *J. Biomed. Mater. Res.* 15:167; Langer (1982), *Chem. Tech.* 12:98), ethylene vinyl acetate (Langer et al. (1981) *J. Biomed. Mater. Res.* 15:167), or poly-D-(–)-3-hydroxybutyric acid (EP 133,988A). Sustained release compositions also include liposomally entrapped compositions comprising at least one immunotherapeutic agent combined with at least one locally administered chemotherapy which can be prepared by methods known in the art (Epstein et al. (1985) *Proc. Natl. Acad. Sci. U.S.A.* 82:3688; Hwang et al. (1980) *Proc. Natl. Acad. Sci. U.S.A.* 77:4030; U.S. Pat. Nos. 4,485, 045 and 4,544,545; and EP 102,324A). Ordinarily, the liposomes are of the small (about 200-800 angstroms) unilamelar type in which the lipid content is greater than about 30 mol % cholesterol, the selected proportion being adjusted for the optimal therapy. Such materials can comprise an implant, for example, for sustained release of the presently disclosed compositions, which, in some embodiments, can be implanted at a particular, pre-determined target site, such as at a solid tumor, or at a site at which a solid tumor has been surgically removed.

In another embodiment, the presently disclosed pharmaceutical compositions may comprise PEGylated therapeutics (e.g., PEGylated antibodies). PEGylation is a well-established and validated approach for the modification of a range of antibodies, proteins, and peptides and involves the attachment of polyethylene glycol (PEG) at specific sites of the antibodies, proteins, and peptides (Chapman (2002) *Adv. Drug Deliv. Rev.* 54:531-545). Some effects of PEGylation include: (a) markedly improved circulating half-lives in vivo due to either evasion of renal clearance as a result of the polymer increasing the apparent size of the molecule to above the glomerular filtration limit, and/or through evasion of cellular clearance mechanisms; (b) improved pharmacokinetics; (c) improved solubility—PEG has been found to be soluble in many different solvents, ranging from water to many organic solvents such as toluene, methylene chloride, ethanol and acetone; (d) PEGylated antibody fragments can be concentrated to 200 mg/ml, and the ability to do so opens up formulation and dosing options such as subcutaneous administration of a high protein dose; this is in contrast to many other therapeutic antibodies which are typically administered intravenously; (e) enhanced proteolytic resistance of the conjugated protein (Cunningham-Rundles et. al. (1992) *J. Immunol. Meth.* 152:177-190); (f) improved bioavailability via reduced losses at subcutaneous injection sites; (g) reduced toxicity has been observed; for agents where toxicity is related to peak plasma level, a flatter pharmacokinetic profile achieved by sub-cutaneous administration of PEGylated protein is advantageous; proteins that elicit an immune response which has toxicity consequences may also benefit as a result of PEGylation; and (h) improved thermal and mechanical stability of the PEGylated molecule.

Pharmaceutical compositions for parenteral administration include aqueous solutions of compositions comprising at least one immunotherapeutic agent combined with at least one locally administered chemotherapy. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of compositions include fatty oils, such as sesame oil, or synthetic fatty acid esters, such as ethyl oleate or triglycerides, or liposomes. Optionally, the suspension also can contain suitable stabilizers or agents that increase the solubility of the compositions comprising at least one immunotherapeutic agent combined with at least one locally administered chemotherapy to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

Regardless of the route of administration selected, the presently disclosed compositions are formulated into pharmaceutically acceptable dosage forms such as described herein or by other conventional methods known to those of skill in the art.

In general, the "effective amount" or "therapeutically effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

The term "combination" is used in its broadest sense and means that a subject is administered at least two agents, more particularly at least one immunotherapeutic agent combined with at least one locally administered chemotherapy. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state. In a further embodiment, at least one immunotherapeutic agent is administered before at least one locally administered chemotherapy. In a still further embodiment, at least one locally administered chemotherapy is administered before at least one immunotherapeutic agent.

Further, the presently disclosed compositions can be administered alone or in combination with adjuvants that enhance stability of the agents, facilitate administration of pharmaceutical compositions containing them in certain embodiments, provide increased dissolution or dispersion, increase activity, provide adjuvant therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of at least one immunotherapeutic agent combined with at least one locally administered chemotherapy can be varied so long as the beneficial effects of the combination of these agents are achieved. Accordingly, the phrase "in combination with" refers to the administration of at least one immunotherapeutic agent combined with at least one locally administered chemotherapy and, optionally, additional agents either simultaneously, sequentially, or a combination thereof. Therefore, a subject administered a combination of at least one immunotherapeutic agent in combination with at least one locally administered chemotherapy and, optionally, additional agents can receive at least one immunotherapeutic agent combined with at least one locally administered chemotherapy and, optionally, additional agents at the same time (i.e., simultaneously) or at different times (i.e., sequentially, in either order, on the same day or on different days), so long as the effect of the combination of all agents is achieved in the subject.

When administered sequentially, the agents can be administered within 1, 5, 10, 30, 60, 120, 180, 240 minutes or longer of one another. In other embodiments, agents administered sequentially, can be administered within 1, 2, 3, 4, 5, 10, 15, 20 or more days of one another. Where the agents are administered simultaneously, they can be administered to the subject as separate pharmaceutical compositions, each comprising either at least one immunotherapeutic agent in combination with at least one locally administered chemotherapy and, optionally, additional agents, or they can be administered to a subject as a single pharmaceutical composition comprising all agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_a Q_A + Q_b Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

In another aspect, the presently disclosed subject matter provides a pharmaceutical composition including at least one immunotherapeutic agent combined with at least one locally administered chemotherapy, optionally, additional agents, alone or in combination with one or more additional therapeutic agents in admixture with a pharmaceutically acceptable excipient.

More particularly, the presently disclosed subject matter provides a pharmaceutical composition comprising at least one immunotherapeutic agent combined with at least one locally administered chemotherapy and, optionally, additional agents and a pharmaceutically acceptable carrier.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams and Wilkins (2000).

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The term "instructing" a patient as used herein means providing directions for applicable therapy, medication, treatment, treatment regimens, and the like, by any means, but preferably in writing. Instructing can be in the form of prescribing a course of treatment, or can be in the form of package inserts or other written promotional material.

The term "promoting" as used herein means offering, advertising, selling, or describing a particular drug, combination of drugs, or treatment modality, by any means, including writing, such as in the form of package inserts. Promoting herein refers to promotion of the combination of an immunotherapeutic agent, such as an immune checkpoint molecule, and a chemotherapeutic agent formulated for local administration (e.g., intratumoral) for an indication, such as the treatment of cancer (e.g., brain cancer, e.g., glioblastoma), where such promoting is authorized by the Food and Drug Administration (FDA) as having been demonstrated to be associated with statistically significant therapeutic efficacy and acceptable safety in a population of subjects. In some embodiments, the presently disclosed subject matter provides a method of promoting a combination treatment for the treatment of a patient with a cancer, wherein the combination treatment comprises: (a) a locally administered chemotherapy; and (b) an immunotherapeutic agent. In some embodiments, promoting is not authorized by the Food and Drug Administration (FDA) (or other health regulatory agency, such as the European Medicines Agency (EMA), and promoting is for an off-label use. In some embodiments, the package insert provides instructions to receive cancer treatment with a locally administered chemotherapy in combination with an immunotherapeutic agent, such as an immune checkpoint molecule. In some embodiments, the package insert provides instructions to receive cancer treatment with a locally administered chemotherapy in combination with an immunotherapeutic agent. In some embodiments, the presently disclosed subject matter provides a method of instructing a patient with a cancer by providing instructions to receive a combination treatment comprising: (a) a locally administered chemotherapy; and (b) an immunotherapeutic agent, to extend survival of the patient. In some embodiments, the promotion is by a package insert accompanying a formulation comprising the locally administered chemotherapy and the immunotherapeutic agent. In some embodiments, the promotion is by written communication to a physician or health care provider. In some embodiments, the promotion is by oral communication to a physician or health care provider. In some embodiments, the promotion is by a package insert, wherein the package insert provides instructions to receive cancer treatment with a locally administered chemotherapy in combination with an immunotherapeutic agent.

II. Kits for Treating Cancer

The presently disclosed subject matter also relates to kits for practicing the methods of the presently disclosed subject matter. In general, a presently disclosed kit contains some or all of the components, reagents, supplies, and the like to practice a method according to the presently disclosed subject matter. In some embodiments, the term "kit" refers to any intended any article of manufacture (e.g., a package or a container) comprising at least one immunotherapeutic agent, such as an immune checkpoint molecule, at least one locally administered chemotherapy formulated for local administration (e.g., intratumoral), and a set of particular instructions for practicing the methods of the presently disclosed subject matter. The kit can be packaged in a divided or undivided container, such as a carton, bottle, ampule, tube, etc. The presently disclosed compositions can be packaged in dried, lyophilized, or liquid form. Additional components provided can include vehicles for reconstitution of dried components. Preferably all such vehicles are sterile and apyrogenic so that they are suitable for injection into a subject without causing adverse reactions.

In some embodiments, the presently disclosed subject matter provides a kit comprising: (a) a locally administered chemotherapy; (b) an immunotherapeutic agent; and (c) a package insert or label with directions to treat a patient with a cancer by administering a combination treatment comprising the locally administered chemotherapy and the immunotherapeutic agent. Those skilled in the art will appreciate that a kit can be assembled for the treatment of any cancer or solid tumor described herein.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Materials and Methods

Cells:

GL-261 luciferase positive cells (GL-261 LUC) were purchased from Caliper Life Sciences (Hopkinton, Mass.). Cells were grown in Dulbecco's Modified Eagle Medium (DMEM, Life Technologies, Grand Island, N.Y.) with 10% Fetal Bovine Serum (FBS, Gemini Bio-Products, West Sacramento, Calif.) plus 1% Penicillin/Streptomycin (Life Technologies, Grand Island, N.Y.) and 100 ug/mL of G418 (Invitrogen, San Diego, Calif.) in an incubator maintained at 37° C. with 5% $CO_2$. GL-261 ova luciferase positive cells (G1-261 ova-luc) were kindly donated by Dr. Ollin (University of Minnesota) (Ohlfest et al., 2013). Cells were grown in DMEM, with 10% FBS plus 1% Pen/Strep plus 500 ug/mL of G418.

Tumor Model:

Female C57BL/6J mice (The Jackson Laboratory, Bar Harbor, Me.), 6 to 8 weeks old, were implanted (Day 0) with GL-261 LUC cells to establish intracranial gliomas, as previously described (Zeng et al., 2013). Briefly, mice were anesthetized with ketamine/xylazine (100 mg/kg ketamine, 10 mg/kg xylazine) and a small midline incision was made to expose the skull. A burr hole was then drilled directly over the striatum and 130,000 GL-261 LUC cells were implanted at a depth of 3 mm from the cortical surface. The tumor take rate was 100%. Day 7 post implantation, mice were imaged to assess the progress of tumor growth using an IVIS platform (In Vivo Imaging System, Caliper Life Sciences, Hopkinton, Mass.). Mice were then stratified into experimental treatment groups based on luminescence. Each treatment group had 5 to 15 mice in the survival experiments. The treatment groups were as follows: control (3% ethanol in PBS administered intra-peritoneally), empty polymer (EP), anti-PD1, LC, i.p. BCNU (3% ethanol in PBS), i.p. BCNU+anti-PD1, LC+anti-PD1. All experiments were repeated at least in triplicate unless otherwise stated. The experimental schedules are explained in FIG. 1.

Adoptive Transfer Experiments:

For the adoptive transfer experiments, 5 week old female B6.SJL-Ptprca Pepcb/BoyJ mice expressing the congenic marker CD45.1 were used as the recipient mice. Inbred C57BL6/J (B6), B6.129S7-Rag1tm1Mom/J (RAG$^{-/-}$), B6.SJL-Ptprcb Pepcb/BoyJ (CD45.2) and C57BL/6-Tg (TcraTcrb)1100 Mjb/J (OT-I) mice were purchased from The Jackson Laboratory. 6-8 weeks old female RAG-/- OT-I CD45.2 transgenic mice were used as the donor mice.

RAG-/- OT-I CD45.2 mice were lethally anesthetized and their spleens were harvested and passed through a 40-µM nylon mesh. Red blood cell lysis buffer was consecutively applied to remove red blood cells. Cells were counted, checked for their viability, and washed twice with PBS. Two million cells were transferred in 100 uL of PBS for every recipient mouse via retro-orbital injection.

Mice were implanted with 300,000 Gl-261-ova-luc cells at day 0 and RAG-/- OT-I CD45.2 lymphocytes were transferred at day 13: 1 day before starting treatment with chemotherapy. The experimental schedule of the GL-261-ova tumor experiments is explained in detail in FIG. 1.

For in vivo cell proliferation tracing, OT-I RAG-/- splenocytes were labeled with cell proliferation dye eFluor450 (eBioscience, San Diego, Calif.) in the following way: Lymphocytes were isolated from spleen cells, their viability was checked post-isolation, and viable lymphocytes were washed with HBSS without $Ca^{2+}$ or $Mg^{2+}$ once in preparation for the staining. A 10 µM solution of the cell proliferation dye was made in HBSS without $Ca^{2+}$ and $Mg^{2+}$. After washing the isolated cells, the cells were reconstituted by adding the 10 µM dye solution to a concentration of $5 \times 10^6$ cells/mL. While the solution was added to the cells, the tube was gently vortexed to ensure homogeneous uptake of the dye by all cells.

The cells were incubated for 8 min in the dark at room temperature. Cells were quenched with 20 mls of HBSS with 20% FBS and were then spun at 1400 rpm for 5 min at 4° C. Cells were washed with HBSS without FBS an additional two times and cells were checked for viability. Cells were resuspended with HBSS (w/o FBS) to a concentration of $10 \times 10^6$ cells/mL. The cells were passed through a 40 µM cell strainer to ensure they were in a single cell suspension and 100 µL of the cell suspension was injected retro-orbitally in the recipient mice immediately.

For the adoptive transfer of CD8 cells from the LC+anti-PD1 group to the i.p. BCNU+anti-PD1 group, splenocytes from the LC+anti-PD1 group were harvested as described before and CD8 cells were isolated by negative isolation (Dynabeads untouched mouse CD8 cells kit, Life Technologies, Grand Island, N.Y.). Cells were washed with PBS two times after isolation and were passed through a 40 µM mesh to ensure a single cell suspension. Cells were resuspended to a concentration of $150 \times 10^6$ CD8 cells/mL and 100 µL of the cell suspension was injected in every mouse from the i.p. BCNU+anti-PD1 rechallenged group via retro-orbital injection.

Surgical Procedure: Polymer Implantation:

Mice in the LC or EP treatment groups were anesthetized with ketamine/xylazine (100 mg/kg ketamine, 10 mg/kg xylazine). The skin was prepped with alcohol swabs, the midline skin incision was opened, and the implantation burr hole created for tumor implantation was identified. The burr hole was re-drilled to allow for the polymer to enter the cranial cavity. The tumor mass was identified and the polymer was pushed directly on top of the tumor and secured under the skull. The skin incision was closed with staples. Mice were monitored for a period of 30 min after recovery for signs of neurological deficits.

Anti PD1 Monoclonal Antibody:

Hamster anti-murine PD1 monoclonal antibody-producing hybridoma (G4) was used to produce antibody as previously described (Hirano et al., 2005). Hamster immunoglobulin isotype antibody (Rockland Immunochemicals Inc., Gilbertsville, Pa.) was administered to animals receiving either BCNU polymers alone or i.p. BCNU alone.

Drugs:

BCNU was purchased from Sigma-Aldrich (St. Louis, Mo.) and dissolved in 100% EtOH in preparation for intra-peritoneal injection. After completely dissolving BCNU in EtOH, the solution was further diluted with 0.9% saline to a final concentration of 3% EtOH. Mice were injected within 5 min of the preparation of the drug.

The construction of BCNU wafers followed the standard protocol (Kim et al., 2007). BCNU was mixed with PCPP-SA polymer powder for a final concentration of 3.8% BCNU. EP, used as a control in this study, was constructed the same way as the BCNU wafer.

Flow Cytometric Analysis of Tumor Infiltrating Immune Cells and Peripheral Lymphoid Cell Populations:

At day 21 or day 30 post tumor implantation, mice were sacrificed using a lethal dose of ketamine/xylazine cocktail. The spleen, brain, cervical lymph nodes (LN), and bone marrow were harvested and passed through a 40-μm strainer. A 30%-37%-60% Percoll gradient (GE Healthcare, Buckinghamshire, UK) was used to isolate immune cell populations from brain tumors and the draining LNs. After centrifugation, the 37%-60% interface contained lymphocytes, monocytes, and microglia in the case of brain tumors, and lymphocytes and monocytes in the case of draining LNs.

Peripheral blood was collected by cardiac puncture before harvesting other tissues at day 21 and 30. A total of 600 μL was collected from each mouse in heparin-coated tubes (BD Biosciences, Franklin Lakes, N.J.). Blood was mixed with PBS in a 1:1 ratio and overlaid onto a Ficoll-Paque Plus (GE Healthcare) base in a 1:3 ratio. After centrifugation, peripheral lymphocytes were extracted from the resulting horizon and were washed twice with PBS.

Lymphocytes from all tissues were stimulated with PMA-Ionomycin and Golgi stop (eBioscience) for 4-6 hours in a 37° C. humidified incubator maintained at 5% $CO_2$. For flow cytometric analysis, lymphocytes were stained with CD8 PerCp-Cy5.5 Clone: 53-6.7 (eBioscience), CD3 FITC Clone: 17A2 (eBioscience), CD4 APCH7 Clone: GK1.5 (BD Biosciences), FoxP3 PE Clone: MF23 (BD Biosciences), IFN-γ APC Clone: XMG 1.2 (eBioscience), and fixable aqua L/D stain (Life Technologies). For the memory T cells, lymphocytes were stained with CD62L PE (BD Biosciences) and CD44 BV421 (BD Biosciences). For the myeloid cells and microglia, the following antibodies were used: Ly-6G APC Clone: RB6-8C5 (eBioscience), Ly-6C PE Clone: HK1.4 (eBioscience), CD11b AF700 Clone: M1/70 (Biolegend, San Diego, Calif.), CD11c BV421 Clone: N418 (Biolegend), CD45 PE-CF594 Clone: 30-F11 (BD Biosciences). Appropriate isotype controls were used. For the adoptive transfer experiment, CD45.2 PE Clone: 104 (eBioscience) was used to stain the isolated lymphocytes.

In addition to the blood draws performed on days 21 or 30 post implantation, blood draws were also performed on days 26 and 41 post implantation. On these days, blood was taken via tail vein sampling and 100 μL of blood was collected for every mouse. Red blood cells were lysed using RBC Lysis Buffer (eBioscience) and subsequently stained with CD3 FITC Clone: 17A2 (eBioscience). All flow cytometry experiments were performed on a LSRII (BD Biosciences) and analysis was performed using FlowJo software (TreeStar, Ashland, Oreg.).

Re-Challenge Experiments:

Tumor burden was assessed weekly with IVIS imaging. Mice were considered "cured" of their brain tumors following initial treatment if no evidence of tumor was present at consecutive IVIS imaging sessions, and mice were further considered long-term survivors if no tumor was detected 90 days post implantation. Long-term survivors from each experimental group were re-challenged 90 days post implantation with 300,000 GL-261 LUC cells injected intracranially in the contralateral hemisphere. Cells were prepared in 1 μL of PBS. Naïve mice were implanted in parallel as controls, and mice were followed with weekly IVIS imaging.

Statistics:

Survival was plotted using Kaplan-Meier curves, and curves were analyzed with the log-rank Mantel-Cox test using GraphPad Prism software (GraphPad Software, La Jolla, Calif.). For comparison of cell numbers and percentages between treatment groups in flow cytometry experiments, a two-tailed unpaired t test was used. P values <0.05 were considered significant.

Example 2

Systemic Chemotherapy is More Immunosuppressive than Local Chemotherapy in the Tumor Microenvironment and the Peripheral Lymphoid Organs Immediate Immunosuppressive Effect:

To track the evolution of the immunological response of tumor bearing mice to chemotherapy, the number of lymphocytes recovered from the brain as well as the spleen, blood, lymph nodes and bone marrow at earlier and later time points along the course of chemotherapy was examined (FIG. 1). Mice were followed with serial blood draws, and the blood circulating lymphocytes were tracked by the CD3 surface marker. Mice treated with i.p. BCNU showed a decreased number of CD3+ lymphocytes compared to control mice at the end of the first week of treatment with stably decreasing numbers over the course of treatment. At the end of the therapeutic regimen (Day 30 post implantation), i.p. BCNU treated mice were severely lymphodepleted for a long period that lasted for at least 2 weeks after the end of treatment (p-value<0.001) (FIG. 2). The same lymphodepleting pattern was observed in the draining lymph nodes (DLNs). The systemic chemotherapy group exhibited late myelotoxicity with the overall cellularity of the BM as well as the leukocytes (as measured by CD45) being lower than the control mice. However, LC did not affect the number of TILs or the lymphocytes in the peripheral lymphoid organs. On the contrary, an increase in the number of TILs at a late timepoint (Day 30) compared to systemic BCNU or control mice was observed.

Late Immunosuppressive Effect:

Systemic chemotherapy exhibited a prolonged and potentially irreversible lymphodepletion. A small percentage of mice treated with systemic chemotherapy or local chemotherapy were cured of their disease and they were able to be followed for a period of 4 months from the initial tumor implantation. Mice treated with systemic chemotherapy surprisingly showed a decreased number of recovered lymphocytes from the spleen (P=0.002), the LN (P<0.001) and the blood (P=0.07) compared to untreated mice or LC treated mice (FIG. 3).

Example 3

Use of Systemic Chemotherapy Post Immunotherapy Exhibits Inferior Survival and Immune Activation Compared to Local Chemotherapy As presented hereinabove, the delivery method of chemotherapy in tumor bearing mice poses a very important effect on the immune system, with systemic chemotherapy producing severe lymphopenia in the peripheral lymphoid organs and the tumor microenvironment while LC preserving an intact immune response. In light of these findings, it was determined whether immunotherapy would work best in combination with chemotherapy and if so, which delivery method would maximize the survival benefit and immune profile of tumor bearing mice. Mice in the EP treatment group had a median survival similar to that of control mice (25 vs 28 days, p=0.1). LC treatment alone increased survival compared to the EP group (28 vs 25 days, p=0.04). An increase in median survival was seen in the i.p. BCNU treatment group compared to LC (28 vs 45 days, p=0.02). The combination of i.p. BCNU+anti-PD1 resulted in similar survival compared to anti-PD1 alone (p=0.6) and showed a trend for increased survival compared to BCNU alone (p=0.2). LC+anti-PD1 had the greatest survival benefit with LC+anti-PD1 being superior to anti-PD1 alone (p=0.06) or LC alone (p=0.001). More importantly, in a larger cohort of mice (15 mice/group), LC+anti-PD1 exhibited higher survival compared to i.p. BCNU+anti-PD1 (p=0.03). FIG. 4 shows the survival data generated in control and treated tumor-bearing mice. FIG. 5 shows the tumor progression of intracranially implanted GL-261 tumors measured by bioluminescent imaging.

Circulating Lymphocytes:

The anti-PD1 treated group exhibited an increased number of CD3+ lymphocytes compared to control mice for a prolonged period of time (day 41, FIGS. 6 and 7) after the end of the therapeutic regimen. LC treated mice showed an increased number of CD3+ lymphocytes compared to the control group for an extended period of time (day 41, FIGS. 6 and 7). The combination of i.p. BCNU+anti-PD1 exhibited a similar lymphodepleting profile as seen after i.p. BCNU treatment alone: the number of CD3+ blood lymphocytes started decreasing at day 26 (FIGS. 6 and 7, p=0.02) and by day 30 reached the same levels as mice treated with i.p. BCNU alone (p=0.9). Mice treated with the combination of LC+anti-PD1 maintained the high number of blood circulating lymphocytes compare to the non-treated mice (FIGS. 6 and 7, p=0.5).

Draining Lymph Nodes:

Flow cytometric analysis of the draining lymph nodes confirmed lymphodepletion of both CD3+ cells and CD8+ IFN-γ+ cells in the i.p. BCNU and i.p. BCNU+anti-PD1 treatment groups. The anti-PD1, LC, and combination LC+anti-PD1 group had higher numbers of CD3+ and higher percentage of CD8+IFN-γ+ cells compared to control mice. The combination treatment did not result in higher percentage of CD8+IFN-γ+ cells compared to the monotherapies (FIGS. 8 and 9).

Bone Marrow (BM) Cells:

Upon live-dead staining of bone marrow cells harvested from the femurs of treated and control mice, it was found that mice in the i.p. BCNU group showed a significant decrease in cellularity (p<0.05). The addition of anti-PD1 failed to reconstitute the cellularity of the BM (p<0.01). The analysis of CD45+ bone marrow cells (leukocytes) from the i.p. BCNU and i.p. BCNU+anti-PD1 groups revealed decreased cell numbers compared to the control, LC or LC+anti-PD1 groups (p<0.05) (FIG. 10). A more detailed analysis of the specific myeloid subpopulations can be seen in FIGS. 11 and 12.

Tumor Infiltrating Lymphocytes (TILs):

Mice were sacrificed at days 21 and 30 and TILs were analyzed to assess the short-term and long-term effects of each treatment regimen on the lymphocytes present in the tumor microenvironment. At day 21, on average, 50% of the CD8+ cells recovered from control mice produced IFNγ. LC or i.p. BCNU groups exhibited a similar percentage of CD8+IFNγ+ cells with 40% and 35% of the recovered CD8+ cells producing IFN-γ, respectively (p=0.35 and p=0.5). The addition of anti-PD1 antibody to LC treatment increased the percentage of CD8-IFNγ producing cells to 70% (p<0.05), which was similar to anti-PD1 alone (FIGS. 13 and 14, p=0.87). The percent and number of CD4+FoxP3+ regulatory cells was higher in the i.p. BCNU group compared to the control (55% vs 30%, p=0.01). LC group moderately increased the percent of Tregs (40%) vs the control or the EP group. Anti-PD1 treatment had the same percentage of Tregs vs control (p=0.96). The addition of anti-PD1 to LC treatment moderately decreased the levels of CD4+FoxP3+ cells (38%) close to the level of the control mice (FIGS. 7 and 8, p<0.001) but did not significantly decrease the percentage of Tregs in combination with i.p. BCNU (50%, p=0.66) (FIGS. 13 and 15).

At day 30 post implantation, the density of CD3+TILs (number of cells normalized by tumor volume) in the i.p. BCNU group was significantly less than control mice in the control (40 vs 140 cells, p<0.0001). LC enhanced the percentage and number of CD8-IFNγ producing cells (42%, 80 cells) compared to the control group (15%, 30 cells, p<0.001). LC+anti-PD1 had a higher percentage of CD8-IFNγ producing cells (38%) compared to the control mice (15%, p<0.0001), but a similar percentage compared to LC (42%, p=0.38) or anti-PD1 treatment (38%, p=0.75). The percent of CD4+FoxP3+ cells was similar at day 30 among the control group (34%), the EP group (33%) and the anti-PD1 (27%) group. LC treatment continued to have a higher percentage of Tregs (52%) compared to the control group (27%, p<0.05), but the combination of LC+anti-PD1 normalized the percent of CD4+FoxP3+ cells (35%) to that of control mice (P=0.4).

Microglia Cells and Tumor Infiltrating Myeloid Cells:

Resident microglia were identified as CD11b+CD45[low] cells, infiltrating macrophages-monocytes as CD11b+CD45 [high] cells, and TILs as CD11b−CD45[high] cells. The lymphocytic population was identified as CD11b−CD45 [high]. At day 21, the anti-PD1 group and the LC group had lower levels of activated microglia compared to the control or EP group. The relative percentages of lymphocytes, microglia and monocytes exhibited variability among treatment groups with no distinct pattern specific for any treatment group. The relative percentage of resident microglia/macrophages compared to the rest of infiltrating immune cell population strongly correlated with tumor size regardless of the treatment group at day 21 (p-value=0.003, $r^2$=0.78) (FIGS. 16 and 17). Further analysis of the tumor infiltrating macrophages (TAMs) showed no distinct pattern among different treatment groups; however, a positive correlation existed between tumor size and monocyte/granulocyte ratio (p-value=0.04, $r^2$=0.5). Interestingly, tumor infiltrating dendritic cells defined as CD11b+CD11c+ cells gated from the population of CD45+ cells showed an increased % in the LC and LC+anti-PD1 groups compared to the EP or anti-PD1 treatment (FIG. 18). This result indicates that local chemotherapy is enhancing the infiltration of dendritic cells in the tumor microenvironment that can uptake the released by the dying tumor cells antigens and allow for greater antigen presentation.

Example 4

Use of Systemic Chemotherapy Concurrently with Immunotherapy Exhibits Inferior Survival Compared to Local Chemotherapy and Abrogates the Survival Benefit of Immunotherapy Mice in the LC group trended towards a longer median survival than the EP group (35 vs 23 days, P=0.07). Despite the use of chemotherapy (LC or systemic chemotherapy) at an earlier timepoint (day 7) (FIG. 19), the median as well as the long-term survival did not change compared to the later treatment in the first round of experiments (day 14) (FIG. 4).

The order of treatment similarly didn't change outcomes as LC prior or after anti-PD1 administration generated similar survival data (90% vs 80% long term survivors) (FIG. 4). However, when combining anti-PD1 with i.p. BCNU, systemic chemotherapy abrogated the survival benefit of anti-PD1 treatment (30% vs 55% long term survivors) (FIG. 4). Furthermore, the combination of anti-PD 1 and LC showed a statistically significant increase in survival in comparison to anti-PD1 and systemic chemotherapy (P=0.03).

Example 5

LC Increases the Survival and Homing of Tumor Antigen Specific T Cells in the Tumor Microenvironment and the Draining Lymph Nodes (DLNs) Whereas Systemic Chemotherapy is Abrogating this Effect In light of the flow cytometry results in the GL261 model showing an immune activation with LC and LC and anti-PD1, and to test the hypothesis that this activation occurs as a result of chemotherapy-induced cell death and subsequent antigen release, the antigen specific ova system was utilized. Mice were implanted with GL-261 ova cells and lymphocytes were adoptively transferred from OT-I mice that are genetically modified to express a T-cell receptor (TCR) with high affinity for the ovalbumin residues 257-264 in the context of the H2Kb MHC-I peptide. Four days after the adoptive transfer and three days after initiation of chemotherapy, the DLNs were harvested as well as the brains of the mice implanted with G1-261 ova-luc tumors. Flow analysis with CD3 and CD45.2 markers showed that the LC group had an increased percentage and number of adoptively transferred ova specific (CD45.2) T cells residing in the DLNs and the brain tumor microenvironment compared to the systemic chemotherapy groups or the anti-PD1 group (FIGS. 20 and 21). More specifically, a modest increase of CD3+CD45.2+ in the DLNs was observed in the LC treated mice compared to anti-PD1 treated mice (8% vs 4%, P=0.3). A significant increase of CD3+CD45.2+ transferred cells was observed in the LC treated mice compared to systemic BCNU and systemic BCNU and anti-PD1 treated mice (8% vs 3%, P=0.02). These profiles were more exaggerated within the tumor microenvironment; LC treated mice had a significantly higher percent of CD3+CD45.2+ cells compared to anti-PD1 treatment (18% vs 8%, P=0.02) as well as to i.p.BCNU (18% vs 4%, P=0.012) and i.p. BCNU and anti-PD1 (18% vs 6%, P=0.03) treatment. In vivo cell proliferation of adoptively transferred lymphocytes migrating to the spleen three days after the transfer shows that treatment with LC is allowing for a greater expansion of OT-I cells (94.9% cells divided) compared to EP (47.1%) or No Tx (43.2%) whereas i.p. BCNU is decreasing the proliferation of adoptively transferred lymphocytes (29.9%) (FIG. 22). Without wishing to be bound to any one particular theory, it is believed that these data support the hypothesis that LC indeed increases antigen-specific immune activity by increasing antigen-specific immune activity.

Example 6

Local Chemotherapy Preserves the Memory Response Against Tumor Rechallenge Whereas Systemic Chemotherapy Abrogates the Creation of Memory Response and Renders the T Memory Cells Dysfunctional After establishing that LC can be successfully combined with immunotherapy and showing that this combination can lead to an increased tumor specific immune response, it was determined whether the immunologic response elicited by the combination treatment would exhibit a long lasting memory response. In parallel with the LC groups, the memory response of systemic BCNU and systemic BCNU+anti-PD1 treatments was assessed.

Mice from the following treatment groups survived over 100 days post initial tumor implantation with no sign of tumor burden and were thus deemed long term survivors: anti-PD1, LC, i.p. BCNU, i.p. BCNU+anti-PD1, LC+anti-PD1. In order to assess memory response, long term survivors were re-challenged with GL-261 cells implanted in the contralateral hemisphere while naïve mice with no previous exposure to tumor cells were challenged in parallel. No tumor growth occurred in the anti-PD1 and LC+anti-PD1 groups indicating a memory response upon tumor antigen recognition. Naïve mice, in contrast, developed large, progressively growing tumors. Long-term survivors in the i.p. BCNU or i.p. BCNU+anti-PD1 groups were not able to inhibit tumor growth after tumor rechallenge (FIGS. 23 and 24).

Twenty days after intracranial tumor re-challenge, long-term survivor mice were assessed for the presence of memory cells. CD3+CD8+CD44[high]CD62L[low] cells were considered to be effector memory cells ($T_{EM}$) and CD3+CD8+CD44[low]CD62L[high] to be central memory T cells ($T_{CM}$). Mice treated with anti-PD1, i.p. BCNU, or LC+anti-PD1 exhibited similar percentages of CD4+ or CD8+$T_{CM}$ and $T_{EM}$ cells. Although $T_{EM}$ percentages were similar in all groups, assessment of IFNγ production after stimulation with PMA/Ionomyocin in CD8+CD44[high]CD62L[low] cells isolated from the DLNs, spleen or peripheral blood revealed dysfunctional IFNγ production in the i.p. BCNU treatment group as compared to the anti-PD1 or LC+anti-PD1 groups (FIGS. 25 and 26).

Example 7

Adoptive Transfer of CD8 Cells from Rechallenged LC+anti-PD1 Mice to I.P. BCNU+anti-PD1 Rechallenged Mice Creates Only a Partial Antitumor Response To identify whether the presence of intact CD8 memory cells could allow i.p. BCNU+anti-PD1 mice to regain their ability to reject the tumor after tumor rechallenge, CD8 cells were harvested from the spleen of mice treated with LC+anti-PD1 (that can successfully mount a memory immune response) and adoptively transferred in i.p. BCNU+anti-PD1 mice rechallenged with the tumor as described in FIG. 27. As mentioned previously, mice treated with i.p. BNCU+anti-PD1 and rechallenged with tumor fail to reject the tumor and very quickly grow large tumors from which they die on average at day 16 of the experiment. It is noteworthy that the tumor was very well established when the CD8 cells were adoptively transferred (day 12). Fifty percent (2/4) of the recipient mice showed a progressive decrease in the bioluminescent signal after the adoptive transfer of CD8 cells and entered a state of immunological equilibrium with the tumor signal being stable for more than three weeks (FIGS. 27 and 28). This indicates that the adoptively transferred effector CD8 cells were able to slow down the progression of the tumor but not completely eradicate the recurrent tumors implying that perhaps the adoptive transfer of memory CD8 cells is not adequate to maintain a strong immune response in these mice. However, when the partial responders were treated with anti-PD1, they exhibited similar antitumor response as chemotherapy naïve mice, indicating that upon infusion and reconstitution of the CD8 cell pool in the systemic chemotherapy mice, anti-PD1 treatment response was corrected (FIG. 28).

Example 8

Recurring Tumors after Tumor Rechallenge in Mice with Prior I.P. BCNU Treatment Cannot be Rescued by Anti-PD 1 Treatment In a separate set of experiments, long-term survivor mice from the systemic chemotherapy group were rechallenged with tumor and were treated with anti-PD1 in an attempt to salvage these mice from tumor progression. Mice implanted with primary tumor and treated with anti-PD1 only exhibited a 50% long term survival as expected, whereas mice treated with systemic chemotherapy for their primary tumor and salvaged with anti-PD1 for their rechallenged tumor (i.p. BCNU R and rescue anti-PD 1) failed to respond to anti-PD 1 treatment (FIG. 29); additionally, the rate of tumor progression in the i.p. BCNU R and rescue anti-PD1 group, as measured by bioluminescent imaging, was similar to the rate of tumor bearing mice that did not receive any treatment (FIG. 29). After harvesting peripheral blood, spleen and the brain of these rechallenged mice, it was confirmed that T memory cells from the systemic chemotherapy+anti-PD1 treatment mice exhibited a dysfunctional IFNγ production (FIGS. 30 and 31) compared to the LC and anti-PD1 treated mice, but it was further observed that anti-PD1 administration to the BCNU R mice did not restore the functionality of their memory T cells. More specifically, T memory cells in the brain parenchyma of LC and anti-PD1 treated mice showed a dramatically higher IFNγ production compared to i.p. BCNU R and rescue anti-PD1 mice (70% vs 20%, P=0.02). The same patterns of IFNγ production from T memory cells were observed in the peripheral blood with LC and anti-PD1 exhibiting the highest T memory associated IFNγ production (FIGS. 30 and 31). Upon necropsy of these mice at the experimental day 104, the size of the spleen in the systemic chemotherapy treated mice was significantly decreased compared to the LC and anti-PD1 treated mice (FIG. 32).

Example 9

Discussion

The use of chemotherapy in combination with immunotherapy has undoubtedly complex interactions. The doses used, the delivery method, as well as the type of chemotherapy and immunotherapy can affect the final outcome (Jackson et al., 2013). Chemotherapies with mild immunosuppressive effects, such as temozolamide, could allow for a potential therapeutic window of use with immunotherapy (van der Most et al., 2005). Certain chemotherapies seem to have differential effects in specific lymphoid subsets, such as cyclophosphamide, which preferentially depletes Tregs in low doses (Walter et al., 2013; Le and Jaffee, 2012). The type of cell death may also be important in stimulating the immune system. It has been hypothesized that cytotoxic treatments that lead to apoptosis are less effective in inducing a robust immune response as the organized cell death (apoptosis) does not allow for tumor antigen presentation, as compared to the antigen release that occurs with necrosis (van der Most et al., 2005). The timing of chemotherapy in combination with immunotherapy is also critical. The data suggest that administering immunotherapy to patients who have previously received systemic chemotherapy may render the immunotherapeutic agent ineffective.

The GL-261 syngeneic mouse glioblastoma model was used to assess the efficacy of combining PD1 blocking antibody with systemic or local BCNU. In a series of experiments, the different effects of local vs. systemic BCNU were defined on the cellular anti-tumor immune response and survival experiments were conducted to determine if the observed immunologic advantage translated to prolonged survival. It was found that local, rather than systemic, delivery of BCNU in combination with PD1 blockade is immunologically superior and results in significantly longer survival. Systemic chemotherapy depleted the lymphocyte population in the tumor mass, peripheral lymphoid organs, and peripheral blood. Administration of systemic BCNU to anti-PD1 treated mice abrogated the characteristic immunologic profile of anti-PD1 therapy. Conversely, the combination of local chemotherapy (LC) and PD1 blockade was associated with a robust immune response and increased survival compared with either monotherapy. These findings were validated in an antigen specific in vivo system; OT-I T cells were adoptively transferred to mice bearing GL-261-ova tumors undergoing treatment with a combination of chemotherapy and/or anti-PD1.

The series of experiments described hereinabove serve as evidence that locally delivered chemotherapy may be combined successfully with anti-PD1 mAb. The results indicate that biodegradable BCNU wafers in combination with anti-PD1 yield superior survival and immune stimulation compared to the combination of systemic, intraperitoneal BCNU (i.p. BCNU) and anti-PD1. Mechanistically, this treatment regimen affects several cell populations, including T cells, dendritic cells, migrating myeloid cells, and local microglia. Furthermore, in studying the effect LC or LC and anti-PD1 has on antitumor antigen specific T cell responses, it is shown that OT-I T cells adoptively transferred to mice bearing GL-261-ova tumors exhibit higher clonal expansion at both the draining lymph nodes as well as in the tumor microenvironment compared to all other treatment groups. These results imply that LC stimulates tumor-directed T cell responses triggered by increased antigen release from chemotherapy induced cell death. Although local BCNU+anti-PD1 generated the most long-term survivors, a percentage of mice from each treatment group became long-term survivors in this model. Upon tumor re-challenge, however, mice previously treated with i.p. BCNU+anti-PD1 did not reject brain tumor formation, whereas mice treated with LC+anti-PD1 rejected tumor formation. Furthermore, when the BCNU rechallenged mice were attempted to be salvaged with anti-PD1 treatment, the mice did not respond to treatment unlike the control mice treated with anti-PD1 that exhibited a complete response in 50% of the animals.

Accordingly, the presently disclosed subject matter demonstrates that local chemotherapy in the form of controlled-release BCNU polymers is superior to systemic BCNU for combination with anti-PD1 immunotherapy. This regimen provides a robust survival benefit as well as an increase in tumor-infiltrating immune cells and formation of memory cells necessary to resist tumor re-challenge. Taken together, these results highlight the importance of rigorously testing the effects of order, timing, and dosage in implementing combination chemotherapy/immunotherapy regimens.

While chemotherapy and immunotherapy have been widely used and validated independently, the combination of these two modalities has thus far been discouraged due to the known effects of chemotherapy on the immune system (van der Most et al., 2005). It is hypothesized that administration of LC would not have the same systemic immunosuppressive effects as systemic therapy and, therefore, is a preferable strategy for combination with immunotherapy (Jackson et al., 2013). In fact, it was found that local BCNU not only allowed for retained activity of anti-PD1, but actually boosted the immune response. One potential mechanism for this synergy might be increased antigen presentation as tumor cells die in response to chemotherapy. This hypothesis is supported by the increased percentage of DCs present in the LC groups compared to the control group or the anti-PD1 group. Tumor infiltrating dendritic cells (TIDC) have been shown to be potent antigen-presenting cells (Preynat-Seauve et al., 2006). By implanting GL-261 ova expressing cells in mice and adoptively transferring OT-I lymphocytes, it was confirmed that the increased TIDC in the LC allowed for a greater expansion of the adoptively transferred ova-specific lymphocytes in the brain and the DLNs compared to mice treated with anti-PD1 alone or anti-PD1 in combination with systemic BCNU. These results support the hypothesis that chemotherapy induced cell death as a result of LC treatment attracts more DCs, which uptake the released antigens allowing for a greater antigen presentation and further clonal activation of tumor specific T cell responses. However, the use of systemic chemotherapy seems to abrogate the creation of the antitumor antigen specific T cell responses.

These immunologic findings are consistent with the survival data. LC in combination with anti-PD1 exhibited the most robust survival benefit compared to the control and monotherapy groups, indicating a synergistic relationship leading to durable anti-tumor responses. Furthermore, these data show that systemic BCNU treatment (i.p. BCNU) does not work synergistically with anti-PD1. Interestingly, in this model, it was observed that anti-PD1 treatment had a very quick anti-tumor response with 50% of the mice that ended up being long-term survivors losing their BLI signal as early as day 14 (at the end of anti-PD1 treatment and the beginning of BCNU treatment). This implies that long-term survivorship in the i.p. BCNU+anti-PD1 group was mainly due to the anti-PD1 effect rather than the systemic BNCU administration. The use of systemic chemotherapy alone or in combination with anti-PD1 resulted in a delay in tumor progression compared to control or anti-PD1 treatment respectively; however the tumors gradually grew back resulting in late mortality, consistent with the results in human glioblastoma treatment (Stupp et al., 2009). Consistent with this argument are the results of the survival experiment where systemic chemotherapy was given prior to immunotherapy; addition of systemic chemotherapy to anti-PD1 did not provide a survival benefit and was in fact inferior to PD1 monotherapy (FIG. 19). Taken together, these data indicate that local and not systemic chemotherapy generates a significant increase in survival when combined with PD1 blockade over either monotherapy.

The effective combination of LC and anti-PD1 resulted in an enhanced anti-tumor immune response within the tumor microenvironment, further supporting the utility of combining chemotherapy and immunotherapy. The immunologic profile exhibited by mice treated with LC+anti-PD1 showed a decreased number of CD4+FoxP3+ cells and an increased number of CD8+IFN$\gamma$ producing cells as compared to mice in monotherapy or control groups. Interestingly, immune infiltration of CD8+IFN$\gamma$ producing cells was seen at day 30, but not at day 21, which could point to the local cytoreductive effect of BCNU treatment giving way to immune activation. The interaction between LC and anti-PD1 treatment and its effect on immune infiltration likely occurs on two fronts: the cytoreductive effect of the BCNU is concentrated within the first week after polymer implantation from day 14 to day 21 post tumor implantation due to the kinetics of BCNU release from the polymer (Fleming and Saltzman). The presence of BCNU in the tumor microenvironment leads to cell death and decreased proliferation of immune cells infiltrating the tumor microenvironment at day 21 as seen with other locally administered chemotherapy (Litterman, Dudek, et al., 2013; Litterman, Zellmer, et al., 2013). Persistent antigen stimulation, as a result of chemotherapy-induced tumor cell death at the first week of polymer implantation continues to attract effector T cells in the tumor; the decreased concentration of BCNU the second week after polymer implantation allows for effector T cells to exert their anti-tumor function (Hailemichael and Overwijk). Both local chemotherapy and systemic chemotherapy increased the percent of T-regulatory cells at day 21 and day 30. The addition of anti-PD1 to local chemotherapy but not to systemic chemotherapy decreased the percentage of T-regulatory cells at days 21 and 30 leading to an increased Teff/Treg ratio in the LC+anti-PD1 group at day 30. LC and anti-PD1 monotherapy groups were included in the flow cytometric analysis to identify the contribution each treatment had in the tumor microenvironment. As expected, the anti-PD1 monotherapy group exhibited increased infiltration of TILs, with increased numbers of CD8+IFN$\gamma$ producing cells and decreased numbers of CD4+FoxP3+ cells (Pardoll, 2012) whereas LC increased the CD4+FoxP3+ cells and provided an initial (day 21) moderate decrease of CD8+IFN$\gamma$ producing cells. However, LC enriched the tumor microenvironment for CD8+IFN$\gamma$ producing cells at day 30 compared to the control group.

Further, the effect of chemotherapy and/or anti-PD1 on peri-tumoral microglia was explored. As described previously (Gabrusiewicz et al., 2011), resident microglia promote an immunosuppressive microenvironment facilitating the establishment and progression of GBM. The interaction between glial cells and microglia transforms the latter to the amoeboid (activated) state and selectively activates the MAPK pathway without the secretion of pro-inflammatory cytokines. The release of TGF-b and several other immunosuppressive cytokines from activated microglia in combination with dysfunctional Toll-like receptor (TLR) responses prevents microglia from functioning as scavenger-antigen presenting cells (APCs), as is the case in the tumor-free state (Hussain et al., 2006). Consistent with previous studies, the percent of resident microglia/macrophages (CD11b+, CD45+) in control mice post tumor implantation constitutes the majority of glioma infiltrating immune cells. However, anti-PD1 treatment preferentially increases the percent of TILs compared to resident microglia/macrophages. This hypothesis is supported by an increased Teff/Treg ratio, favoring an effector phenotype in the anti-PD1 group. LC increased the percent of both TILs and microglia leading to a higher percent of microglia compared to TILs. This observation warrants further investigation as the positive TILs: microglia/macrophages ratio may be an artifact of reduced tumor size. This hypothesis is supported by the strong correlation between tumor size and microglia/macrophage: TILs ratio (p-value=0.003, $r^2$=0.78) and the absence of a distinct pattern in the above ratio when comparing different treatment groups.

The immune profile in the peripheral blood and lymphoid organs reflected the changes depicted in the tumor microenvironment. Systemic administration of BCNU depleted CD3+ cells in the draining LNs, the peripheral blood and caused myelotoxicity. CD8+IFNγ-producing cells were increased by percentage in both the peripheral blood and the draining lymph nodes in the combination LC+anti-PD1 group. LC or anti-PD1 alone did not have any effect on the percent of CD8+ cells producing IFNγ producing cells in the periphery. Although the systemic administration of BCNU did not affect the percentage of CD8+IFNγ producing cells, it did greatly deplete the number of cells present in the peripheral organs.

The re-challenge experiments show that anti-PD1 therapy generates immunologic memory against tumor antigens, resulting in tumor rejection upon re-challenge. Interestingly, systemic BCNU abrogated this effect. Local BCNU, however, allowed for persistence of immunologic memory imparted with anti-PD1 therapy. Flow cytometric analysis of re-challenged mice supports the hypothesis that i.p. BCNU disrupts memory T cell function. The analysis of $T_{EM}$ cells from the peripheral lymphoid organs (DLNs, peripheral blood, spleen) shows that cells from i.p. BCNU-treated mice exhibit dysfunctional IFNγ production compared with anti-PD1 or LC+anti-PD1 groups. Furthermore, the lack of a complete antitumor response in i.p. BCNU+anti-PD1 rechallenged mice after adoptive transfer of CD8 cells from LC+anti-PD1 mice that rejected the tumor upon rechallenge implies that CD8 memory cells alone are not sufficient to produce a rapid and complete antitumor response. Without wishing to be bound to any one particular theory and putting the survival data and the rechallenge-memory response results together, it can be postulated that the late recurrence of the disease after systemic BCNU treatment (as shown in the survival experiments, but more importantly in the treatment responses in patients) may be attributed to two factors: a) acquired mutations of the tumor after the use of DNA-damaging agents and b) the lack of effector memory cells that can eliminate tumor clones encountered in the past but not successfully eliminated at that time. Additionally, i.p. BCNU R and rescue anti-PD1 mice did not show a survival or immunologic response to anti-PD1 treatment as expected in chemotherapy naïve anti-PD1 treated mice.

Conclusively, the presently disclosed subject matter provides evidence of superior immunological response and greater tumor regression when LC and anti-PD1 treatment are combined. Systemic BCNU abrogates the positive survival and immunological profile anti-PD1 provides to mice bearing murine glioblastoma tumors. Furthermore, systemic chemotherapy, unlike LC, fails to prevent recurrence of the tumor upon tumor rechallenge and abrogates the memory response created by anti-PD1. The lack of memory response upon tumor rechallenge can be explained by a decrease in the memory T cell response.

Accordingly, it is concluded that intratumoral, controlled release BCNU is a superior treatment modality compared with systemic BCNU for combination with immunotherapy. This strategy circumvents the immunosuppressive effects of systemic chemotherapy and has a particularly robust effect on maintaining the memory T-cell population. Since BCNU-eluting polymers are currently approved for use in recurrent and newly diagnosed glioblastoma, this strategy may be readily translated into clinical trials. Immunotherapy and anti-PD1 mAb specifically has been successfully used for the treatment of non-central nervous system tumors but, based on the results presented herein, its therapeutic effect might be underestimated due to its use post systemic chemotherapy. The results presented here can have significant implications on the therapeutic strategy used for the treatment of multiple cancer types, such as glioblastoma.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Blackburn, S. D., et al., Coregulation of CD8+ T cell exhaustion by multiple inhibitory receptors during chronic viral infection. *Nature Immunology.* 2009; 10(1): 29-37.

Bloch, O., et al., Gliomas promote immunosuppression through induction of B7-H1 expression in tumor-associated macrophages. *Clinical Cancer Research: an Official Journal of the American Association for Cancer Research.* 2013; 19(12):3165-75.

Brahmer, J. R., et al., Safety and activity of anti-PD-L1 antibody in patients with advanced cancer. *The New England Journal of Medicine.* 2012; 366(26):2455-65.

Brem, H., Polymers to treat brain tumours. *Biomaterials.* 1990; 11(9):699-701.

Brem, H., et al., Placebo-controlled trial of safety and efficacy of intraoperative controlled delivery by biodegradable polymers of chemotherapy for recurrent gliomas. The Polymer-Brain Tumor Treatment Group. *Lancet.* 1995; 345(8956):1008-12.

Brooks, W. H., et al., Depressed cell-mediated immunity in patients with primary intracranial tumors. Characterization of a humoral immunosuppressive factor. *The Journal of Experimental Medicine.* 1972; 136(6):1631-47.

Fleming, A. B. and Saltzman, W. M. Pharmacokinetics of the carmustine implant. *Clinical Pharmacokinetics.* 2002; 41(6):403-19.

Gabrusiewicz, K., et al., Characteristics of the alternative phenotype of microglia/macrophages and its modulation in experimental gliomas. *PloS One.* 2011; 6(8):e23902.

Gilbert, M. R., et al., Dose-dense temozolomide for newly diagnosed glioblastoma: a randomized phase III clinical trial. *J. Clin. Oncology: Official Journal of the American Society of Clinical Oncology.* 2013; 31(32):4085-91.

Grossman, S. A., et al., Immunosuppression in patients with high-grade gliomas treated with radiation and temozolomide. *Clinical Cancer Research: an Official Journal of the American Association for Cancer Research.* 2011; 17(16):5473-80.

Hailemichael, Y. and Overwijk, W. W., Cancer vaccines: Trafficking of tumor-specific T cells to tumor after therapeutic vaccination. *The International Journal of Biochemistry & Cell Biology.* 2014; 53:46-50.

Hamid, O., et al., Safety and tumor responses with lambrolizumab (anti-PD1) in melanoma. *The New England Journal of Medicine.* 2013; 369(2):134-44.

Hirano et al., Blockade of B7-H1 and PD-1 by monoclonal antibodies potentiates cancer therapeutic immunity. *Cancer Res.* 2005 Feb. 1; 65(3): 1089-96

Hussain, S. F., et al., The role of human glioma-infiltrating microglia/macrophages in mediating antitumor immune responses. *Neuro-Oncology.* 2006; 8(3):261-79.

Jackson, C., et al., Vaccine strategies for glioblastoma: progress and future directions. *Immunotherapy.* 2013; 5(2):155-67.

Kim, G. Y., et al., Resorbable polymer microchips releasing BCNU inhibit tumor growth in the rat 9 L flank model. *Journal of Controlled Release: Official Journal of the Controlled Release Society.* 2007; 123(2):172-8.

Le, D. T and Jaffee, E. M., Regulatory T-cell modulation using cyclophosphamide in vaccine approaches: a current perspective. *Cancer Research.* 2012; 72(14):3439-44.

Litterman, A. J., et al., Alkylating chemotherapy may exert a uniquely deleterious effect upon neo-antigen-targeting anticancer vaccination. *Oncoimmunology.* 2013; 2(10): e26294.

Litterman, A. J., et al., Profound impairment of adaptive immune responses by alkylating chemotherapy. Journal of immunology. 2013; 190(12):6259-68.

Malmstrom, A., et al., Temozolomide versus standard 6-week radiotherapy versus hypofractionated radiotherapy in patients older than 60 years with glioblastoma: the Nordic randomised, phase 3 trial. *The Lancet Oncology.* 2012; 13(9):916-26.

Menard, C., et al., Cancer chemotherapy: not only a direct cytotoxic effect, but also an adjuvant for antitumor immunity. *Cancer Immunology, Immunotherapy: CII.* 2008; 57(11):1579-87.

Nowak, A. K., et al., Gemcitabine exerts a selective effect on the humoral immune response: implications for combination chemo-immunotherapy. *Cancer Research.* 2002; 62(8):2353-8.

Ohlfest, J. R., et al., Vaccine injection site matters: qualitative and quantitative defects in CD8 T cells primed as a function of proximity to the tumor in a murine glioma model. *Journal of Immunology.* 2013; 190(2):613-20.

Pardoll, D. M., The blockade of immune checkpoints in cancer immunotherapy. *Nature Reviews Cancer.* 2012; 12(4):252-64.

Parsa, A. T., et al., Loss of tumor suppressor PTEN function increases B7-H1 expression and immunoresistance in glioma. *Nature Medicine.* 2007; 13(1):84-8.

Preynat-Seauve, O., et al., Tumor-infiltrating dendritic cells are potent antigen-presenting cells able to activate T cells and mediate tumor rejection. *Journal of Immunology.* 2006; 176(1):61-7.

Sampson, J. H., et al., Immunologic escape after prolonged progression-free survival with epidermal growth factor receptor variant III peptide vaccination in patients with newly diagnosed glioblastoma. *Journal of Clinical Oncology: an Official Journal of the American Society of Clinical Oncology.* 2010; 28(31):4722-9.

Sampson, J. H., et al., Greater chemotherapy-induced lymphopenia enhances tumor-specific immune responses that eliminate EGFRvIII-expressing tumor cells in patients with glioblastoma. *Neuro-Oncology.* 2011; 13(3):324-33.

Sarkaria, J. N., et al., Combination of temsirolimus (CCI-779) with chemoradiation in newly diagnosed glioblastoma multiforme (GBM) (NCCTG trial N027D) is associated with increased infectious risks. *Clinical Cancer Research: an Official Journal of the American Association for Cancer Research.* 2010; 16(22):5573-80.

Stupp, R., et al., Effects of radiotherapy with concomitant and adjuvant temozolomide versus radiotherapy alone on survival in glioblastoma in a randomised phase III study: 5-year analysis of the EORTC-NCIC trial. *The Lancet Oncology.* 2009; 10(5):459-66.

Topalian, S. L., et al., Safety, activity, and immune correlates of anti-PD1 antibody in cancer. *The New England Journal of Medicine.* 2012; 366(26):2443-54.

van der Most, R. G., et al., Combining immunotherapy with chemotherapy to treat cancer. *Discovery Medicine.* 2005; 5(27):265-70.

Walter, S., et al., Single-dose cyclophosphamide synergizes with immune responses to the renal cell cancer vaccine IMA901. *Oncoimmunology.* 2013; 2(1):e22246.

Westphal, M., et al., A phase 3 trial of local chemotherapy with biodegradable carmustine (BCNU) wafers (Gliadel wafers) in patients with primary malignant glioma. *Neuro-Oncology.* 2003; 5(2):79-88.

Zeng, J., et al., Anti-PD1 blockade and stereotactic radiation produce long-term survival in mice with intracranial gliomas. *International Journal of Radiation Oncology, Biology, Physics.* 2013; 86(2):343-9.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for reducing recurrence of recurrent human glioblastoma multiforme, the method consisting of:
    administering to a human patient with recurrent glioblastoma multiforme an effective amount of a combination treatment consisting of:
        (a) a locally administered chemotherapy comprising a BCNU implantable wafer; and
        (b) nivolumab,
    wherein recurrence of the glioblastoma multiforme is inhibited.

2. A method for treating human glioblastoma and reducing glioblastoma recurrence in humans, the method consisting of:
    (i) surgically removing all or a portion of a solid glioblastoma tumor in a human patient with recurrent glioblastoma multiforme; and
    (ii) administering to the human patient with recurrent glioblastoma multiforme an effective amount of a combination treatment consisting of:
        (a) a locally administered chemotherapy comprising a BCNU implantable wafer; and
        (b) nivolumab,
    wherein recurrence of the glioblastoma is inhibited.

3. The method of claim 2, wherein locally administered chemotherapy is administered intratumorally and/or within a tumor bed.

4. The method of claim 2, wherein CD8+IFNγ producing cells are increased in the human patient with recurrent glioblastoma multiforme.

5. The method of claim 2, wherein the locally administered chemotherapy increases antigen release from tumor cells in the human patient with recurrent glioblastoma multiforme.

6. A method for increasing antigen release from tumor cells in a human patient with glioblastoma, the method consisting of:

administering to the human patient with glioblastoma an effective amount of a combination treatment consisting of:

(a) a locally administered chemotherapy comprising a BCNU implantable wafer; and (b) nivolumab.

7. The method of claim 6, wherein the glioblastoma is recurrent glioblastoma multiforme.

8. A method for increasing CD8+IFNγ producing cells in a human patient with glioblastoma, the method consisting of:

administering to the human patient with glioblastoma an effective amount of a combination treatment consisting of:

(a) a locally administered chemotherapy comprising a BCNU implantable wafer; and (b) nivolumab.

9. The method of claim 8, wherein the glioblastoma is recurrent glioblastoma multiforme.

\* \* \* \* \*